(12) United States Patent
Levin et al.

(10) Patent No.: US 11,521,732 B2
(45) Date of Patent: Dec. 6, 2022

(54) SYSTEMS AND METHODS OF MANAGING CUSTOMIZED RUN DISPLAY ELEMENTS WITH TREATMENT TEMPLATES BASED ON TREATMENT DOMAIN-SPECIFIC PROTOCOLS

(71) Applicant: Align Technology, Inc., San Jose, CA (US)

(72) Inventors: Adi Levin, Nes Tziona (IL); Anton Lapshin, Nizhniy Novgorod (RU); Behnam J. Foroodian, Livermore, CA (US); Eric P. Meyer, Pleasanton, CA (US); Konstantin Tenzin, Balashikha (RU); Andrey Chekhonin, Moscow (RU); Pavel Sokolov, Moscow (RU); René M. Sterental, Palo Alto, CA (US); Jason Ramos, San Jose, CA (US); Evgeniy Malashkin, Moscow (RU); Anna Sivakova, Moscow (RU); Michael Flanagan, Redwood City, CA (US)

(73) Assignee: Align Technology, Inc., San Jose, CA (US)

(*) Notice: Subject to any disclaimer, the term of this patent is extended or adjusted under 35 U.S.C. 154(b) by 192 days.

(21) Appl. No.: 16/399,847

(22) Filed: Apr. 30, 2019

(65) Prior Publication Data
US 2019/0333622 A1   Oct. 31, 2019

Related U.S. Application Data

(60) Provisional application No. 62/664,684, filed on Apr. 30, 2018.

(51) Int. Cl.
*G16H 50/20* (2018.01)
*G16H 20/30* (2018.01)
(Continued)

(52) U.S. Cl.
CPC .............. *G16H 20/30* (2018.01); *A61C 7/002* (2013.01); *A61C 7/08* (2013.01); *A61C 7/10* (2013.01);
(Continued)

(58) Field of Classification Search
CPC ........... A61C 7/002; A61C 7/00; A61C 7/146; A61C 9/0046; A61C 13/0004; A61C 7/08;
(Continued)

(56) References Cited

U.S. PATENT DOCUMENTS

| 5,975,893 A | 11/1999 | Chishti et al. |
| 7,134,874 B2 | 11/2006 | Chishti et al. |

(Continued)

FOREIGN PATENT DOCUMENTS

| CN | 105408904 A | 3/2016 |
| CN | 107256344 A | 10/2017 |

(Continued)

OTHER PUBLICATIONS

Roschin et al.; U.S. Appl. No. 16/826,036 entiteld "Automatic application of doctor's preferences workflow using statistical preference analysis," filed Mar. 20, 2020.

*Primary Examiner* — Maroun P Kanaan
(74) *Attorney, Agent, or Firm* — Shay Glenn LLP

(57) ABSTRACT

In various implementations, computer-implemented method, such as one executed on a computer system or on instructions stored on computer-readable media may include: receiving from a user device associated with a user, a request to access one or more treatment plans for patient; identifying a treatment template for user, the treatment template representing treatment preferences of the user, the treatment template being expressed according to treatment domain-specific protocols; processing the treatment tem- (Continued)

plate with the treatment domain-specific protocols to convert one or more parts of the treatment template into one or more runtime elements that interactively display customized user interface elements related to the treatment plan, the customized user interface elements configured to provide one or more customized user interactions with the treatment plan in accordance with the treatment preferences of the user; and providing instructions to display the one or more runtime elements on the user device.

32 Claims, 40 Drawing Sheets

(51) Int. Cl.
  *G06F 3/0482* (2013.01)
  *G06F 3/04845* (2022.01)
  *A61C 7/00* (2006.01)
  *A61C 7/08* (2006.01)
  *A61C 7/10* (2006.01)
  *G16H 20/00* (2018.01)
  *G16H 50/00* (2018.01)
  *G16H 50/70* (2018.01)
  *G16H 20/40* (2018.01)

(52) U.S. Cl.
  CPC ........ *G06F 3/0482* (2013.01); *G06F 3/04845* (2013.01); *G16H 20/00* (2018.01); *G16H 50/00* (2018.01); *G16H 50/70* (2018.01); *G16H 20/40* (2018.01)

(58) Field of Classification Search
  CPC . A61C 7/10; A61C 7/02; G06Q 10/06; G16H 50/50; G16H 80/00; G16H 20/30; G16H 20/00; G16H 50/00; G16H 50/70; G16H 20/40; G06F 3/0482; G06F 3/04845
  See application file for complete search history.

(56) References Cited

U.S. PATENT DOCUMENTS

| | | | |
|---|---|---|---|
| 7,220,122 B2 | 5/2007 | Chishti | |
| 7,892,474 B2 | 2/2011 | Shkolnik et al. | |
| 7,930,189 B2 | 4/2011 | Kuo | |
| 7,987,099 B2 | 7/2011 | Kuo et al. | |
| 8,469,705 B2 * | 6/2013 | Sachdeva ................ | A61C 7/00 433/24 |
| 9,161,824 B2 * | 10/2015 | Chishti .................... | A61C 7/00 |
| 2005/0019721 A1 * | 1/2005 | Chishti .................... | A61C 7/00 433/24 |
| 2007/0168152 A1 | 7/2007 | Matov et al. | |
| 2007/0238065 A1 | 10/2007 | Sherwood et al. | |
| 2008/0305452 A1 | 12/2008 | Sterental et al. | |
| 2008/0305454 A1 * | 12/2008 | Kitching ................. | A61C 7/00 433/24 |
| 2010/0179789 A1 | 7/2010 | Sachdeva et al. | |
| 2012/0035956 A1 | 2/2012 | Cane et al. | |
| 2014/0061974 A1 | 3/2014 | Tyler | |
| 2014/0122027 A1 | 5/2014 | Andreiko et al. | |
| 2014/0265034 A1 | 9/2014 | Dudley | |
| 2015/0097315 A1 | 4/2015 | DeSimone et al. | |
| 2015/0097316 A1 | 4/2015 | DeSimone et al. | |
| 2015/0102532 A1 | 4/2015 | DeSimone et al. | |
| 2018/0293354 A1 * | 10/2018 | Dejori .................... | G16H 50/20 |
| 2019/0175303 A1 | 6/2019 | Akopov et al. | |
| 2019/0328487 A1 | 10/2019 | Levin et al. | |
| 2019/0328488 A1 | 10/2019 | Levin et al. | |
| 2020/0297458 A1 | 9/2020 | Roschin et al. | |

FOREIGN PATENT DOCUMENTS

| | | |
|---|---|---|
| CN | 107645921 A | 1/2018 |
| JP | 2013146327 A | 8/2013 |
| WO | WO2008/149221 A1 | 12/2008 |

* cited by examiner

Alternative overview of treatment plan formation

Posterior Cross-bite
*improve posterior cross-bite* (default)
do not improve posterior cross-bite (maintain)
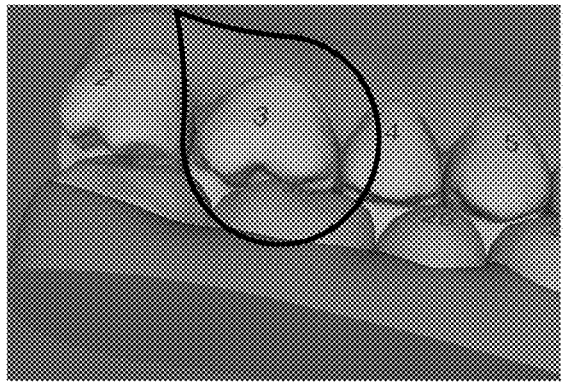
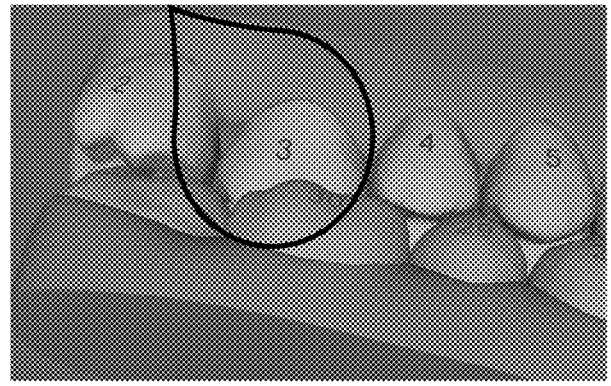
FIG. 5A
FIG. 5B
Attachments (Bite Ramps)
Default (no bite ramps)
CRT attachment shall be placed on premolars for all cases. Bite ramps are placed for all cases except Open bite and Rotated laterals
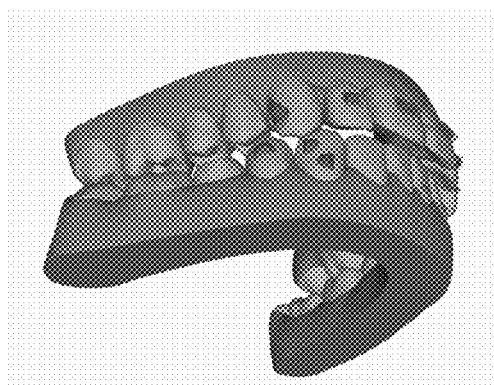
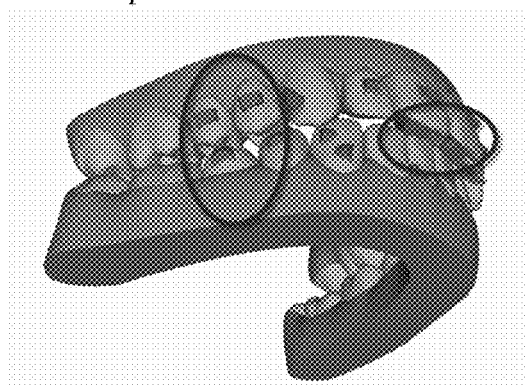
FIG. 6A
FIG. 6B Attachments (Position of Attachments on Teeth)
Align Default
CRT attachment shall be placed as gingival as possible
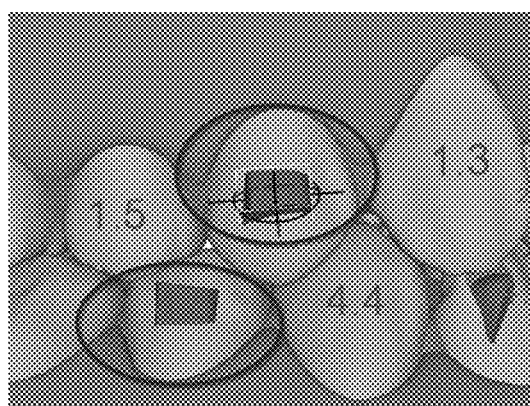
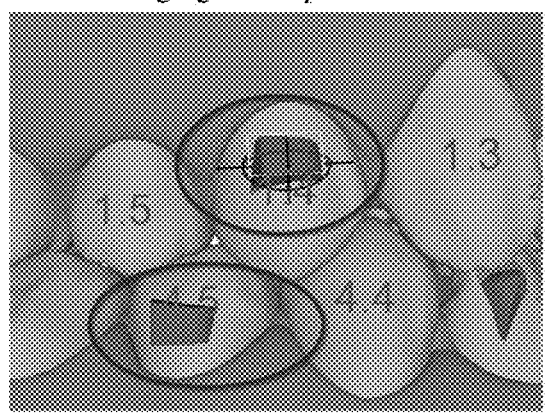
FIG. 7A
FIG. 7B
Target Overbite
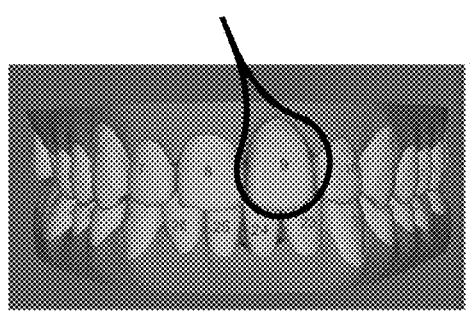
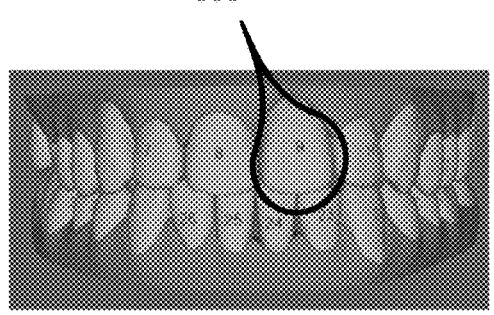
FIG. 8A
FIG. 8B

Attachments

Default (no bite ramps)

Lingual CRT attachment shall be placed for lower anterior intrusion

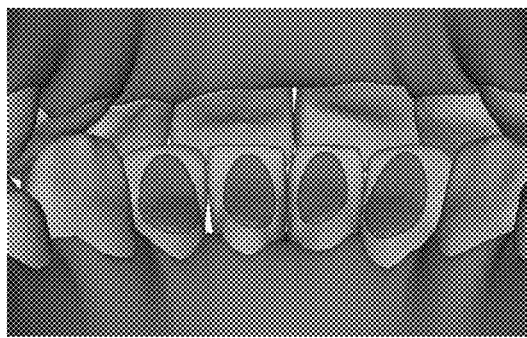

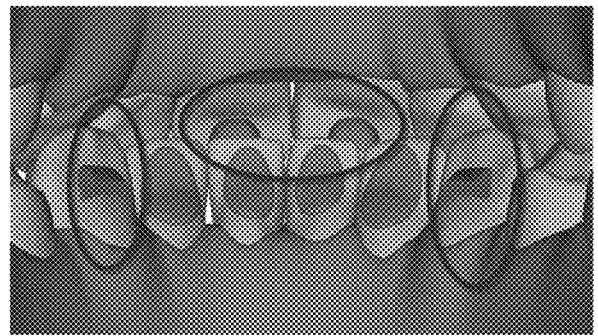

| Protocol declaration | Declare a protocol's name and its visibility (public or private) | public protocol Galler ( ... ) |
|---|---|---|
| Setting | Declares a setting that affects one or more of the treatment planning phases (Fipos / Staging / Attachments / MTP). Includes a verb and a noun, and optional arguments, which may be keyword arguments. Terminated by ";". | disable class_correction; restrict movements ( teeth: molars ); limit ipr (teeth: anteriors, max_amount: 0.30 mm); set filters ( any_product, open_bite, overjet, ipr, attachments ); put hook(on: upper canines); |

FIG 10(i)

| | | |
|---|---|---|
| Condition | A conditional "if" statement precedes a setting or an entire block of code. The predicate begins with the keyword "initially" / "performing" / "exists" to denote the context of the condition (referring to the initial position, final position, treatment goals or existence of teeth or other conditions)<br><br>Some conditions involve comparison operators ">", "<" and distance measurements such in millimeters<br><br>Boolean operators "and", "or" and "not" can be used to combine and negate conditions<br><br>The keyword "else" denotes the complement condition | ```
if (initially
open_bite >
0.5mm) ...
if (performing
intrusion(upper
anteriors) >
0.5mm) ...
if (performing
extrusion(lower
molars) > 0.5mm
and initially
posterior_open_
bite > 0.3mm)
...
if (not
performing
distalization(u
pper molars))
  apply
sequential_move
ment(direction:
extrusion,
teeth: (upper
premolars,
upper molars));
else
  apply
sequential_move
ment(direction:
extrusion,
teeth: (upper
molars, upper
premolars));
``` |
| Numerical values with units of measurements | Numbers can be integers or floating point decimals.<br><br>Angular values are succeeded by "degrees".<br><br>Distance values are succeeded by "mm".<br><br>Percentage values are succeeded by "%". | ```
50%
1.5 mm
-0.5mm
30 degrees
``` |

FIG 10(ii)

| | | |
|---|---|---|
| Teeth ranges | A range of teeth can be indicated by either a single word (e.g. "canines") or may be preceded by "upper / lower" and "left / right". The keyword "and" can be used to unite ranges of teeth. "1st" / "2nd" / "3rd" may preceded premolars and molars.<br><br>Primary teeth are indicated by adding "primary" before the tooth name. | canines<br>molars<br>canines and molars<br>upper left molars and lower left molars<br>upper 2nd premolar and lower 2nd premolar<br>primary second molars<br>upper primary centrals |
| Lists | A sequence of entities where the order matters, comma-separated and indicated by square brackets "[ ]". | apply movement_separation(teeth: anteriors, order: {lingual_root_torque, intrusion});<br>apply sequential_movement(movement: mesialization, overlap: 0%, order: {incisors, canines}); |

FIG 10(iii)

| | | |
|---|---|---|
| Blocks and nested blocks | Curley braces are used to mark blocks of IPL code, and blocks may contain conditions followed by nested blocks. | ```
if (performing
extrusion(upper
molars) >
0.5mm) {
  if (not
performing
distalization(u
pper molars)) {
    apply
sequential_move
ment(direction:
extrusion,
teeth: {upper
premolars,
upper molars});
  } else {
    apply
sequential_move
ment(direction:
extrusion,
teeth: {upper
molars, upper
premolars});
  }
}
``` |
| "For" loops | | |

FIG 10(iv)

To repeat a set of instructions over a range of teeth, quadrants or for each jaw, precede a block with "for each tooth" / "for each quadrant" / "for each jaw".

Teeth IDs inside "for" loops

Inside a "for each quadrant" or "for each jaw" loop, all teeth indications are implicitly restricted to that jaw or quadrant, e.g. the word "canine" inside a "for each jaw" loop means either "upper canine" or "lower canine" in each iteration of the loop.

Inside a "for each tooth" loop, teeth indications can be omitted, or a relative tooth ID can be used, i.e. the word "mesial"/"distal" refer to the adjacent teeth in the mesial/distal direction respectively.

```
for each tooth
(of: canines) {
  if
(performing
rotation > 30
degrees) //
Repeated for
each single
tooth
independently
    postpone
movement(direct
ion: rotation);
  put
attachment(teet
h: mesial,
type:
optimized);
}
for each
quadrant (of:
{upper left,
upper right}) {
... }
for each jaw {
  if
(performing
intrusion(teeth
: anteriors) >
0.5mm) {
    put
attachment(on:
canine, type:
CRT, size: 3mm,
direction:
horizontal,
min_distance_fr
om_occlusal:
1mm);
    put
attachment(on:
1st premolar,
type: CRT,
size: 3mm,
direction:
horizontal,
min_distance_fr
om_occlusal:
1mm);
  }
}
```

FIG 10(v)

| | | |
|---|---|---|
| Reuse existing protocol | Include the full content of a protocol, using the keywords "use protocol" followed by the name of a protocol | `use protocol Galler; use protocol Yau;` |
| Comments | Anything after "//" is a comment | `// Tooth movements // No Passive Aligners // Preserve smile line` |
| Whitespace and newlines | Whitespaces separate between successive words. Otherwise, all whitespaces and newlines are ignored. | `limit ipr (teeth: anteriors, max_amount: 0.30 mm) ; limit ipr(teeth;anteriors,max_amount:0.30mm); limit ipr ( teeth : anteriors , max_amount ; 0.30 mm ) ;` |

FIG 10(vi)

```
public protocol DrRoman {
    // IDS Preferences migrated to the protocol
    set dual_arch_treatment_strategy (start: simultaneous, finish: any);
    allow pontics;
    allow passive_aligners;
    set arch_expansion (based_on: any_teeth, limit_per_quadrant: 2mm);
    set leveling_strategy(level_by: incisal_edges, laterals_to_centrals:
0.5mm);
    if (initially bolton_discrepancy > 0 mm) {
        limit ipr(teeth: upper, max_amount: 0 mm);
    }
    set trimming_strategy(trim_line: match_cej);
    disable virtual_c_chain;
    set oa_instead_of_precision_cut;

if (product is Full or product is Teen) {
        disable pontics(teeth: molars);
    }
    ...
}
```

FIG. 11

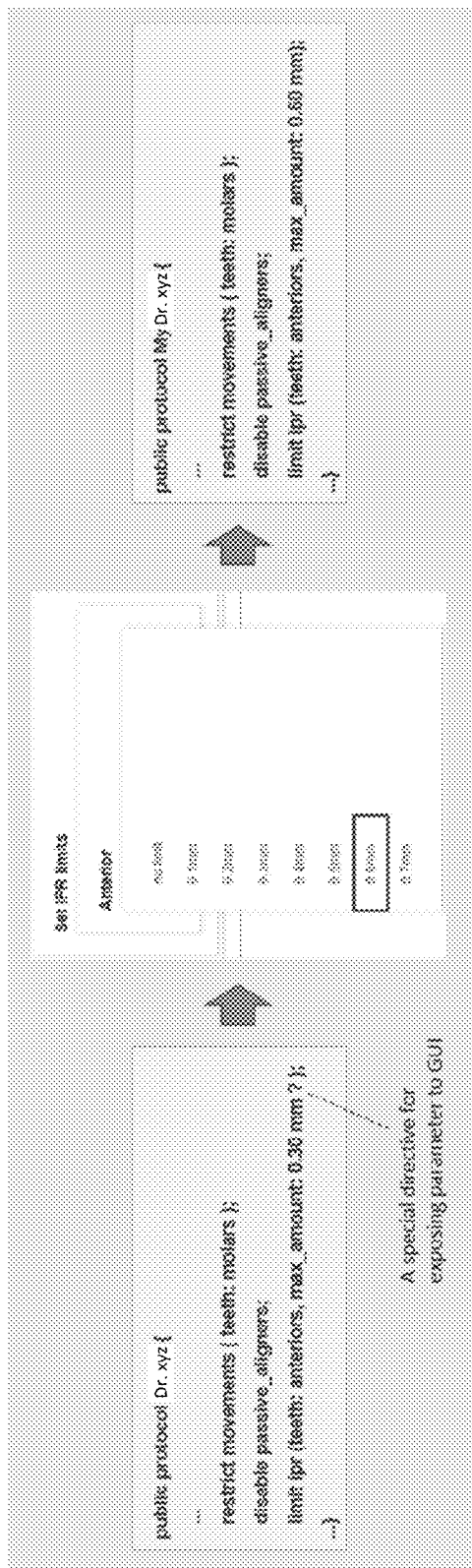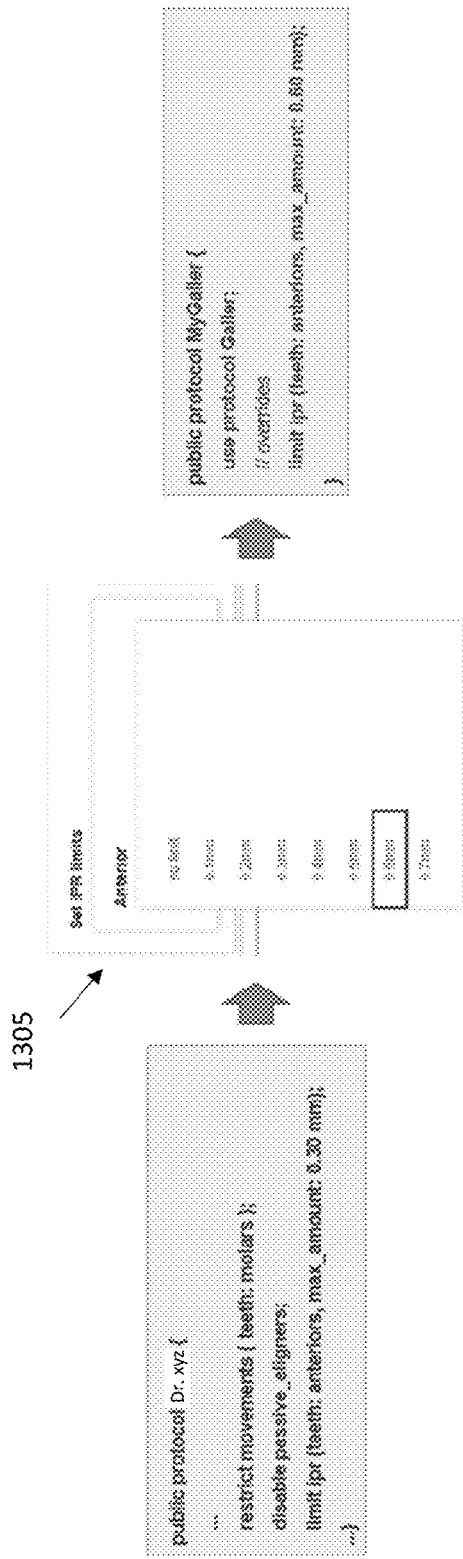
FIG. 13A
FIG. 13B

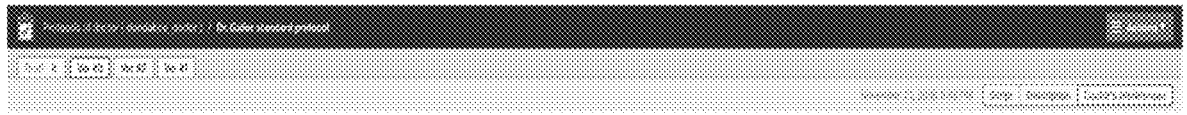

Protocols of doctor (standalone_doctor)

| Preference Case | Value | Percentage |
|---|---|---|
| Doctor prefers to remove attachments at this number of stage till overcorrection: | 2<br>0 | 42%<br>56% |
| Doctor prefers to perform extraction at this stage: | 0<br><copy IPL> | 82%<br>57% |
| Doctor prefers to remove attachment at this number of stage till the treatment end: | 3<br>0 | 5%<br>35% |
| Doctor prefers to put attachments from the stage: | 1 | 100% |
| Doctor prefers to limit IPR amount for any segment with the following values: | 0.2<br>0.3 | 43%<br>37% |
| StartPrecisionCutStage | 1 | 100% |
| Doctor uses Power Ridges: | 0<br>1 | 37%<br>63% |
| Doctor prefers to limit IPR amount for upper jaw with the following values: | 0.3<br>0.2 | 38%<br>43% |

Doctor's validation cases

Mild Crowding Treat Category:

Available Cases:

| Case #1 | Copy Link |
|---|---|
| Case #2 | Copy Link |
| Case #3 | Copy Link |

Top 10 Case instructions
10 the most frequent text instructions from Ccmod

| Value | Percentage |
|---|---|
| "IPR prn Bolton Analysis" | 4% |
| "set ob at 0%" | 4% |
| "IPR as per Bolton Analysis" | 3% |
| "g5 protocol set ob at 0%" | 3% |
| "class ii elastics" | 2% |
| "align upper and lower" | 2% |
| "g5 deep bite protocol" | 2% |
| "g5 protocol" | 2% |
| "bite ramps" | 2% |
| "complete upper and lower alignment" | 2% |

Top 10 CC mod instructions
10 the most frequent text instructions from Ccmod

| Value | Percentage |
|---|---|
| "leave as is" | 61% |
| "fix for me" | 18% |
| "add bite ramps" | 4% |
| "have a great day!" | 1% |
| "place gingival beveld attachment on #19 and 30" | 1% |
| "add gingival beveled attachment on #19 and 30" | 1% |
| "bd amy" | 2% |

Last 3 special preference instructions

| Preference of July 22, 2018 |
|---|
| Preference of Aug 22, 2017 |

-Please provide 2 upper and lower passive aligners without attachments on precision cuts at the end of treatment stages to allow time for Vivera to arrive
-Optimized attachments are preferred
Conventional attachments are beveled rectangular (unless optimized) & end 2+mm from gingiva
-Extrusion: Create interproximal space and then ensure extrusion occurs with retraction.
-Rotation: Ensure visible space and no collision during rotation
-All trays should start and end at same time
-If attachments are not placed at the same time, please have at least 4 tray separations (do not bond attachments on same teeth at tray 2 and then add more on the next tray)
-Please ensure that all beveled attachments do not have undercuts
-Ensure zero collisions (visible space during rotation correction, etc.)
-If refinement scan contains attachments, please maintain them Completed > Compute treatment ** Gallery of cases

FIG. 27

SYSTEMS AND METHODS OF MANAGING CUSTOMIZED RUN DISPLAY ELEMENTS WITH TREATMENT TEMPLATES BASED ON TREATMENT DOMAIN-SPECIFIC PROTOCOLS

CROSS REFERENCE TO RELATED APPLICATIONS

This patent application claims priority to U.S. Provisional Patent Application No. 62/664,684, filed Apr. 30, 2018 and titled "SYSTEMS AND METHODS FOR ORTHODONTIC TREATMENT USING A DOMAIN-SPECIFIC ORTHODONTIC TREATMENT LANGUAGE," which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The technical field relates to treatment planning using domain-specific computer systems and methods, and more particularly to domain-specific computer systems and methods used for treatment planning, such as medical (e.g., dental, orthodontic, etc.) treatment planning.

BACKGROUND

Treatment planning may be used in any medical procedure to help guide a desired outcome. For example, treatment planning may be used in orthodontic and dental treatments using a series of patient-removable appliances (e.g., orthodontic aligners, palatal expanders, etc.) are very useful for treating patients, and in particular for treating malocclusions. Treatment planning is typically performed in conjunction with the dental professional (e.g., dentist, orthodontist, dental technician, etc.), by generating a model of the patient's teeth in a final configuration and then breaking the treatment plan into a number of intermediate stages (steps) corresponding to individual appliances that are worn sequentially. This process may be interactive, adjusting the staging and in some cases the final target position, based on constraints on the movement of the teeth and the dental professional's preferences.

This treatment planning process may include many manual steps that are complex and may require a high level of knowledge of orthodontic norms. Further, because the steps are performed in series, the process may require a substantial amount of time. Manual steps may include preparation of the model for digital planning, reviewing and modifying proposed treatment plans (including staging) and aligner features placement (which includes features placed either on a tooth or on an aligner itself). These steps may be performed before providing an initial treatment plan to a dental professional, who may then modify the plan further and send it back for additional processing to adjust the treatment plan, repeating (iterating) this process until a final treatment protocol is completed and then provided to the patient.

Existing systems and methods for treatment planning may be time consuming, and may provide only limited choices and control to the dental professional.

SUMMARY OF THE DISCLOSURE

Described herein are system, methods and/or computer-readable media for planning a treatment for a patient. These treatment plans may include, but are not limited to, orthodontic treatment plans, such as treatment plan including one or more of: a shell aligner, a palatal expander, etc. These system, methods and/or computer-readable media described herein provide technical solutions to the highly technical problems of treatment planning, including medical treatment planning (e.g., dental treatment planning, orthodontic treatment planning, surgical treatment planning, orthotic treatment planning, etc.). Generally, these methods may include using a domain-specific treatment language to encode user (e.g., physician, therapist, dentist, orthodontist, etc.) preferences as part of a treatment template (also referred to as a treatment protocol). The treatment template, in the domain-specific treatment language, may be read manually (e.g., by the user, technician, etc.) and is also machine readable and parsed by a processor into a set of treatment planning instructions that may applied by a treatment planning engine to one or more patient cases. The treatment planning engine may use the treatment planning instructions, along information about the patient (e.g., the patient's oral cavity, such as a scan of the patient's teeth or other relevant body regions) to automatically generate one or more treatment plans specific to the patient. Because the treatment plan(s) is/are generated using the treatment planning instructions derived from a user's customized treatment template, the resulting treatment plan(s) may also be customized to the user. The resulting treatment plans may be reviewed and approved by the user.

For example, the systems, methods, and/or computer-readable media described herein provide technical solutions to the highly technical problems of orthodontic treatment planning, and may include using a domain-specific orthodontic treatment language to encode user (e.g., dentist, orthodontist, dental technician, etc.) preferences as part of a treatment template. The treatment template, in the domain-specific orthodontic treatment language, may be read manually (e.g., by the user, technician, etc.) and may also be machine readable and parsed by a processor into a set of treatment planning instructions that may applied by a treatment planning engine to one or more patient cases. The orthodontic treatment planning engine may use the treatment planning instructions, along information about the patient's oral cavity (such as a scan of the patient's teeth) to automatically generate one or more treatment plans specific to the patient. Because the treatment plan(s) is/are generated using the treatment planning instructions derived from a user's customized treatment template, the resulting treatment plan(s) may also be customized to the user. The resulting treatment plans may be reviewed and approved by the user.

A treatment plan may refer to a series of steps, devices and/or schedules for altering a subject's physiology to achieve or approach a desired outcome. In some cases the treatment plan is an orthodontic treatment plan and may refer to a series of steps, devices and/or schedules for altering a subject's dental arch to achieve or approach a desired outcome. For convenience, in the examples described herein the orthodontic and/or dental treatment plans may be referred to as "orthodontic treatment plans," or simply "treatment plans," although it should be understood that other types of treatment plans may be included, such as surgical treatment plans, orthotic treatment plans, and the like.

An orthodontic treatment plan may identify one or more dental appliance (including dental aligners) that may be used to alter the subject's dental arch. The orthodontic treatment plan may also or alternatively include steps for modifying the subject's dental arch, both with and/or without one or more dental appliances. In some variations the orthodontic treatment plan may include preparing the subject's dental arch (e.g., by extracting, shaping, trimming, or otherwise altering one or more of the subject's teeth). The orthodontic treatment plan may indicate movement (and/or non-movement) of one or more of the patient's teeth, including indicating the timing or sequencing of movements (start, duration, finishing). An orthodontic treatment plan may include steps for designing and/or fabricating one or more (including an ordered series) of dental appliances. An orthodontic treatment plan may include a schedule of dental appliances indicating the timing for wearing the one or more dental appliances.

A treatment template (e.g., a treatment protocol) for planning an orthodontic treatment may refer to a description of user's (e.g., orthodontist's, dentist's, doctor's, dental technician's, etc.) general and/or specific preferences for a type or category of dental treatment(s). Preferences may include, for example, tooth movement restrictions (e.g., indicating which teeth should not move as part of the treatment), if interproximal reduction (IPR) should be used, and/or how, when during treatment or where to perform IPR, if attachments should be used, where (e.g., on which teeth) attachments should be placed if used, changing spacing distance between teeth, extraction, leveling strategy (e.g., "align by incisal edge" or "align by gingiva margins"), etc. The treatment template may indicate any appropriate number of preferences, including one or more. Preferences may be categorical, and/or conditional (e.g., preferences that depend on one or more other conditions). Treatment templates may also be referred to as treatment protocols.

Any of the treatment templates described herein may be expressed in a domain-specific orthodontic treatment language. A domain-specific orthodontic treatment language is a specialized to the particular orthodontic application domain, and includes a formal grammar specific to the orthodontic treatment, including semantics for conditional statements as well as predefined referents to orthodontic terms (e.g., names of teeth, orthodontic procedures, anatomical referents, etc.). The domain-specific orthodontic treatment language may include clinical setting expressed in verb/noun and optional arguments of dental treatment phases, conditional statements referring to tooth position and/or orthodontic conditions, references to one or more tooth by tooth type, and/or an indication of ordering sequences. The domain-specific treatment orthodontic treatment language is therefore both human readable, as it may directly reference tooth, tooth position and/or tooth movement by name, and machine readable. Specifically, the domain-specific orthodontic treatment language may be parsed by a processor into treatment planning instructions that can be executed by one or more treatment planning engines.

Treatment planning instructions may include rules for planning an orthodontic treatment expressed in a machine-readable form. For example, treatment planning instructions may be parsed from the domain-specific treatment orthodontic treatment language into a data-interchange format, such as a text-only data-interchange format, e.g., JSON. Orthodontic treatment planning instructions may include rules for final positioning of teeth, staging, attachment and dental appliance features, etc. One or more orthodontic treatment planning engines may execute the orthodontic treatment planning instructions. As used herein, the instructions may include all or some of the information from a treatment template, but may also include additional information, including information generic to many treatment plans. This additional information may be combined with the treatment template (e.g., parsed form the domain-specific treatment language).

An orthodontic treatment planning engine may refer to a software, hardware, and/or firmware (or some combination of these) that receives the treatment planning instructions and/or patient information (e.g., a digital model of the patient's teeth), and may apply the orthodontic treatment planning instructions to the patient information to generate one or more orthodontic treatment plans. Any appropriate digital model of a patient's teeth may be used, including a 3D volumetric scan, such as a scan from an intraoral scanner.

For example, described herein are methods of generating an orthodontic treatment plan for an orthodontic treatment. Any of these methods may include: receiving, in a system having one or more processors, a treatment template for planning an orthodontic treatment, wherein the treatment template is expressed in a domain-specific orthodontic treatment language; and parsing, by the one or more processors, the selected treatment template into orthodontic treatment planning instructions that are executable by one or more orthodontic treatment planning engines; and executing, by the one or more orthodontic treatment planning engines, the orthodontic treatment planning instructions to generate one or more orthodontic treatment plans for a digital model of a patient's teeth.

Executing the orthodontic treatment planning instructions may include generating one or more orthodontic treatment plans comprising a sequence of orthodontic appliances (e.g., orthodontic aligners, palatal expanders, etc.) configured to be worn by the patient in a predetermined order. The orthodontic treatment plan may also include instructions for modifying the teeth before/during wearing of the orthodontic appliances (e.g., interproximal reduction, applying attachments, etc.).

Parsing the selected treatment template may comprise converting the selected treatment template into a data-interchange format, including a text-only data-interchange format, such as JSON. The treatment template may be parsed before, during or after transmitting to the orthodontic treatment planning engine(s).

Receiving a treatment template for planning an orthodontic treatment may include requesting selection of the treatment template from a library of treatment templates from a user. A user interface may be provided for selecting the treatment template from the library. For example, any of these methods may include displaying the treatment template selected to the user and allowing the user to modify the orthodontic treatment planning language (e.g., the domain-specific orthodontic treatment language) in the treatment template. Modifying the template may include presenting a graphical user interface (GUI) to the user, wherein the GUI receives user-selected parameters that modify the treatment template.

The domain-specific orthodontic domain-specific orthodontic treatment language may include one or more directives to create one or more graphical user interfaces (GUI) to acquire a user's preference information. Thus, a treatment template (in the domain-specific orthodontic treatment language) may prompt the user or a technician working with the user to modify or provide additional preference information that may be included in the treatment template and/or the orthodontic treatment planning instructions.

In any of the methods and systems described herein a record or log (e.g., a log trace) may be generated while generating and/or modifying the treatment template and/or while parsing the treatment template into orthodontic treatment planning instructions, and/or executing the orthodontic treatment planning instructions to generate the one or more orthodontic treatment plans. The log may record the orthodontic treatment planning instructions, the settings used, the patient information used, and any other parameter that may aid in troubleshooting. For example, any of these methods may include (e.g., as a separate step or as part of the step of executing the orthodontic treatment planning instructions), generating a log trace of the execution of the treatment template.

The domain-specific orthodontic treatment language may include: verb and noun statements of dental treatment phases, conditional statements referencing tooth position, references to one or more tooth by tooth type, and indication of tooth ordering sequences. The conditional statements referencing tooth position may include if and for looping statements.

In another variation, a method of generating An orthodontic treatment plan for an orthodontic treatment may include: receiving, in a system having one or more processors, a treatment template for planning an orthodontic treatment, wherein the treatment template is expressed in a domain-specific orthodontic treatment language that includes: verb and noun statements of dental treatment phases, conditional statements referencing tooth position, references to one or more tooth by tooth type, and indication of tooth ordering sequences; and parsing, by one or more processors, the selected treatment template into orthodontic treatment planning instructions that are executable by one or more orthodontic treatment planning engines; and executing, by the one or more orthodontic treatment planning engines, the orthodontic treatment planning instructions to generate one or more orthodontic treatment plans for a digital model of a patient's teeth comprising a sequence of orthodontic aligners configured to be worn by the patient in a predetermined order.

Also described herein are systems that may perform any of the methods described herein. For example, a system, including systems for generating An orthodontic treatment plan for an orthodontic treatment may include: one or more processors; and one or more storage media coupled to the one or more processors and storing instructions that, when executed by the one or more processors, performs a computer-implemented method comprising: receiving, in the one or more processors, a treatment template for planning an orthodontic treatment, wherein the treatment template is expressed in a domain-specific orthodontic treatment language; and parsing, by the one or more processors, the selected treatment template into orthodontic treatment planning instructions that are executable by the one or more orthodontic treatment planning engines; and executing, by the one or more orthodontic treatment planning engines, the orthodontic treatment planning instructions to generate one or more orthodontic treatment plans for a digital model of a patient's teeth.

The computer-implemented method may further comprise, as part of executing the orthodontic treatment planning instructions, generating one or more orthodontic treatment plans comprising a sequence of orthodontic aligners configured to be worn by the patient in a predetermined order. The computer-implemented method may further comprises converting the selected treatment template into a data-interchange format.

A computer-implemented method may include, as part of receiving the treatment template, requesting selection of the treatment template from a library of treatment templates from a user, and/or requesting selection of the treatment template from a library of treatment templates from a user and displaying the treatment template selected to the user and allowing the user to modify the treatment template.

Any of these systems may include, generating a log trace of the application of the treatment template.

For example, a system may include: one or more processors; and one or more storage media coupled to the one or more processors and storing instructions that, when executed by the one or more processors, performs a computer-implemented method comprising: receiving, in one or more processors, a treatment template for planning an orthodontic treatment, wherein the treatment template is expressed in a domain-specific orthodontic treatment language that includes: verb and noun statements of dental treatment phases, conditional statements referencing tooth position, references to one or more tooth by tooth type, and indication of tooth ordering sequences; and parsing, by one or more processors, the selected treatment template into orthodontic treatment planning instructions that are executable by one or more orthodontic treatment planning engines; and executing, by the one or more orthodontic treatment planning engines, the orthodontic treatment planning instructions to generate one or more orthodontic treatment plans specific to a digital model of a patient's teeth comprising a sequence of orthodontic aligners configured to be worn by the patient in a predetermined order.

Also described herein are methods of creating a treatment template for an orthodontic treatment. For example, a method of creating a treatment template for an orthodontic treatment, the method comprising: gathering a dental professional's treatment preferences for two or more of: final positioning of the teeth, staging of movement of the teeth, attachments on the teeth, conditional operations for treating a patient based on an initial position of the patient's teeth, conditional operations for treating the patient based a final position of the patient's teeth, conditional operations for treating the patient based on the presence of a clinical condition; and scripting the dental professional's preferences in a domain-specific orthodontic treatment language to form a treatment template, wherein the domain-specific orthodontic treatment language includes: verb and noun statements of dental treatment phases, conditional statements referencing tooth position, references to one or more tooth by tooth type, and indication of tooth ordering sequences, further wherein the treatment template is both human-readable and machine readable and configured to be parsed by one or more processors to generate An orthodontic treatment plan into orthodontic treatment planning instructions that are executable by one or more orthodontic treatment planning engines.

The methods of creating a treatment template for an orthodontic treatment may be included as part of a method of generating an orthodontic treatment plan for an orthodontic treatment, or may be separate.

In any of these methods, the treatment template may be tested by parsing the treatment template into the orthodontic treatment planning instructions and executing, using the one or more orthodontic treatment planning engines, the orthodontic treatment planning instructions and a control digital model of the teeth to generate one or more orthodontic treatment plans comprising a sequence of orthodontic aligners configured to be worn by the patient in a predetermined order.

Any of these methods may also include storing the treatment template in a library of treatment templates.

Any of these methods may also or alternatively include parsing, by the one or more processors, the selected treatment template into orthodontic treatment planning instructions that are executable by one or more orthodontic treatment planning engines, and/or executing, using the one or more orthodontic treatment planning engines, the orthodontic treatment planning instructions for a digital model of a patient's teeth to generate one or more orthodontic treatment plans comprising a sequence of orthodontic aligners configured to be worn by the patient in a predetermined order.

The methods may also include displaying the treatment template and allowing a user to modify the orthodontic treatment planning language in the treatment template. For example, scripting may include presenting a graphical user interface (GUI) to the user, wherein the GUI receives user-selected parameters that modify the treatment template.

Gathering may include gathering the dental professional's treatment preferences for two or more of (e.g., three or more of, four or more of, etc.): final positioning of the teeth, staging of movement of the teeth, attachments on the teeth, conditional operations for treating the patient based on the initial position of the patient's teeth, conditional operations for treating the patient based the final position of the patient's teeth, and conditional operations for treating the patient based on the presence of the clinical condition. For example, gathering may include receiving the dental professional's treatment preferences for each of: final positioning of the teeth, staging of movement of the teeth, attachments on the teeth, conditional operations for treating the patient based on the initial position of the patient's teeth, conditional operations for treating the patient based the final position of the patient's teeth, and conditional operations for treating the patient based on the presence of the clinical condition.

A method of generating An orthodontic treatment plan for an orthodontic treatment may include: accessing, by one or more processors a treatment template, wherein the treatment template comprises a set of orthodontic treatment preferences expressed in a domain-specific orthodontic treatment language that includes: verb and noun statements of dental treatment phases, conditional statements referencing tooth position, references to one or more tooth by tooth type, and indication of tooth ordering sequences; identifying by one or more processors, rules for movement of a teeth during the orthodontic treatment; and translating the rules into a set of orthodontic treatment planning instructions in a data-interchange format that may be executed by one or more orthodontic treatment planning engines to generate one or more orthodontic treatment plans from a digital model of teeth.

Any of these methods may also include executing, using the one or more orthodontic treatment planning engines, the orthodontic treatment planning instructions and a digital model of a patient's teeth to generate one or more orthodontic treatment plans comprising a sequence of orthodontic aligners configured to be worn by the patient in a predetermined order.

A system may include: one or more processors; and one or more storage media coupled to the one or more processors and storing instructions that, when executed by the one or more processors, performs a computer-implemented method comprising: accessing, by one or more processors a treatment template, wherein the treatment template comprises a set of orthodontic treatment preferences expressed in a domain-specific orthodontic treatment language that includes: verb and noun statements of dental treatment phases, conditional statements referencing tooth position, references to one or more tooth by tooth type, and indication of tooth ordering sequences; identifying by one or more processors, rules for movement of a teeth during the orthodontic treatment; and translating the rules into a set of orthodontic treatment planning instructions in a data-interchange format that may be executed by one or more orthodontic treatment planning engines to generate one or more orthodontic treatment plans from a digital model of teeth.

In general, described herein are method of planning a treatment for a patient. As mentioned above, these treatment planning methods may be medical treatment plans, such as treatment plans for performing one or more surgical procedures, and particular surgical procedures having multiple steps. In some variations these medical and/or surgical steps may be performed by a robotic tool; all or some stages of the treatment may include one or more robotic manipulations (movements, application of energy, etc.), which may be planned by the treatment plan. A digital model of the patient's anatomy may be used to design the surgical procedure. In some variations these medical and/or surgical steps may correspond to the use of an orthotic (e.g., brace, prosthetic, etc.). For example, the treatment plans described herein may relate to treatment plans for modifying a subject's posture, gait, or musculoskeletal system. As already described above, the treatment plans described herein may also relate to one or more dental procedures, including but not limited to orthodontic procedures, such as the use of a series of dental aligners (e.g., shell aligners) to move and/or reposition the teeth.

For example, described herein are methods for planning a treatment of a patient that include receiving, from a user, a selected treatment protocol for treating the patient from a list of treatment protocols, wherein the treatment protocols in the list of treatment protocols are customized to the user based on previous user cases; presenting, to the user, a display showing the selected treatment protocol as applied to one or more sample patients; receiving proposed modifications to the treatment protocol from the user; converting the proposed modifications to the treatment protocol into a set of modification instructions in a domain-specific treatment language; modifying the selected treatment protocol based on the set of modification instructions in the domain-specific treatment language to form a final treatment protocol; and providing the treatment plan to the user based on the final treatment protocol (e.g., by applying the final treatment protocol to a digital representation of the patient's teeth).

In general, a treatment protocol may refer to a set of instructions that may be used to generate a treatment plan by applying the final treatment protocol to a patient (e.g., a subject). The methods and apparatuses (systems) described herein may be used to generate treatment protocols that may be used to generate a treatment plan.

Any of these methods and apparatuses (e.g., systems) that may perform them may also include applying the final treatment protocol to a digital representation of the patient's teeth and generating one or more treatment appliances (e.g., orthodontic appliances such as aligners, palatal expanders, etc.) based on this treatment plan. For example the one or more treatment appliances may comprise dental appliances such as orthodontic appliances.

Any of these methods and apparatuses (e.g., systems) that may perform them may further include initially requesting, by the user, a plan for treating the patient. The user may request, using a user interface, a treatment plan (such an orthodontic treatment plan from a system, including one or more processors, performing the method as described herein.

Any of these methods and apparatuses (e.g., systems) that may perform them may include receiving a selection of one or more sample patients and applying the selected treatment protocol to the selected one or more sample patients. For example, the user (doctor, dentist, orthodontist, etc.) may be presented with a listing of sample patients and may select, via a user interface, from among the sample patients; alternatively a technician separate from the user may select one or more of the sample patients. Alternatively, the system may automatically select from one or more sample patients.

Presenting, to the user, the display showing the selected treatment protocol as applied to one or more sample patients may include showing a plurality of treatment stages showing the effect of the selected treatment protocol on the one or more sample patients at different time points. When generating the orthodontic treatment plans, the user may be presented, via a display and/or user interface, a graphical image (e.g., a digital representation or model) of the sample patient's dentition, showing the position of the teeth at the final stage and/or one or more other stages of the treatment plan. In some variations the user may, via a user interface, scan through or review a plurality of the treatment sages showing the modeled tooth position at each stage. In some variations, the user may be presented with an animation showing the change in the patient's dentition over time during the course of the treatment plan. The user interface may allow the user to adjust the view (zoom in/out, remove some/all of the teeth, remove/show features of the treatment plan) of the teeth across the one or more displays.

In any of these methods and apparatuses (e.g., systems) that may perform them, the method or apparatus (e.g., system) may use a digital model of the patient's teeth to project the effect of the treatment protocol instead of or in addition to the listing of sample patients. Thus at any step of process in which a sample patient is used, the patient may correspond to the patient. For example in some variations the method may include receiving a digital model of the patient's teeth (e.g., from the user).

The steps of generating the treatment protocol may be iteratively repeated in any of these methods and apparatuses (e.g., systems) that may perform them. For example, the method may include iteratively repeating the steps of: presenting the selected treatment protocol as applied to the one or more sample patients, receiving proposed modifications to the treatment protocol, converting the proposed modifications, and modifying the selected treatment protocol. These steps may be repeated (iterated) until the user approves of the final treatment protocol.

In any of these methods and apparatuses (e.g., systems) that may perform them, presenting the display showing the selected treatment protocol as applied to one or more sample patients to the user may include applying the treatment protocol to one or more digital models of the one or more sample patients' teeth from a library of sample patients' teeth.

Any of these methods or apparatuses capable of performing them may include creating a user-specific treatment plan customized to the user based on previous user cases and included in the list of treatment protocols. The user-specific treatment protocols may be created by, for example: analyzing the user's preferences from previously treated patients; applying the user's preferences and received instructions (provided by the user, e.g., as part of a request for a treatment plan) to generate the user-specific treatment protocol in the domain-specific treatment language. In some cases this may also include validating the new treatment protocol against one or more sample patients.

For example, a method of planning a treatment for a patient may include: receiving, from a user, a selected treatment protocol for treating the patient's teeth from a list of orthodontic treatment protocols, wherein the treatment protocols in the list of orthodontic treatment protocols are customized to the user based on previous user cases; presenting, to the user, a display showing the selected treatment protocol as applied to the teeth of one or more sample patients from a library of sample patients' teeth; receiving proposed modifications to the treatment protocol from the user; converting the proposed modifications to the treatment protocol into a set of modification instructions in a domain-specific orthodontic treatment language; modifying the selected treatment protocol based on the set of modification instructions in the domain-specific orthodontic treatment language to form a final treatment protocol; and providing a treatment plan to the user based on the final treatment protocol.

Any of these methods or systems capable of performing them may also include applying the final treatment protocol to the patient to generate a treatment plan, and using this treatment plan to generate one or more orthodontic treatment appliances. For example, the one or more orthodontic appliances may comprise one or more aligners (e.g., shell aligners).

As mentioned above, also described herein are systems capable of or configured to perform any of the methods described herein. For example, described herein are systems comprising: one or more processors; and one or more storage media coupled to the one or more processors and storing instructions that, when executed by the one or more processors, performs a computer-implemented method comprising: receiving, from a user, a selected treatment protocol for treating the patient from a list of treatment protocols, wherein the treatment protocols in the list of treatment protocols are customized to the user based on previous user cases; presenting, to the user, a display showing the selected treatment protocol as applied to one or more sample patients; receiving proposed modifications to the treatment protocol from the user; converting the proposed modifications to the treatment protocol into a set of modification instructions in a domain-specific treatment language; modifying the selected treatment protocol based on the set of modification instructions in the domain-specific treatment language to form a final treatment protocol; and providing a treatment plan to the user based on the final treatment protocol.

A system may include: one or more processors; and one or more storage media coupled to the one or more processors and storing instructions that, when executed by the one or more processors, performs a computer-implemented method comprising: receiving, from a user, a selected treatment protocol for treating the patient's teeth from a list of orthodontic treatment protocols, wherein the treatment protocols in the list of orthodontic treatment protocols are customized to the user based on previous user cases; presenting, to the user, a display showing the selected treatment protocol as applied to the teeth of one or more sample patients from a library of sample patients' teeth; receiving proposed modifications to the treatment protocol from the user; converting the proposed modifications to the treatment protocol into a set of modification instructions in a domain-specific orthodontic treatment language; modifying the selected treatment protocol based on the set of modification instructions in the domain-specific orthodontic treatment language to form a final treatment protocol; and providing a treatment plan to the user based on this final treatment protocol.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 5A-5B show an example of a user preference (in this example, posterior cross-bite) that may be written in a domain-specific orthodontic treatment language for a treatment template; in FIG. 5A the default preference is shown as improving posterior cross-bite, while FIG. 5B shows the preference for not improving posterior cross-bite.

FIGS. 6A-6B show an example of a user preference (in this example, bite ramp attachments) that may be written in a domain-specific orthodontic treatment language for a treatment template; in FIG. 6A the default preference is shown as no bite ramps, while FIG. 6B shows the preference for using attachments placed on premolars, with bite ramps for all cases except where there is an open bite and/or rotated laterals.

FIGS. 7A-7B show an example of a user preference (in this example, position of attachments on teeth) that may be written in a domain-specific orthodontic treatment language for a treatment template; in FIG. 7A the default preference is shown as locating attachments in a mid-range of the tooth, while FIG. 7B shows the preference for positioning the attachments close to the gingiva.

FIGS. 8A-8B show an example of a user preference (in this example, target overbite) that may be written in a domain-specific orthodontic treatment language for a treatment template; in FIG. 8A the default preference is shown as not correcting the target overbite, while FIG. 7B shows the preference for correcting the overbite to within a selected target (e.g., between 0.1 mm and 1 mm).

FIGS. 9A-9B show an example of a user preference (in this example, lingual bite ramp attachments) that may be written in a domain-specific orthodontic treatment language for a treatment template; in FIG. 9A the default preference is shown as not including lingual bite ramp attachments for anterior intrusion, while FIG. 9B shows the preference for including lingual bite ramp attachments for the lower anterior intrusion.

FIG. 10(i)-10(vi) is a table illustrating example grammar and diction for a domain-specific orthodontic treatment language.

FIG. 11 is an example of a treatment template in a domain-specific orthodontic treatment language.

FIGS. 13A-13D illustrate examples of user interface for modifying a treatment template.

FIG. 27 is an example user interface illustrating various user preferences.

DETAILED DESCRIPTION

In general, medical treatment planning may allow users to create patient-customized treatment protocols. For example, orthodontic treatment planning allows users to create patient-customized treatment protocols. Such protocols may include rules for final positioning, staging, attachment and aligner features, and may define conditional behaviors depending on the treatment goals, the initial or final position of teeth, or the existence of various clinical conditions. Manual orthodontic treatment planning may be slow and complicated, even when assisted by orthodontic treatment planning algorithms, which typically use simple parameter files. This is particularly true when users require higher degree of customization, which may be accommodated by either applying their protocols manually (which can be labor-intensive and may result in inconsistent results), or by coding special rules in a shared code base (which may result in long validation cycles).

The present disclosure is related to systems, methods, computing device readable media, and devices that solve technical problems related to treatment planning including, in particular, orthodontic treatment planning and/or technical problems related to fabrication of dental appliances (e.g., aligners) as part of an orthodontic treatment plan. Automated agents (including those that use machine learning models) may be used to aid in forming, modifying and processing treatment templates, which may be encoded in a domain-specific orthodontic treatment language. In some implementations, the automated agents described herein provide treatment templates, which may be converted into orthodontic treatment planning instructions, and used with one or more sets of patient data (e.g., scans of a patient's teeth) to generate one or more orthodontic treatment plans. Orthodontic treatment plans may include descriptions or instructions to fabricate dental appliances, such as dental aligners.

Example Structures and Systems

Figure 28:
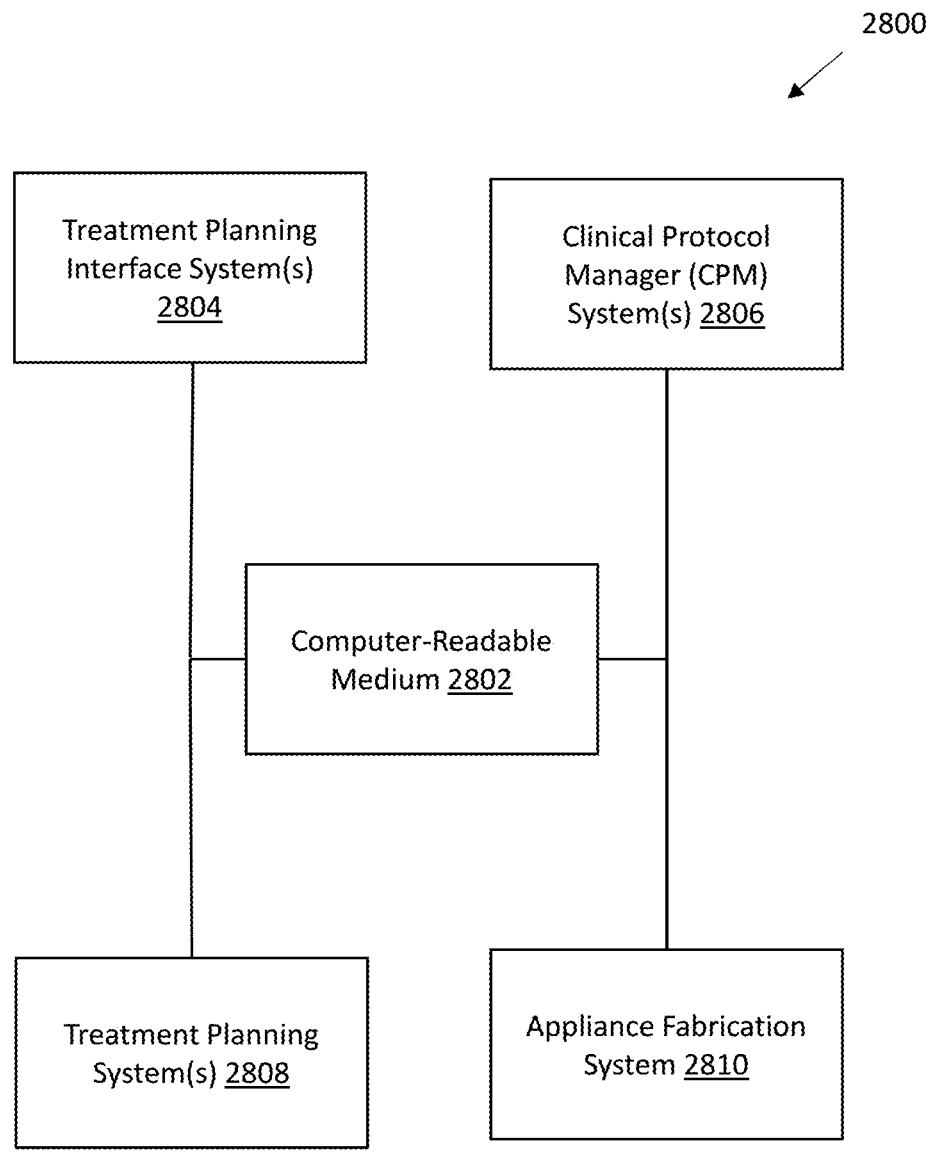
FIG. 28 is a diagram showing an example of systems in a device planning environment.

FIG. 28 is a diagram showing an example of systems in a device planning environment 2800. The device planning environment 2800 includes a computer-readable medium 2802, treatment planning interface system(s) 2804, a clinical protocol manager (CPM) system(s) 2806, treatment planning system(s) 2808, and appliance fabrication system(s) 2810. One or more of the components (including modules) of the orthodontic treatment planning system 2800 may be coupled to one another (e.g., through the example couplings shown in FIG. 2800) or to modules not explicitly shown in FIG. 28. The computer-readable medium 2802 may include any computer-readable medium, including without limitation a bus, a wired network, a wireless network, or some combination thereof.

A computer system can be implemented as an engine, as part of an engine or through multiple engines. As used herein, an engine includes one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, datastores are intended to include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The treatment planning interface system(s) 2804 may include one or more computer systems configured to interact with users and provide users with the ability to manage treatment plans for patients. A "user," in this context, may refer to any individual who can access and/or use the treatment planning interface system(s) 2804, and can include any medical professional, including dentists, orthodontists, podiatrists, medical doctors, surgeons, etc.

In some implementations, the treatment planning interface system(s) 2804 includes engines to gather patient data related to patients who are to be treated according to a treatment plan.

"Patient data," as used herein, may include data related to a patient. Patient data may include representations of anatomical information, such as information about specific portions of the human body to be treated. Examples of anatomical information include representations of a patient's dentition, bones, organs, etc. at a specific time. Patient data may represent anatomical information before, during, or after a treatment plan. As examples, patient data may represent the state and/or intended state of a patient's dentition before, during, or after orthodontic or restorative treatment plans. Patient data may be captured using a variety of techniques, including from a scan, digitized impression, etc. of the patient's anatomy.

A "treatment plan," as used herein, may include a set of instructions to treat a medical condition. A treatment plan may specify, without limitation treatment goals, specific appliances used to implement the goals, milestones to measure progress, and other information, such as treatment length and/or treatment costs. As noted herein, in some implementations, the treatment planning interface system(s) 2804 provides a user with an orthodontic treatment plan to treat malocclusions of teeth. The treatment planning interface system(s) 2804 may also provide users with restorative treatment plans for a patient's dentition and other types of medical treatment plans to address medical conditions patients may have. In some implementations, a treatment plan may include an automated and/or real-time treatment plan, such as the treatment plans described in U.S. patent application Ser. No. 16/178,491, entitled "Automated Treatment Planning," the contents of which are incorporated by reference as if set forth fully herein. A treatment plan may also include treatment instructions provided by a treatment technician, such as a treatment technician who provides the treatment plan to the user of the treatment planning interface system(s) 2804 through the computer-readable medium 2802.

In various implementations, the treatment planning interface system(s) 2804 is configured to allow a user to visualize, interact with, and/or fabricate appliances that implement a treatment plan. As an example, the treatment planning interface system(s) 2804 may provide a user with a user interface that displays virtual representations of orthodontic appliances that move a patient's teeth from an initial position toward a final position to correct malocclusions of teeth. The treatment planning interface system(s) 2804 can similarly display representations of restorative appliances and/or other medical appliances. The treatment planning interface system(s) 2804 may allow a user to modify appliances through a UI supported thereon. In various implementations, the treatment planning interface system(s) 2804 allows a user to fabricate appliances through, e.g., the appliance fabrication system(s) 2810. (It is noted the appliance fabrication system(s) 2810 may but need not be remote to the treatment planning interface system(s) 2804 and can be located proximate to the treatment planning interface system(s) 2804.)

Figure 18:
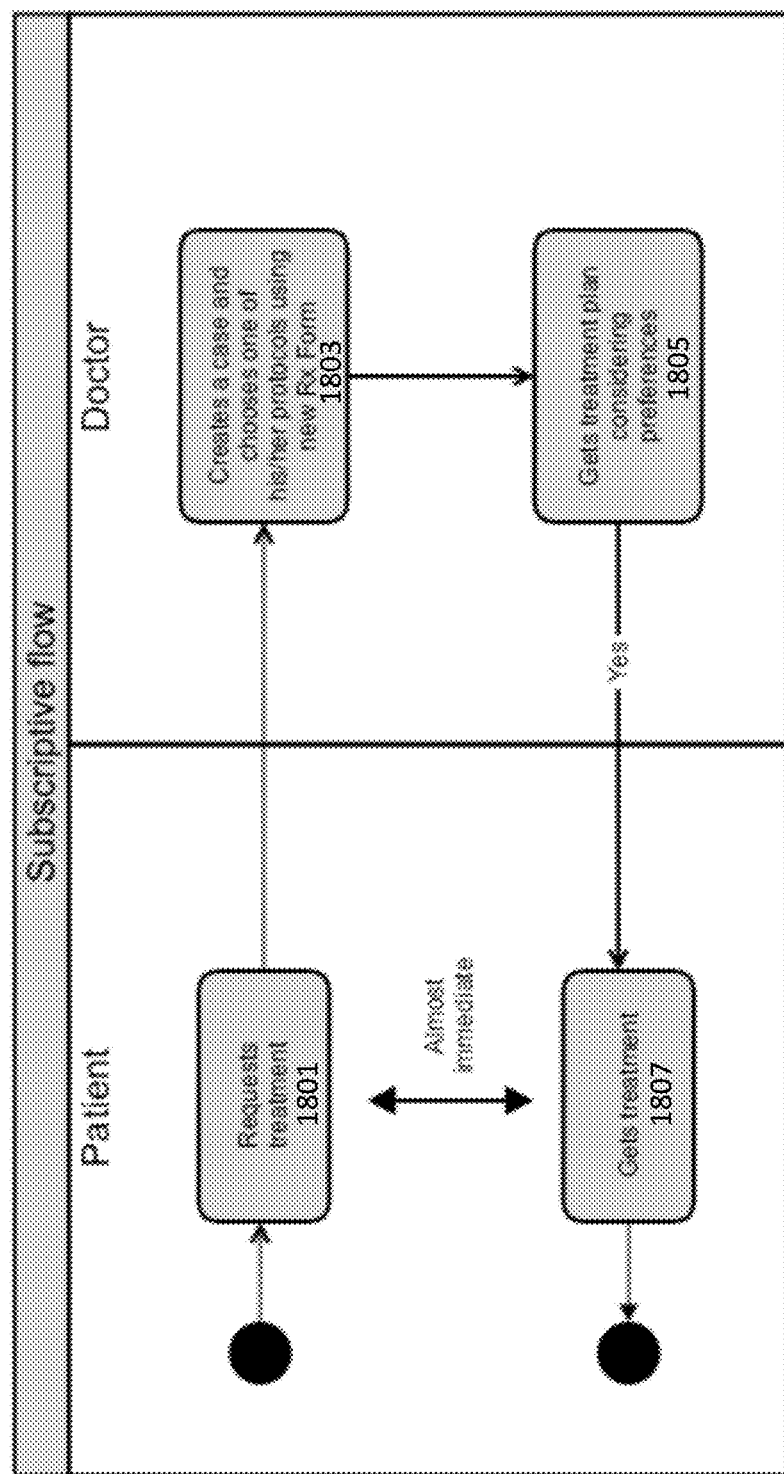
FIG. 18 is a process diagram illustrating a subscriptive flow for a method of using a treatment protocol to generate a treatment plan.

The treatment planning interface system(s) 2804 may be configured to provide a user with UIs that allow the user to discuss treatment plans with patients. As an example, the treatment planning interface system(s) 2804 may display to the user portions of patient data (e.g., depictions of a condition to be treated) as well as treatment options to correct a condition. The treatment planning interface system(s) 2804 may display potential appliances that are prescribed to implement the treatment plan. As an example, the treatment planning interface system(s) 2804 may display to the user a series of orthodontic appliances that are configured to move a patient's dentition from a first position toward a target position in accordance with an orthodontic treatment plan. The treatment planning interface system(s) 2804 may further be configured to depict the effects of specific appliances at various stages of a treatment plan. In some implementations, the treatment planning interface system(s) 2805 may implement a subscriptive flow for a method of using a treatment protocol to generate a treatment plan as shown in FIG. 18.

The treatment planning interface system(s) 2804 may be configured to allow a user to interact with a treatment plan. In some implementations, the treatment planning interface system(s) 2804 allows a user to specify treatment preferences. "Treatment preferences," as used herein, may include specific treatment options and/or treatment tools that a user prefers when treating a condition. Treatment preferences may include clinical settings, treatment goals, appliance attributes, preferred ranges of movement, specific stages to implement a specific procedure, etc. Examples of clinical settings in an orthodontic context include allowing or disallowing a type of treatment, use of various types of movements on specific teeth (e.g., molars), use of specific procedures (e.g., interproximal reduction (IPR)), use of orthodontic attachments on specific teeth, etc. Examples of treatment goals in an orthodontic context include lengths/costs of treatments, specific intended final and/or intermediate positions of teeth, etc. Example ranges of movement in an orthodontic context include specific distances and/or angles teeth are to move over various stages of treatment and/or specific forces to be put on teeth over various stages of treatment. Specific stages to implement a specific procedure include, for instance in the orthodontic context, a specific treatment stage to implement attachments, hooks, bite ramps and/or to perform procedures such as surgery or interproximal reduction.

As discussed further herein, the treatment planning interface system(s) 2804 may be configured to provide users with customized GUI elements based on treatment templates that structure their treatment preferences in a manner that is convenient to them. Customized GUI elements may include forms, text boxes, UI buttons, selectable UI elements, etc.). In some implementations, customized GUI elements may list treatment preferences and provide a user with the ability to accept, deny, and/or modify treatment preferences. Customized GUI elements may provide the ability to accept or deny parts of at treatment plan and/or modify portions of a treatment plan. In some implementations, a user's customized GUI elements provide the ability to modify parts of an appliance recommended for a treatment plan. For instance, a treatment-related UI element may provide the ability to modify force systems, velocities of tooth movement, angles and/or orientations of parts of aligners, crowns, veneers, etc. that are implemented at specific stages of an orthodontic or restorative treatment plan.

"Treatment templates," as used herein, may include structured data expressed in "treatment domain-specific protocols." (In some examples, treatment templates are generated by the CPM system(s) 2608, stored in datastores on the treatment planning system(s) 2808, and parsed by engines on the treatment planning system(s) 2808 that create customized GUI elements on the treatment planning interface system(s) 2804.)

"Treatment domain-specific protocols," as used herein, may include computer languages, runtime objects (e.g., applications, processes, etc.), interpreted items (e.g., executed scripts), etc. that are specialized to treatment planning. Treatment domain-specific protocols may include attributes that are specialized to patient data and/or the gathering thereof, attributes that are specialized to description and/or interaction with treatment plans, and attributes that are specialized to appliances used to implement a treatment plan. The present disclosure provides a detailed example of orthodontic domain-specific protocols. It is noted the examples herein may apply to restorative and/or dental domain-specific protocols and other medical domain-specific protocols.

In some implementations, treatment templates include customized graphical user interface (GUI) elements. Customized GUI elements may be generated using treatment domain-specific protocols. As noted herein, the treatment templates for a user may be customized based on a template library of treatment templates for other users. As an example, a treatment template for a user may be derived from and/or otherwise based on a treatment template of another user (e.g., the treatment preferences in that treatment template may be derived from and/or otherwise based on treatment preferences of another user). Public templates may provide the basis of deriving treatment preferences of other users. Private templates may provide a basis of deriving treatment preferences of a specific user. Additionally, customized GUI elements may be automatically generated during execution of applications and/or processes on the treatment planning interface system(s) 2804. Customized GUI elements may operate to display attributes of treatment plans that are relevant to a specific user.

Figure 19:
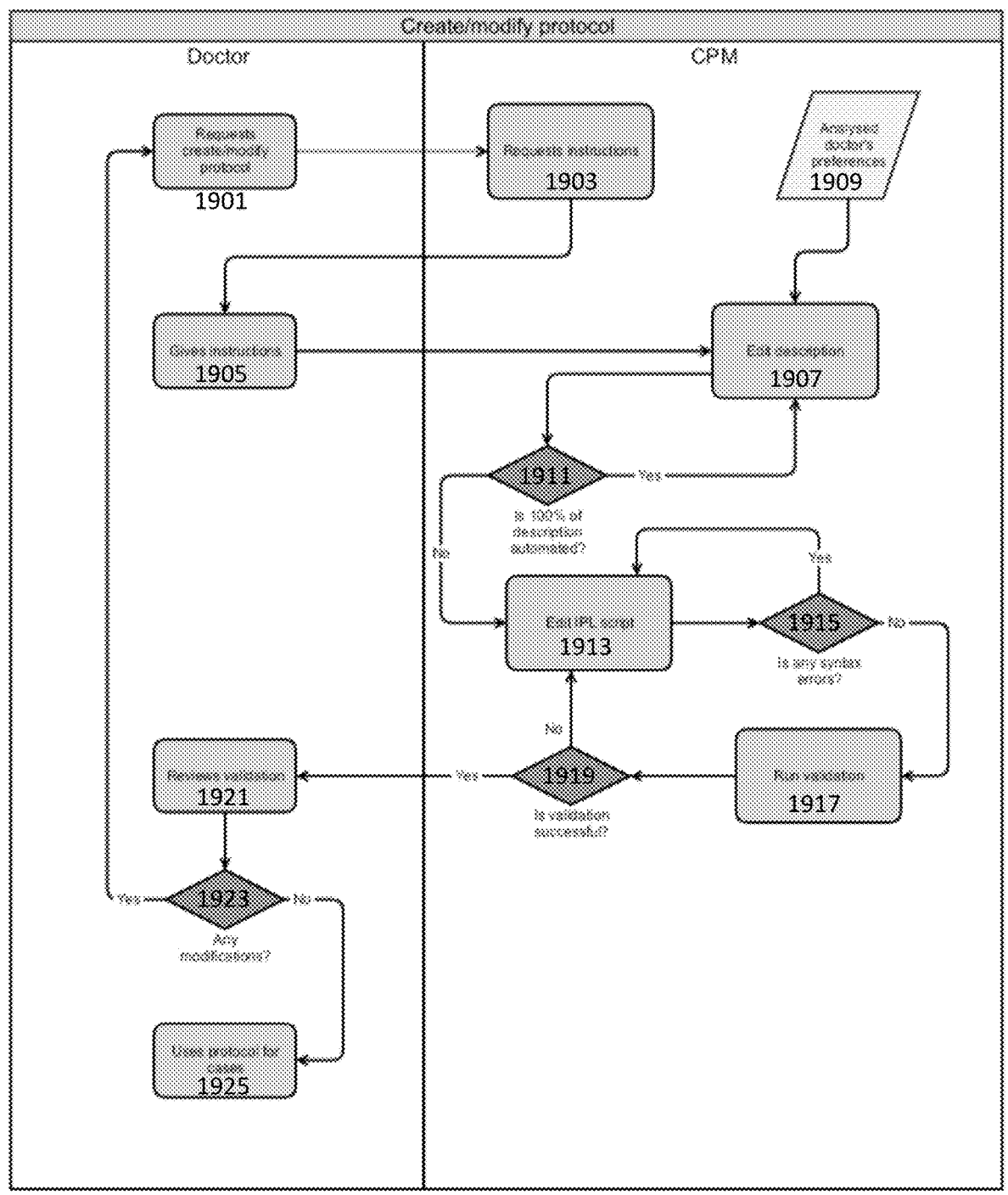
FIG. 19 schematically illustrates a method of creating and/or modifying a user-specific protocol as described herein.
Figure 20:
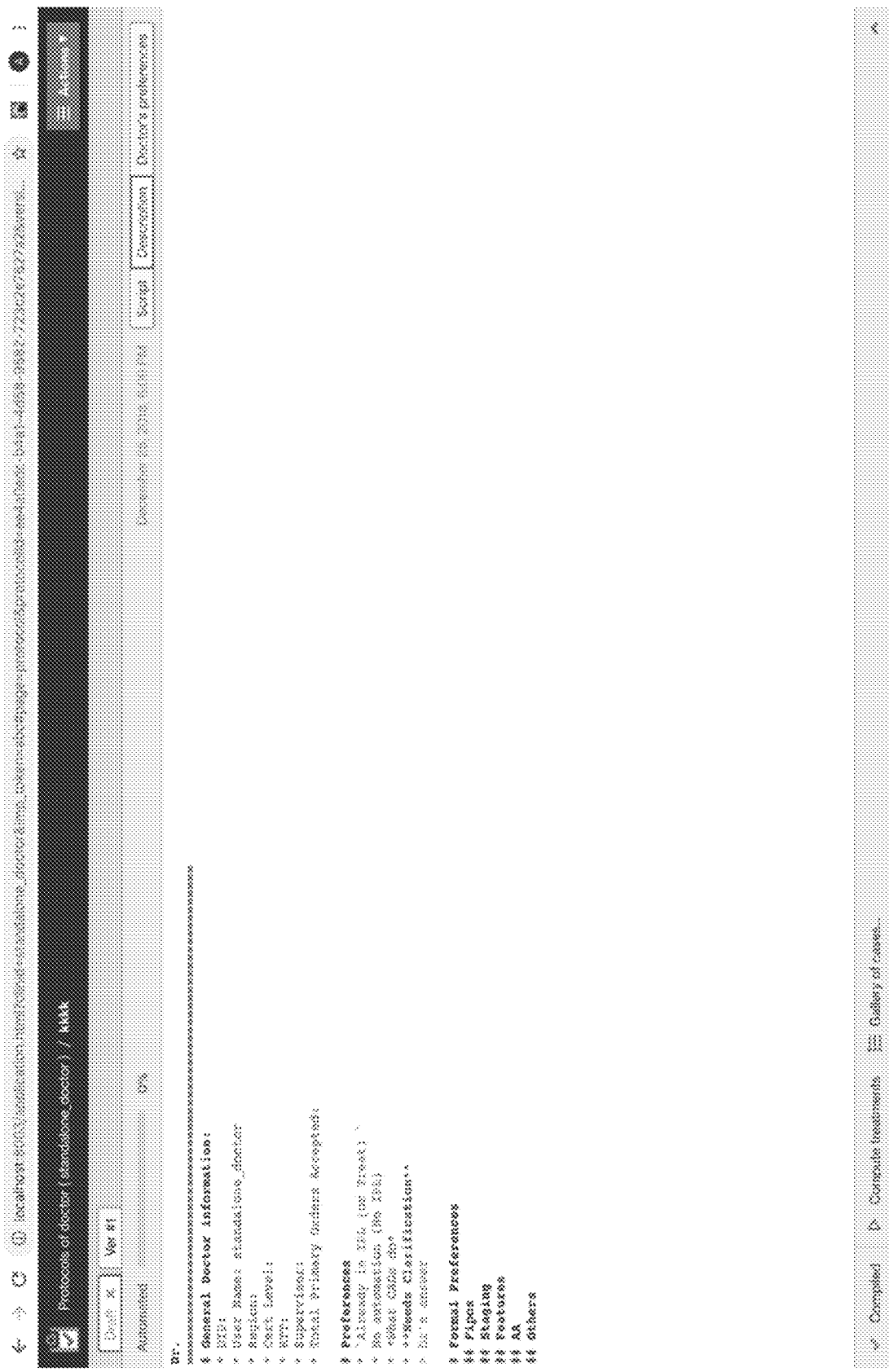
FIG. 20 shows one example of a user interface for a description editor as described herein.
Figure 21:
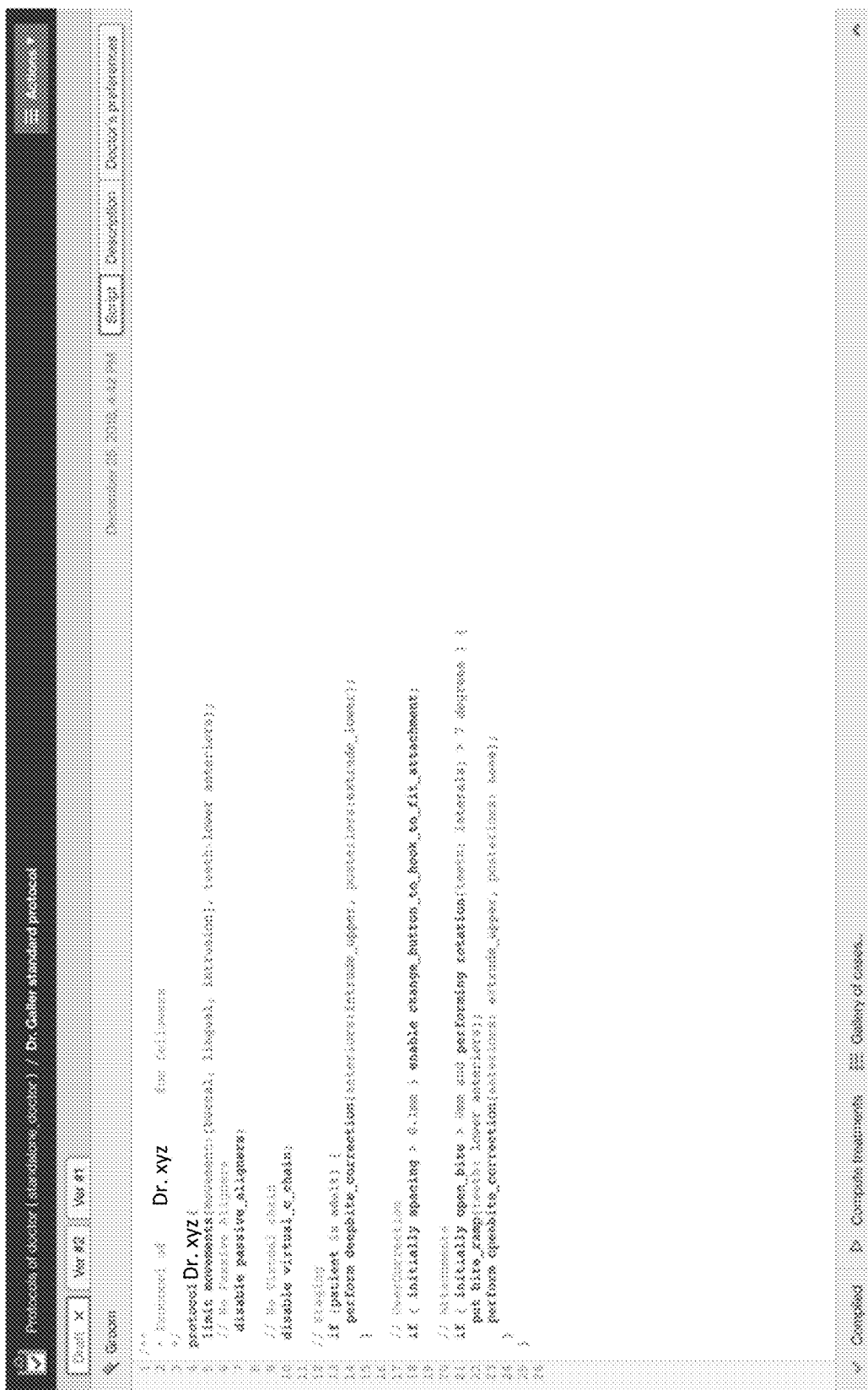
FIG. 21 is an example of one variation of a user interface for a domain-specific orthodontic treatment language editor.

The CPM system(s) 2806 may include one or more computer systems configured to create treatment templates using treatment domain-specific protocols. In some implementations, the CPM system(s) 2806 are operated by CPM technicians, who may, but need not, be remote to users of the treatment planning interface system(s) 2804. The CPM system(s) 2806 may also be operated by automated agents. The CPM system(s) 2806 may include tools to create treatment templates for specific users based on unstructured representations of treatment preferences of those users. In some implementations, the CPM system(s) 2806 are configured to obtain past treatment preferences for users through telephonic interviews, emails, notes memorializing discussions, etc. The CPM system(s) 2806 may provide technicians with editing tools to structure treatment preferences in a manner that can be organized for a treatment domain-specific protocol. In various implementations, the CPM system(s) 2806 are configured to support creating and editing of treatment domain-specific protocols. As an example, the CPM system(s) 2806 may be configured to allow technicians to create and/or edit treatment domain-specific scripts that structure treatment preferences for a specific user. An example flowchart of a method of creating or editing of treatment domain-specific protocols is shown in FIG. 19. Example screen capture of editing tools supported by the CPM system(s) 2806 are shown in FIGS. 20 and 21.

The CPM system(s) 2806 may be configured to provide to a technician sets of treatment domain-specific protocols that have already been created and/or are active for a specific user. In various implementations, the CPM system(s) 2806 allow technicians to create new treatment domain-specific protocols, edit existing treatment domain-specific protocols, and/or take actions on existing treatment domain-specific protocols. FIGS. 22-25 show example screen captures of creating, editing, and/or taking actions on treatment domain-specific protocols.

Figure 26:
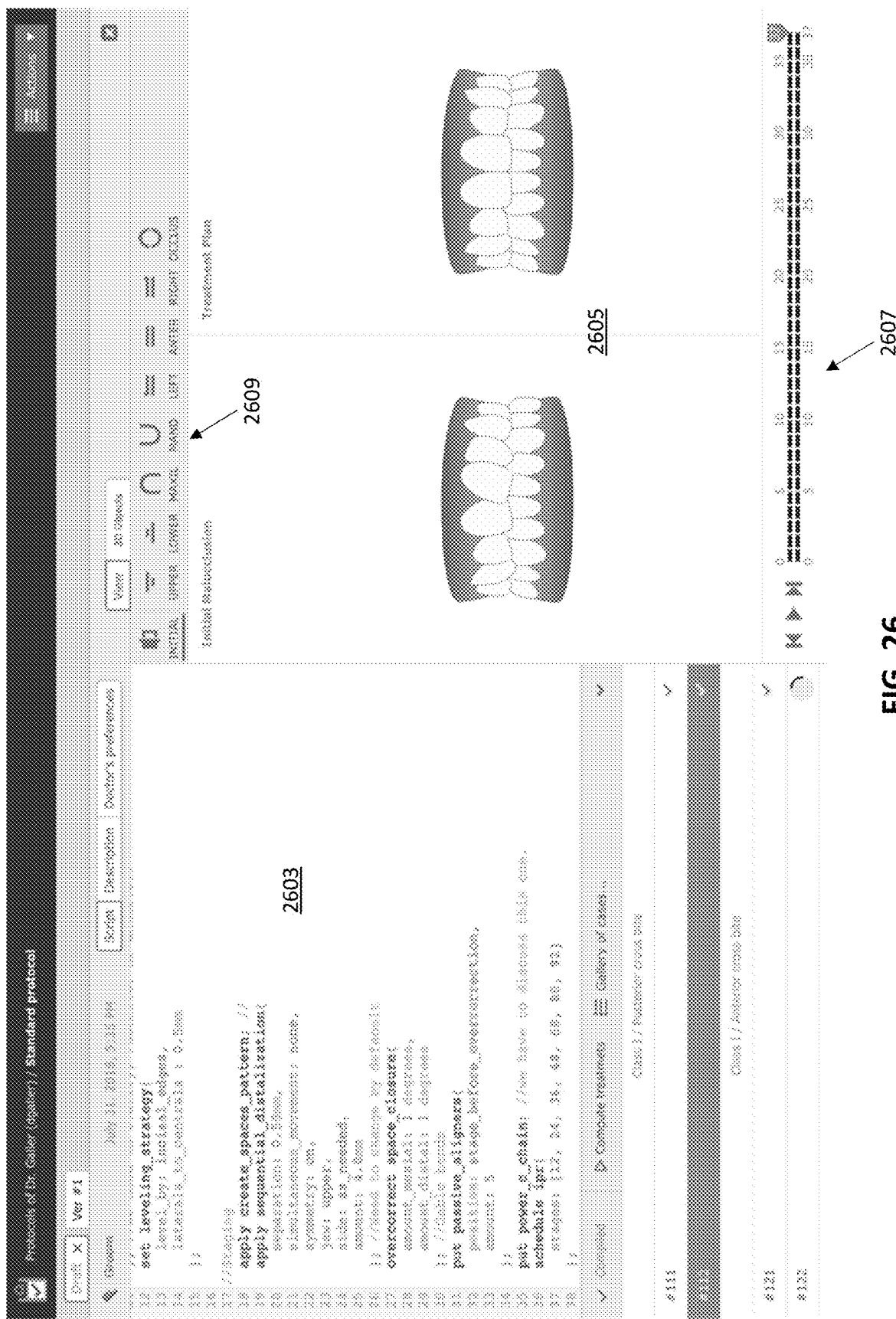
FIG. 26 shows one example of a user interface for treatment review and validation of a user-specific treatment protocol.

Additionally, the CPM system(s) 2806 may provide validation tools to validate treatment domain-specific protocols to ensure the treatment domain-specific protocols are accurate or otherwise in line with treatment preferences. As an example, the CPM system(s) 2806 may provide a visual depiction of how specific treatment domain-specific protocols would appear in treatment planning software. As noted herein, the CPM system(s) 2806 may employ one or more validation metrics to quantify validation. Examples of validation metrics that may be relevant to an orthodontic context include arch expansion metrics per quadrant, overjet metrics, overbite metrics, intercisal angle metrics, and/or flags if a treatment plan conforms with minimal or threshold root movement protocols. FIG. 26 shows an example screen capture of validation tools provided by the CPM system(s) 2806.

Figure 1A:
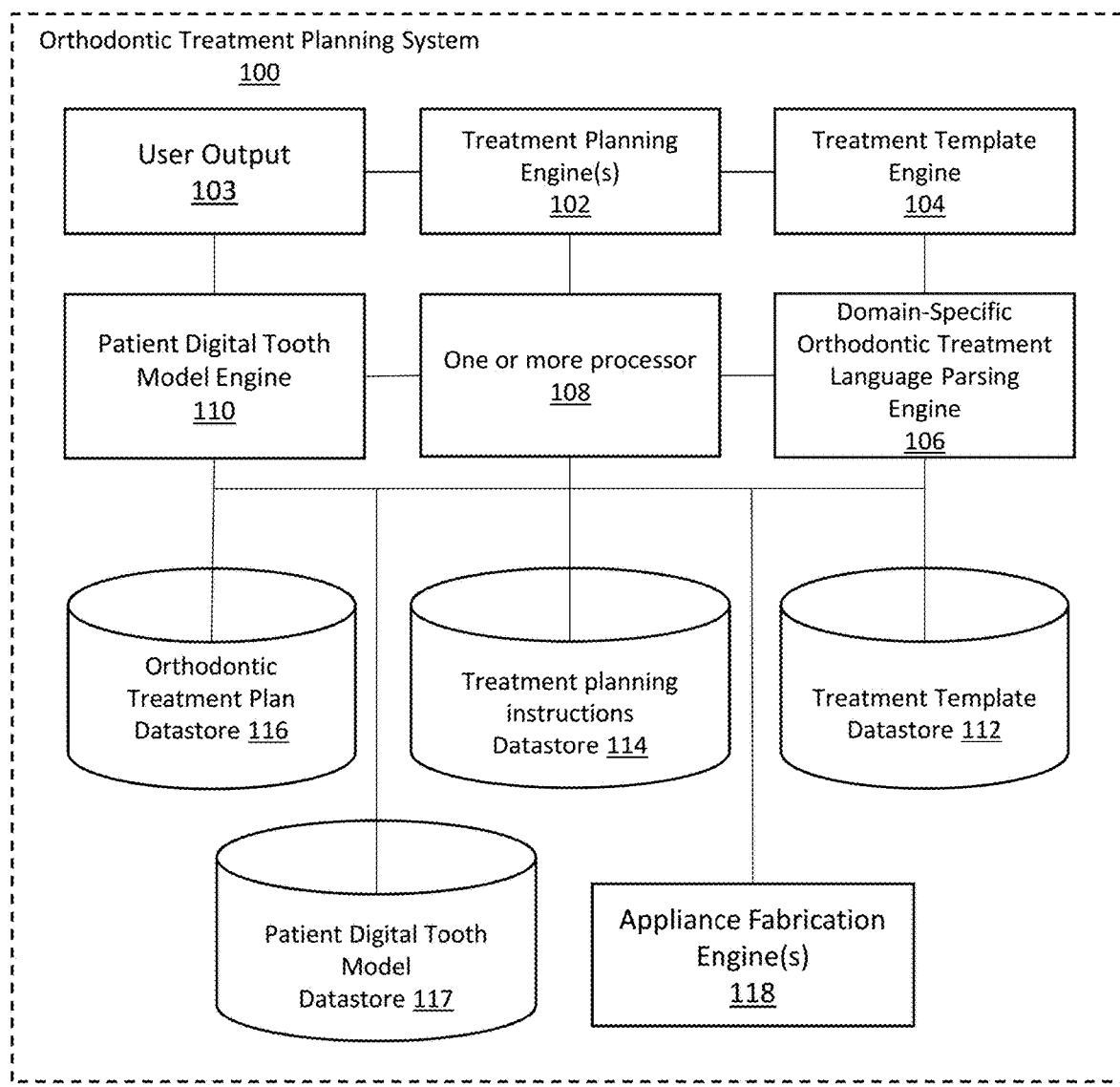
FIG. 1A is a diagram showing an example of an orthodontic treatment planning system.
Figure 1B:
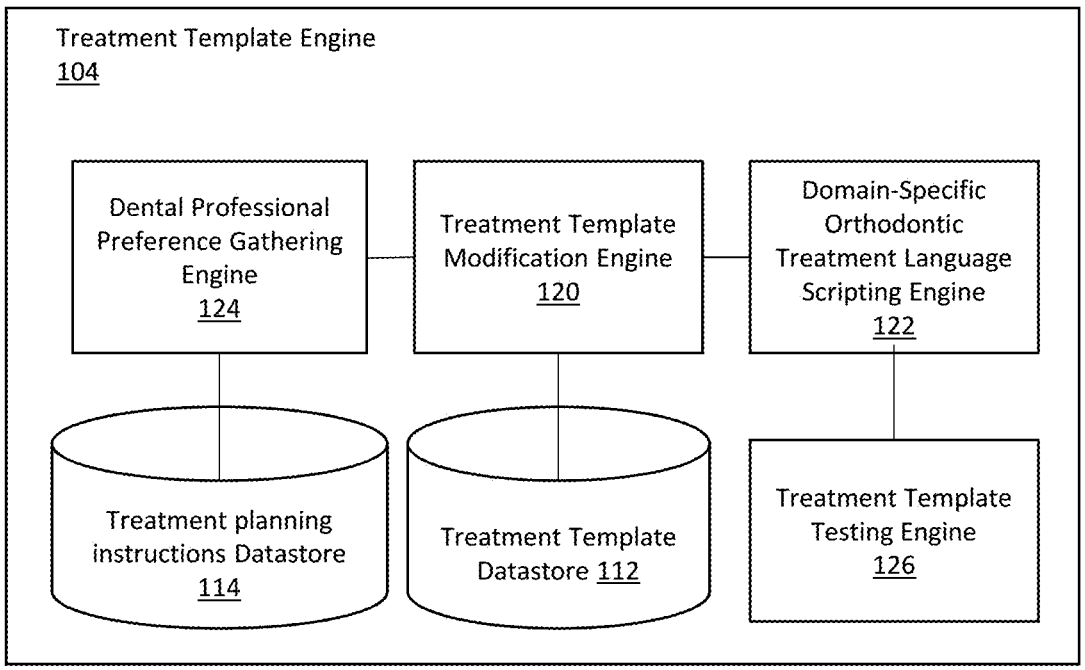
FIG. 1B is a diagram showing an example of a treatment template engine.
Figure 1C:
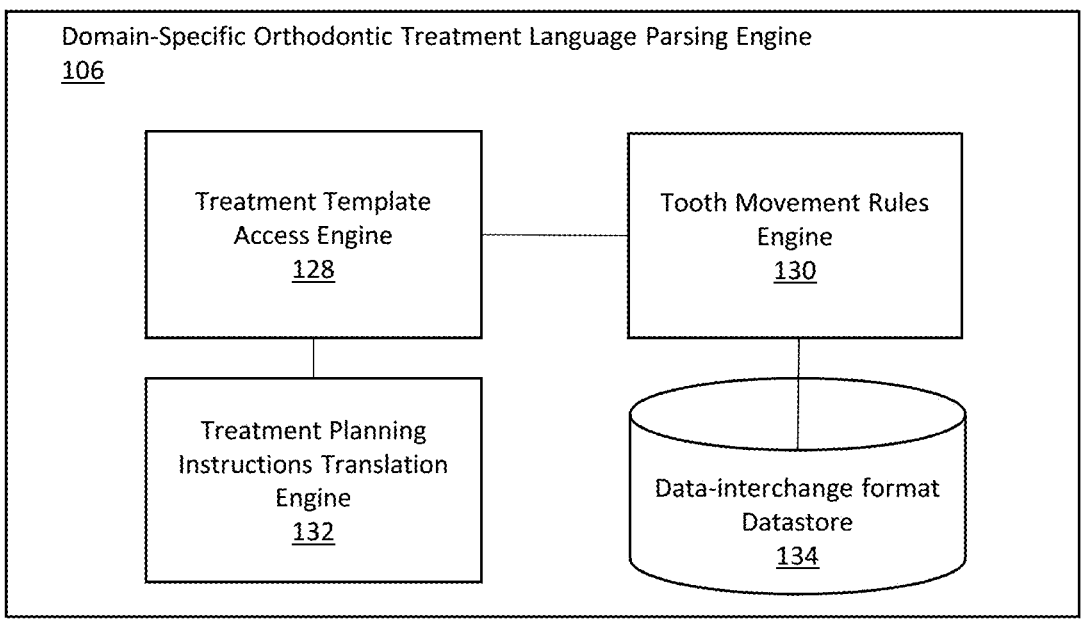
FIG. 1C is a diagram showing an example of a domain-specific orthodontic treatment language parsing engine.

The CPM system(s) 2806 may include one or more elements of the treatment template engine 104 shown in FIGS. 1A and 1B, and the domain-specific orthodontic treatment language parsing engine 106, shown in FIGS. 1A and 1C.

The treatment planning system(s) 2808 may include one or more computer systems configured to provide treatment plans to the treatment planning interface system(s) 2804. The treatment planning system(s) 2808 may receive patient data and the treatment preferences relevant to a user. The treatment planning system(s) 2808 may further provide treatment plans for the patient data that accommodate the treatment preferences relevant to the user. The treatment planning system(s) 2808 may implement automated and/or real-time treatment planning as referenced further herein.

The treatment planning system(s) 2808 may include one or more engines configured to provide treatment plans to the treatment planning interface system(s) 2804. The treatment planning system(s) 2808 may receive patient data and the treatment preferences relevant to a user. The treatment planning system(s) 2808 may further provide treatment plans for the patient data that accommodate the treatment preferences relevant to the user. In various implementations, the treatment planning system(s) 2808 identify and/or calculate treatment plans with instructions treat medical conditions. The treatment plans may specify treatment goals, specific outcomes, intermediate outcomes, and/or recommended appliances used to achieve goals/outcomes. The treatment plan may also include treatment lengths and/or milestones. In various implementations, the treatment planning system(s) 2808 calculate orthodontic treatment plans to treat malocclusions of teeth, restorative treatment plans for a patient's dentition, medical treatment plans, etc. The treatment plan may comprise automated and/or real-time elements and may include techniques described in U.S. patent application Ser. No. 16/178,491, entitled "Automated Treatment Planning." In various implementations, the treatment planning system(s) 2808 are managed by treatment technicians. As noted herein, the treatment plans may accommodate patient data in light of treatment preferences of users.

The treatment planning system(s) 2808 may include engines that allow users of the treatment planning interface system(s) 2804 to visualize, interact with, and/or fabricate appliances that implement a treatment plan. The treatment planning system(s) 2808 may support UIs that display virtual representations of orthodontic appliances that move a patient's teeth from an initial position toward a final position to correct malocclusions of teeth. The treatment planning system(s) 2808 can similarly include engines that configure the treatment planning interface system(s) 2804 to display representations of restorative appliances and/or other medical appliances. The treatment planning system(s)

2808 may support fabrication of appliances through, e.g., the appliance fabrication system(s) 2810.

In some implementations, the treatment planning system(s) 2808 provide customized GUIs that allow the user to discuss treatment plans with patients. The treatment planning system(s) 2808 may render patient data, conditions to be treated, and/or treatment options for display on the treatment planning interface system(s) 2804. The treatment planning system(s) 2808 may render potential appliances that are prescribed to implement a treatment plan (e.g., series of orthodontic appliances that are configured to move a patient's dentition from a first position toward a target position in accordance with an orthodontic treatment plan; effects of specific appliances at various stages of a treatment plan, etc.). In some implementations, the treatment planning system(s) 2808 supports a subscriptive flow for a method of using a treatment protocol to generate a treatment plan as shown in FIG. 18.

The treatment planning system(s) 2808 may include engines to support user interaction with treatment plans. The treatment planning system(s) 2808 may use treatment preferences, including those generated in treatment domain-specific protocols by the CPM system(s) 2806. In various implementations, the treatment planning system(s) 2808 provide treatment templates to the treatment planning interface system(s) 2804 that structure users' treatment preferences in a manner that is convenient to them. As noted herein, treatment templates may include structured data, UI elements (forms, text boxes, UI buttons, selectable UI elements, etc.), etc.

The treatment planning system(s) 2808 may include one or more datastores configured to store treatment templates expressed according to treatment domain-specific protocols. The treatment planning system(s) 2808 may further include one or more processing engines to process, e.g., parse, the treatment templates to form customized GUI elements on the treatment planning interface system(s) 2804. As noted herein, the processing engines may convert the treatment templates into scripts or other runtime elements in order to support the customized GUI elements on the treatment planning interface system(s) 2804. As noted herein, the treatment templates may have been created and/or validated by the CPM system(s) 2806.

In some implementations, the treatment planning system(s) 2808 provides the treatment planning interface system(s) 2804 with customized GUI elements that are generated using treatment domain-specific protocols. The customized GUI elements may be based on treatment templates, which, for a user may be customized based on a template library of treatment templates for other users. The treatment templates may comprise public and/or private treatment In some implementations, the treatment planning system(s) 2808 generates customized GUI elements for display by applications and/or processes on the treatment planning interface system(s) 2804. Customized GUI elements may operate to display attributes of treatment plans that are relevant to a specific user.

The treatment planning system(s) 2808 may include or more elements of the treatment planning engine(s) 102, the patient digital tooth model engine 110, the orthodontic treatment plan datastore 116, the treatment planning instructions 114, the treatment template datastore 112, and the patient digital tooth datastore 117, shown in FIG. 1A. The treatment planning system(s) 2808 may include one or more elements of the treatment template engine 104 shown in FIGS. 1A and 1B, and the domain-specific orthodontic treatment language parsing engine 106, shown in FIGS. 1A and 1C.

The appliance fabrication system(s) 2810 may include one or more computer systems configured to fabricate appliances. As discussed herein, examples of appliances to be fabricated include dental as well as non-dental appliances. Examples of dental appliances include aligners, other polymeric dental appliances, crowns, veneers, bridges, retainers, dental surgical guides, etc. Examples of non-dental appliances include orthotic devices, hearing aids, surgical guides, medical implants, etc.

The appliance fabrication system(s) 2810 may comprise thermoforming systems configured to indirectly and/or directly form appliances. The appliance fabrication system(s) 2810 may implement instructions to indirectly fabricate appliances. As an example, the appliance fabrication system(s) 2810 may be configured to thermoform appliances over a positive or negative mold. Indirect fabrication of a dental appliance can involve one or more of the following steps: producing a positive or negative mold of the patient's dentition in a target arrangement (e.g., by additive manufacturing, milling, etc.), thermoforming one or more sheets of material over the mold in order to generate an appliance shell, forming one or more structures in the shell (e.g., by cutting, etching, etc.), and/or coupling one or more components to the shell (e.g., by extrusion, additive manufacturing, spraying, thermoforming, adhesives, bonding, fasteners, etc.). Optionally, one or more auxiliary appliance components as described herein (e.g., elastics, wires, springs, bars, arch expanders, palatal expanders, twin blocks, occlusal blocks, bite ramps, mandibular advancement splints, bite plates, pontics, hooks, brackets, headgear tubes, bumper tubes, palatal bars, frameworks, pin-and-tube apparatuses, buccal shields, buccinator bows, wire shields, lingual flanges and pads, lip pads or bumpers, protrusions, divots, etc.) are formed separately from and coupled to the appliance shell (e.g., via adhesives, bonding, fasteners, mounting features, etc.) after the shell has been fabricated.

The appliance fabrication system(s) 2810 may comprise direct fabrication systems configured to directly fabricate appliances. As an example, the appliance fabrication system(s) 2810 may include computer systems configured to use additive manufacturing techniques (also referred to herein as "3D printing") or subtractive manufacturing techniques (e.g., milling). In some embodiments, direct fabrication involves forming an object (e.g., an orthodontic appliance or a portion thereof) without using a physical template (e.g., mold, mask etc.) to define the object geometry. Additive manufacturing techniques can include: (1) vat photopolymerization (e.g., stereolithography), in which an object is constructed layer by layer from a vat of liquid photopolymer resin; (2) material jetting, in which material is jetted onto a build platform using either a continuous or drop on demand (DOD) approach; (3) binder jetting, in which alternating layers of a build material (e.g., a powder-based material) and a binding material (e.g., a liquid binder) are deposited by a print head; (4) fused deposition modeling (FDM), in which material is drawn though a nozzle, heated, and deposited layer by layer; (5) powder bed fusion, including but not limited to direct metal laser sintering (DMLS), electron beam melting (EBM), selective heat sintering (SHS), selective laser melting (SLM), and selective laser sintering (SLS); (6) sheet lamination, including but not limited to laminated object manufacturing (LOM) and ultrasonic additive manufacturing (UAM); and (7) directed energy deposition, including but not limited to laser engineering net shaping, directed light fabrication, direct metal deposition, and 3D laser cladding. For example, stereolithography can be used to directly fabricate one or more of the appliances herein. In some embodiments, stereolithography involves selective polymerization of a photosensitive resin (e.g., a photopolymer) according to a desired cross-sectional shape using light (e.g., ultraviolet light). The object geometry can be built up in a layer-by-layer fashion by sequentially polymerizing a plurality of object cross-sections. As another example, the appliance fabrication system(s) 2810 may be configured to directly fabricate appliances using selective laser sintering. In some embodiments, selective laser sintering involves using a laser beam to selectively melt and fuse a layer of powdered material according to a desired cross-sectional shape in order to build up the object geometry. As yet another example, the appliance fabrication system(s) 2810 may be configured to directly fabricate appliances by fused deposition modeling. In some embodiments, fused deposition modeling involves melting and selectively depositing a thin filament of thermoplastic polymer in a layer-by-layer manner in order to form an object. In yet another example, the appliance fabrication system(s) 2810 may be configured to implement material jetting to directly fabricate appliances. In some embodiments, material jetting involves jetting or extruding one or more materials onto a build surface in order to form successive layers of the object geometry.

In some embodiments, the appliance fabrication system(s) 2810 may include a combination of direct and indirect fabrication systems. In some embodiments, the appliance fabrication system(s) 2810 may be configured to build up object geometry in a layer-by-layer fashion, with successive layers being formed in discrete build steps. Alternatively or in combination, the appliance fabrication system(s) 2810 may be configured to use a continuous build-up of an object's geometry, referred to herein as "continuous direct fabrication." Various types of continuous direct fabrication systems can be used. As an example, in some embodiments, the appliance fabrication system(s) 2810 may use "continuous liquid interphase printing," in which an object is continuously built up from a reservoir of photopolymerizable resin by forming a gradient of partially cured resin between the building surface of the object and a polymerization-inhibited "dead zone." In some embodiments, a semi-permeable membrane is used to control transport of a photopolymerization inhibitor (e.g., oxygen) into the dead zone in order to form the polymerization gradient. Examples of continuous liquid interphase printing systems are described in U.S. Patent Publication Nos. 2015/0097315, 2015/0097316, and 2015/0102532, (corresponding to U.S. Patent Nos. corresponding to U.S. Pat. Nos. 9,205,601, 9,216,546, and 9,211,678) the disclosures of each of which are incorporated herein by reference in their entirety. As another example, the appliance fabrication system(s) 2810 may be configured to achieve continuous build-up of an object geometry by continuous movement of the build platform (e.g., along the vertical or Z-direction) during the irradiation phase, such that the hardening depth of the irradiated photopolymer is controlled by the movement speed. Accordingly, continuous polymerization of material on the build surface can be achieved. Example systems are described in U.S. Pat. No. 7,892,474, the disclosure of which is incorporated herein by reference in its entirety.

In another example, the appliance fabrication system(s) 2810 may be configured to extrude a composite material composed of a curable liquid material surrounding a solid strand. The composite material can be extruded along a continuous 3D path in order to form the object. Examples systems are described in U.S. Patent Publication No. 2014/0061974, corresponding to U.S. Pat. No. 9,511,543, the disclosures of which are incorporated herein by reference in its entirety.

In yet another example, the appliance fabrication system(s) 2810 may implement a "heliolithography" approach in which a liquid photopolymer is cured with focused radiation while the build platform is continuously rotated and raised. Accordingly, the object geometry can be continuously built up along a spiral build path. Examples of such systems are described in U.S. Patent Publication No. 2014/0265034, corresponding to U.S. Pat. No. 9,321,215, the disclosures of which are incorporated herein by reference in its entirety.

The appliance fabrication system(s) 2810 may include one or more elements of the appliance fabrication engine(s) 118 shown in FIG. 1A.

The systems of the device planning environment 2800 may operate to provide customized GUIs related to treatment planning. In some implementations, the treatment planning interface system(s) 2804, the CPM system(s) 2806 and the treatment planning system(s) 2808 may operate to create treatment templates expressed according to treatment domain-specific protocols as follows. The CPM system(s) 2806 may gather unstructured representations of treatment preferences from the treatment planning interface system(s) 2804 through telephonic interviews, email exchanges, messages, conversations memorialized in notes, etc. A technician or an automated agent may use the tools on the CPM system(s) 2806 to create treatment templates for a user in accordance with treatment domain-specific protocols. The CPM system(s) 2806 may also validate the treatment templates to verify that the treatment templates accord with a given user and/or treatment outcome. The CPM system(s) 2806 may provide the treatment templates to the treatment planning system(s) 2808 for storage and/or use in execution.

Additionally, the treatment planning interface system(s) 2804, the treatment planning system(s) 2808, and/or the appliance fabrication system(s) 2810 may operate to provide treatment plans and/or appliances for a given patient. As noted herein, the treatment planning interface system(s) 2804 may gather patient data. With the patient data, a user whose treatment preferences were previously memorialized with a treatment template may gather one or more treatment plans using the engines in the treatment planning system(s) 2808. The treatment planning system(s) 2808 may gather treatment templates and parse these treatment templates using the treatment domain-specific protocols in order to efficiently and effectively generate customized GUI elements that express treatment preferences in the context of a treatment plan. The user may interact with the treatment plan using the treatment planning interface system(s) 2804. In various implementations, the user and/or the treatment planning system(s) 2808 provide instructions to fabricate appliances with the appliance fabrication system 2810.

FIG. 1A is a diagram showing an example of an orthodontic treatment planning system 100. The modules of the orthodontic treatment planning system 100 may include one or more engines, processors and datastores.

The orthodontic treatment planning system 100 may include a computer-readable medium, An orthodontic treatment planning engine 102, a treatment template engine 104, a patient digital tooth model engine 110, a domain-specific orthodontic treatment language parsing engine 106, an orthodontic treatment plan datastore 116, An orthodontic treatment planning instruction datastore 114, and a treatment template datastore 112. One or more of the components (including modules) of the orthodontic treatment planning system 100A may be coupled to one another (e.g., through the example couplings shown in FIG. 1A) or to modules not explicitly shown in FIG. 1A. The computer-readable medium may include any computer-readable medium, including without limitation a bus, a wired network, a wireless network, or some combination thereof.

The orthodontic treatment planning engine(s) 102 may include one or more processors configured to generate orthodontic treatment plans by applying the rules of the orthodontic treatment planning instructions on a digital model of a patient's teeth. The orthodontic treatment planning engine(s) may run on one or more processors (e.g., the one or more processor 108), and may include other rules (default rules) that are supplemental or modified by the orthodontic treatment planning instructions. In some variations, the orthodontic treatment planning engine implements one or more automated agents configured to learn orthodontic treatment planning for archforms taken from subjects.

In various implementations, the treatment template engine(s) 104 may implement one or more automated agents configured to generate, aggregate, and/or collect a treatment template in a domain-specific orthodontic treatment language. The treatment template engine(s) may include one or more outputs (screens, printers, etc.) 103 for listing, displaying, etc., use orthodontic treatment plans, and may connect to one or more datastores (e.g., treatment template datastores) containing a library or libraries of treatment templates. The treatment template engine may include one or more user interfaces (UIs) for selecting, modifying, storing, reviewing, etc., one or more treatment template.

In some implementations, the patient digital tooth model engine(s) 110 may be used to receive, collect, select and/or process information about a patient's dental arch. In some variations the information about the patient's dental arch is a scan of the patient's dental arch or a portion of it, taken directly or indirectly, such as by scanning an impression of the patient's teeth. In some implementations, the patient information is a digital scan from a handheld optical scanner (e.g., an intraoral scanner). The patient digital tooth model may collect, access, receive, store, process and/or modify one or more patient digital tooth models. The digital tooth model may be a 3D model of one or both of the patient's dental arches, and/or it may include a description of the patient's dental arch(s), and/or it may include data (including metadata) about the patient (e.g., patient age, gender, health, preexisting conditions, etc.).

In various implementations, the orthodontic treatment planning system implements one or more automated agents configured to gather a treatment template, including accessing the treatment template datastore 110, gather patient digital tooth model information, including accessing a patient digital tooth model datastore 117, and/or parse a treatment template to translating a treatment template into executable instructions for the orthodontic treatment planning engine(s) 102 using the domain-specific orthodontic treatment language parsing engine 106, which may access the orthodontic treatment planning instructions datastore 114.

The orthodontic treatment plans generated by the orthodontic treatment planning system may be stored, transmitted, reviewed, and/or modified (e.g., iteratively). The orthodontic treatment planning system 100 may output/display the orthodontic treatment plan(s), including output/displaying the modeled/predicted configurations of the patient's dental arch(s) and/or the treatment steps and/or the appliances needed; the orthodontic treatment planning system 100 may store the orthodontic treatment plan(s) in the orthodontic treatment plan datastore 116. Optionally, the orthodontic treatment planning system 100 may include an appliance fabrication engine(s) 118. The appliance fabrication engine(s) 118 may implement one or more automated agents configured to fabricate a dental appliance such as an aligner. Examples of an aligner are described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., San Jose, Calif., under the tradename, Invisalign System. Throughout the description herein, the use of the terms "orthodontic aligner", "aligner", or "dental aligner" is one example of the terms "appliance" and "dental appliance" in terms of dental applications. Other appliances/dental appliances may include palatal expanders, bite ramps, etc. For purposes of clarity, embodiments are hereinafter described within the context of the use and application of dental aligners, but it should be understood that, unless indicated otherwise, these apparatuses and methods may apply to any dental appliance. The appliance fabrication engine(s) 118 may be part of 3D printing systems, thermoforming systems, or some combination thereof.

FIG. 1B is a diagram showing an example of the treatment template engine(s) 104. The treatment template engine(s) 104 may include a dental professional preference gathering engine 124, a treatment template modification engine 120, a domain-specific orthodontic treatment language scripting engine 122, and/or a treatment template testing engine 126. One or more of the modules of the automated treatment template engine(s) 104 may be coupled to one another (e.g., through the example couplings shown in FIG. 1B) or to modules not explicitly shown in FIG. 1B. The treatment template engine may also include (and any of the modules 124, 120, 122, 126) may access, an orthodontic treatment planning instruction datastore 124.

The treatment template engine 104 may generate a treatment template written in a domain-specific orthodontic treatment language. For example, the treatment template engine 104 may generate de novo a treatment template for a user, or the treatment template engine 104 may modify an existing treatment template from one or more (e.g., a library) of treatment templates, e.g., stored in the treatment template datastore 112. The dental professional preference gathering engine(s) 124 may aggregate preference information for the user (e.g., dental professional), and may include one or more user interfaces for requesting and receiving preference data. The treatment template engine may encode the preferences of the dental professional into the treatment template with the assistance of the domain-specific orthodontic treatment language scripting engine 122. During or after the formation of the treatment template in the domain-specific orthodontic treatment language, the treatment template engine may (in some cases, iteratively) test the treatment template, e.g., using the treatment template testing engine 126. The treatment template may be tested by parsing (or attempting to parse) the treatment template into orthodontic treatment planning instructions. Problems in parsing may be flagged and addressed as part of the treatment template engine, including notifying the user (via the output) and allowing modification of the problematic portions. In some variations the testing may further include executing or simulating execution of the orthodontic treatment planning instructions in the orthodontic treatment planning instructions and either a "test case" of patient dental information, or using actual patient dental information, such as a digital model of the patient's teeth. The user (e.g., dental professional) may view the orthodontic treatment plan and may modify the treatment template based on the resulting orthodontic treatment plan(s), until the user is satisfied. Once finalized, the treatment template may be stored (e.g., in the treatment template datastore) and indexed to the user for later use.

FIG. 1C is a diagram showing an example of the domain-specific orthodontic treatment language parsing engine(s) 106. The domain-specific orthodontic treatment language parsing engine (s) 106 may include a treatment template access engine 128, a tooth movement rules engine 130, and/or an orthodontic treatment planning instructions translation engine 132. One or more of the modules of the domain-specific orthodontic treatment language parsing engine(s) 106 may be coupled to one another (e.g., through the example couplings shown in FIG. 1C) or to modules not explicitly shown in FIG. 1C. The domain-specific orthodontic treatment language parsing engine(s) may also include, and any of the modules 128, 130, 132 may access, a data-interchange format datastore 134.

The domain-specific orthodontic treatment language parsing engine 106 may build a set of orthodontic treatment planning instructions based at least in part on the treatment template (including the domain-specific orthodontic treatment language of the treatment template). The treatment template access engine may acquire a treatment template written in a domain-specific orthodontic treatment language. The treatment template may be stored in the treatment template datastore 112. The acquired treatment template may then be translated by the orthodontic treatment planning instructions translation engine 132 which may parse the domain-specific orthodontic treatment language into a set of rules (e.g., orthodontic treatment planning instructions) in conjunction with the tooth movement rules engine 130. The tooth movement rules engine 130 may also set default rules for preferences or actions that are not specified by the treatment template. The rules for treating (e.g., moving) the teeth specified by the treatment template and the tooth movement rules engine 130 may be expressed in a data-interchange format, including by accessing a data-interchange format datastore 134. Expressing the orthodontic treatment planning instructions in a data-interchange format may allow them to be executed by the orthodontic treatment planning engine(s) to generate one or more orthodontic treatment plans when applying the orthodontic treatment planning instructions to patient-specific data (e.g., a digital model of the patient's teeth) in the orthodontic treatment planning engine(s) 102.

Figure 1D:
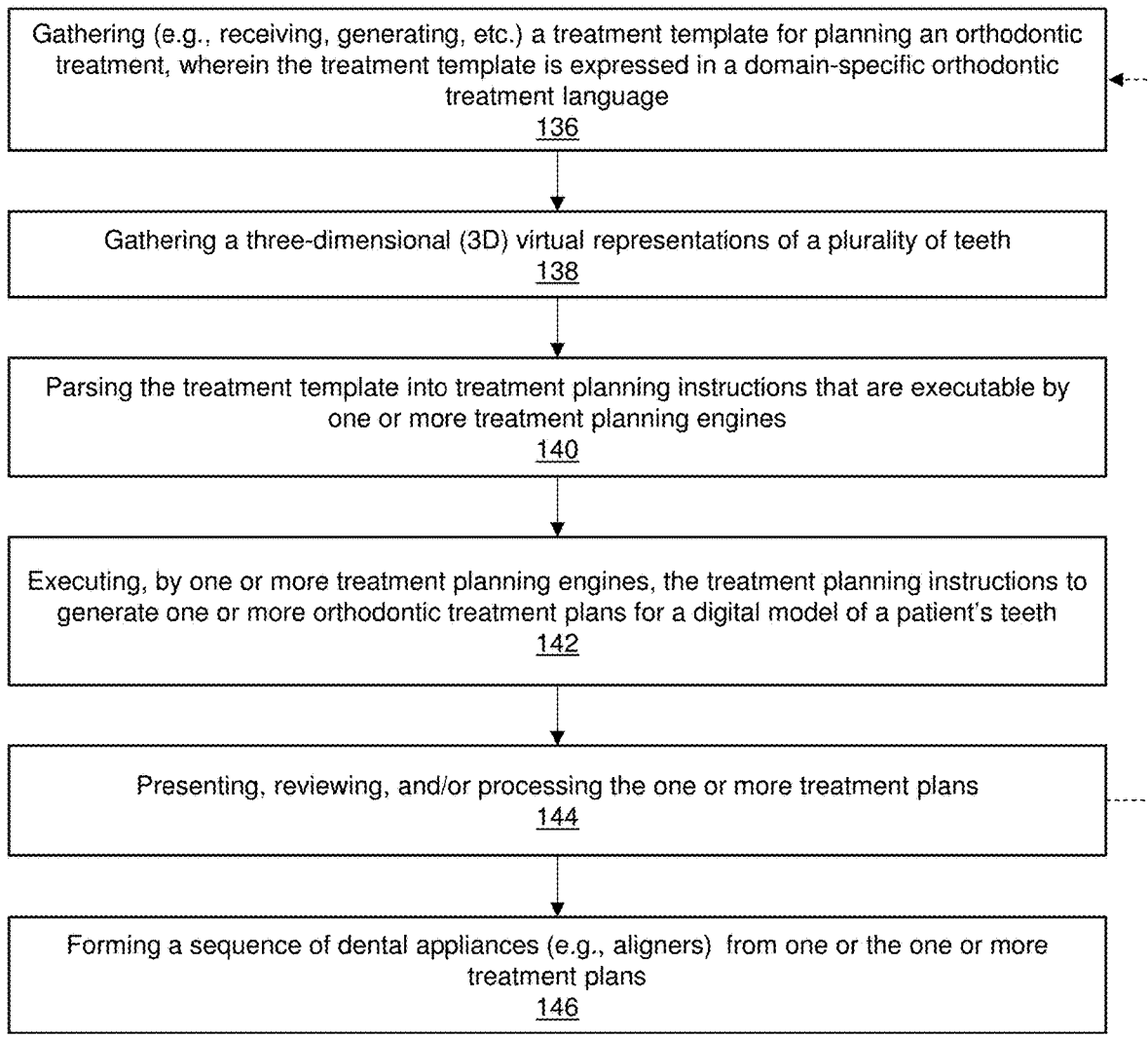
FIG. 1D is a flowchart of an example of a method of generating an orthodontic treatment plan for an orthodontic treatment.

FIG. 1D is an example of a method of both generating a patient-specific orthodontic treatment plan using a treatment template for (e.g., created, modified for and/or chosen by) a user. This method also includes the step of forming a sequence of dental appliances (e.g., aligners) using the orthodontic treatment plan. In FIG. 1D, the treatment template may be gathered, e.g., by generating, selecting, receiving, etc., a treatment template for planning an orthodontic treatment; the treatment template is expressed in a domain-specific orthodontic treatment language 136. Thus, gathering includes generating either de novo, and/or modifying or deriving from an existing orthodontic treatment plan. The orthodontic treatment plan is written in the domain-specific orthodontic treatment language. The orthodontic treatment plan may be recalled from a storage/memory, and provided with a set of patient-specific data, such as a 3D digital model of the patient's teeth 138, to one or more orthodontic treatment planning engine(s).

The orthodontic treatment plan may be parsed into a set of orthodontic treatment planning instructions 140 either before or after passing to the orthodontic treatment planning engine. Once parsed, the orthodontic treatment planning instructions may be executed by the orthodontic treatment planning engine operating on the patient-specific data to generate the orthodontic treatment plan 142. Once the orthodontic treatment plan(s) is/are created, they may be presented, reviewed, and/or processed 144. Optionally (as shown by the dashed line), the orthodontic treatment plan may be modified by modifying the treatment template. In some variations, the resulting orthodontic treatment plan may then be used to form a sequence of dental appliances (e.g., dental aligners) 146, which may be sent to the user and/or the patient.

Figure 2A:
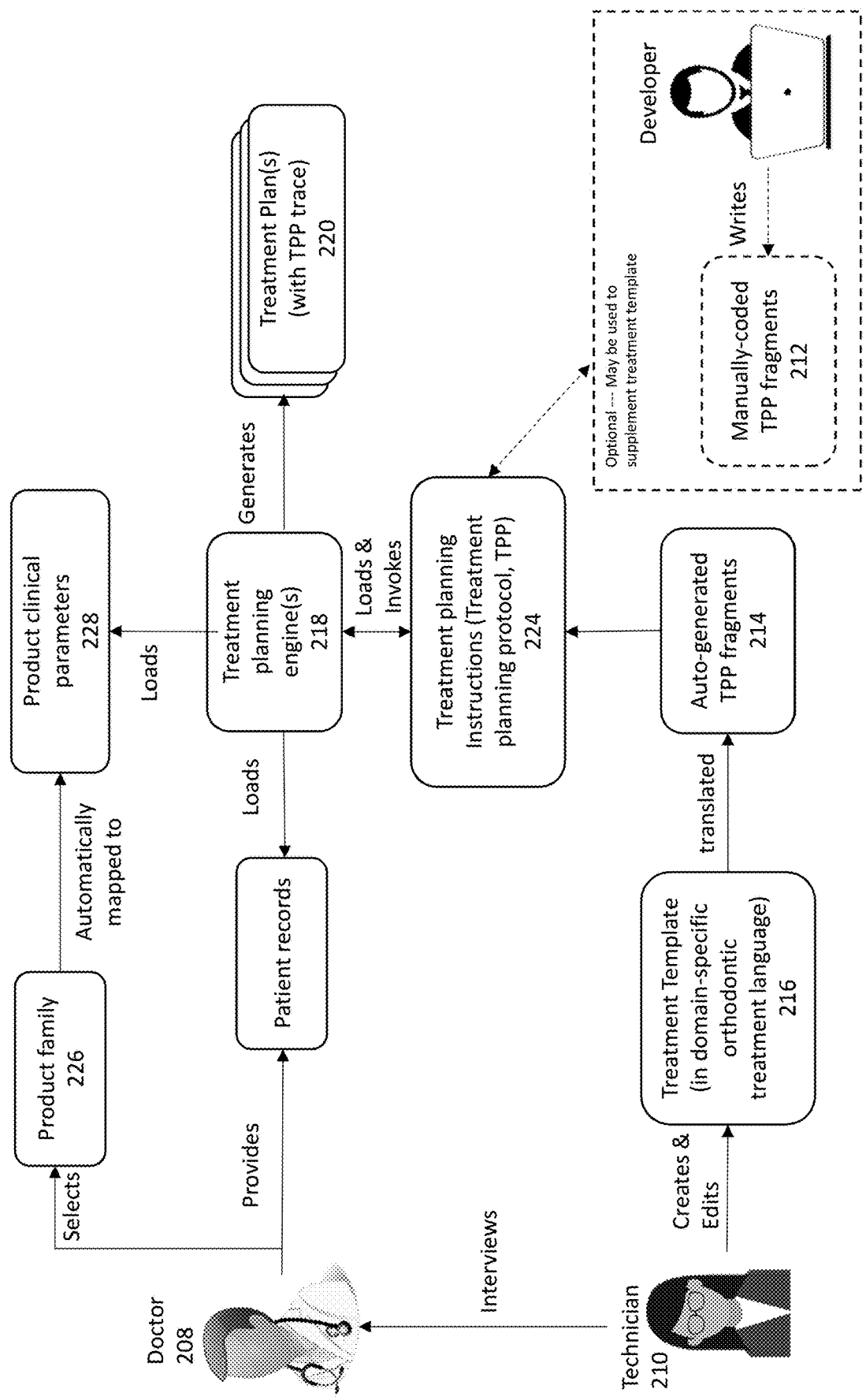
FIG. 2A is a diagram schematically showing an example of a method for generating one or more orthodontic treatment plans.

FIG. 2A is an overview of one variation of the treatment template creation process. In FIG. 2A, the flow of information used to generate the orthodontic treatment plan(s) 220 is shown. In this example the process is trackable using a log trace ("Treatment Planning Protocol trace" or "TPP trace"). A TPP trace is a log of the orthodontic treatment planning instructions (from the treatment template) or rules that were fired when generating each orthodontic treatment plan. The log trace may be used for troubleshooting and for analytics. A single orthodontic treatment plan or multiple orthodontic treatment plans may be generated by the orthodontic treatment planning engine(s) 218. Some orthodontic treatment planning engines are configured to provide multiple, alternative orthodontic treatment plans. The variables used to generate the multiple different orthodontic treatment plans may be indicated by the user, including as part of the treatment template. These variables may include, for example, the number of stages (e.g., 12, 18, 20, 24, 30, etc.) the use of attachments/no attachments, etc. Virtually any of the user preferences may be varied to generate alternative orthodontic treatment plans. The resulting orthodontic treatment plans may be separated provided or may be provided as an array, data set, etc.

The orthodontic treatment planning engine 218 may accept, collect, load or otherwise receive the orthodontic treatment planning instructions 224 (also referred to herein as "treatment planning protocol" or TPP). In the example shown in FIG. 2A, the orthodontic treatment planning instructions are assembled from the treatment template 216, after it has been parsed, e.g., translated, from the domain-specific orthodontic treatment language into orthodontic treatment planning instructions. In FIG. 2A the rules from the treatment template may be combined with automatically generated (e.g., "generic") rules 214 or fragments of orthodontic treatment planning instructions. The portion(s) of the orthodontic treatment planning instructions from the treatment template and auto-generated rules may optionally be combined with manually coded orthodontic treatment planning instructions 212 to form the final set of orthodontic treatment planning instructions 224. In general, the orthodontic treatment planning instructions may be encoded an interpreted language that can be invoked by the orthodontic treatment planning engine (e.g., "Treat") 218. Although the orthodontic treatment planning instructions 224 in FIG. 2A are shown as a combination of instructions from the treatment template 216, manually encoded rules 212, and automatically generated rules 214, in some variations, the orthodontic treatment planning instructions may be derived only from the treatment template or only the treatment template and auto-generated rules, or only the treatment template and manually-coded fragments.

The treatment template itself may be created and edited by a technician 210 and/or a user (e.g., dental professional), such as a doctor 208. The user may also provide the patient information to the orthodontic treatment planning engine(s) 218. For example, the user may provide patient records 222, which may include, for example, a digital model of the patient's teeth (e.g., a 3D surface and/or volumetric model) that may be used to generate the orthodontic treatment plan(s). In addition, the user may also specify additional parameters to the orthodontic treatment planning engine, such as which parameters to vary when generating multiple orthodontic treatment plans, including different aligner products 226 (e.g., number of stages). For example, by selecting which dental product (e.g., dental alignment product) to use, the user may select which options to vary when generating multiple different orthodontic treatment plans, corresponding to different product clinical parameters 226. As mentioned above, optionally these variable parameters may be specified in the treatment template, e.g., as general defaults for the particular user.

Figure 2B:
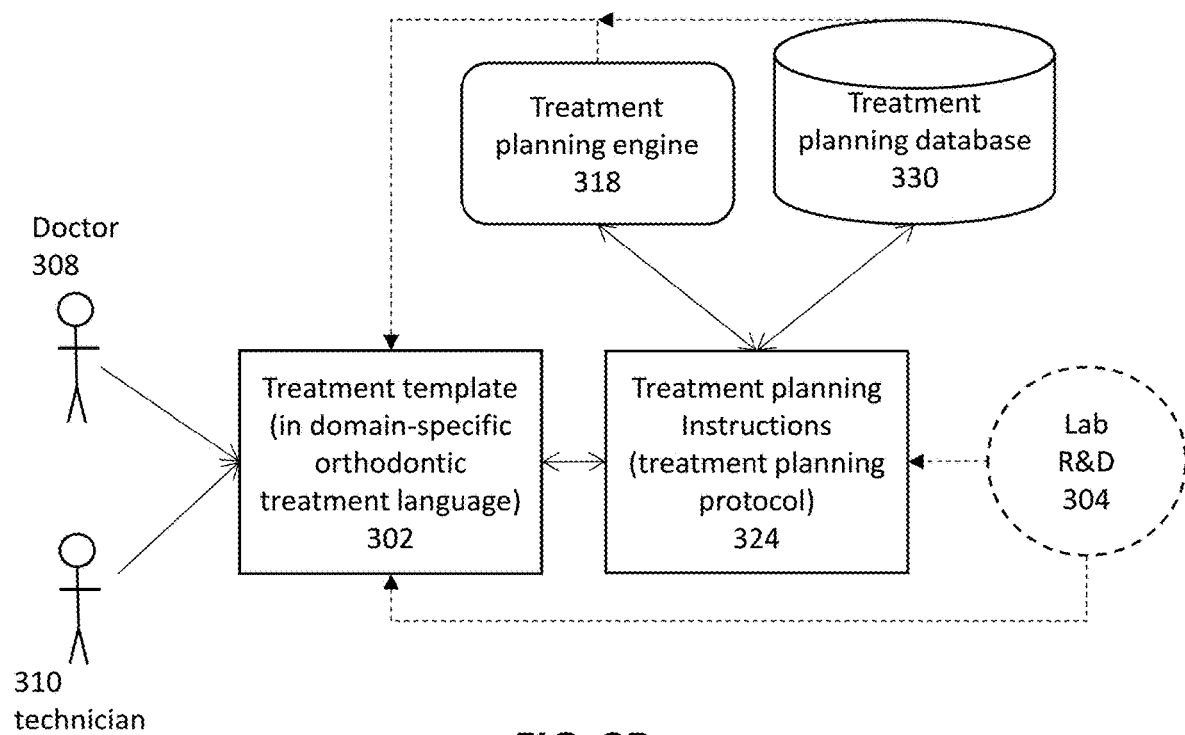
FIG. 2B is a diagram showing an example of a system for orthodontic treatment plan formation.

FIG. 2B illustrates an alternative view of one method for selecting, modifying or designing an orthodontic treatment plan specific to a user. In FIG. 2B, the user 308 may herself generate (e.g., select, modify, create) an orthodontic treatment plan 310, or the user may work with a technician 310. In general, the treatment template is expressed in a domain-specific orthodontic treatment language. For example, the user and/or technician may be provided with a user interface that translates user preferences for orthodontic treatment options into the domain-specific orthodontic treatment language and/or the user and/or technician may directly write the treatment template in the domain-specific orthodontic treatment language. Optionally, the dental lap (e.g., the services provider) may directly modify the treatment template 304. In some variations, every treatment template may be modified, e.g., automatically, to include certain baseline and/or default orthodontic treatment planning instructions (rules) that are used by the orthodontic treatment planning engine(s) 318.

Once the treatment template draft is complete, it may be tested and/or used directly by being parsed into a set of orthodontic treatment planning instructions 324. The orthodontic treatment planning instructions are typically executable by the orthodontic treatment planning engine.

In any of these examples, the treatment template may be vetted or tested and/or modified. For example, the treatment template, after parsing into orthodontic treatment planning instructions, may be provided to the orthodontic treatment planning engine 318 and a test set of patient dental information (e.g., a test digital model of 'patient's' teeth) may be used to generate a test orthodontic treatment plan. The test set of information may be stored, e.g., in the orthodontic treatment planning database 330. This orthodontic treatment plan may include written and/or images showing the stages of the orthodontic treatment plan, including simulations (images, 3D models, views, etc.) of the patient's (or test patient's) teeth at each state and/or a description (written, mathematical, images, etc.) of the dental appliance used at each stage. The user 308 may review the test results and, by themselves or in conjunction with the technician 310, modify the treatment template. Although FIG. 2B illustrates a test case, the same feedback may be provided for actual patient data.

Figure 2C:
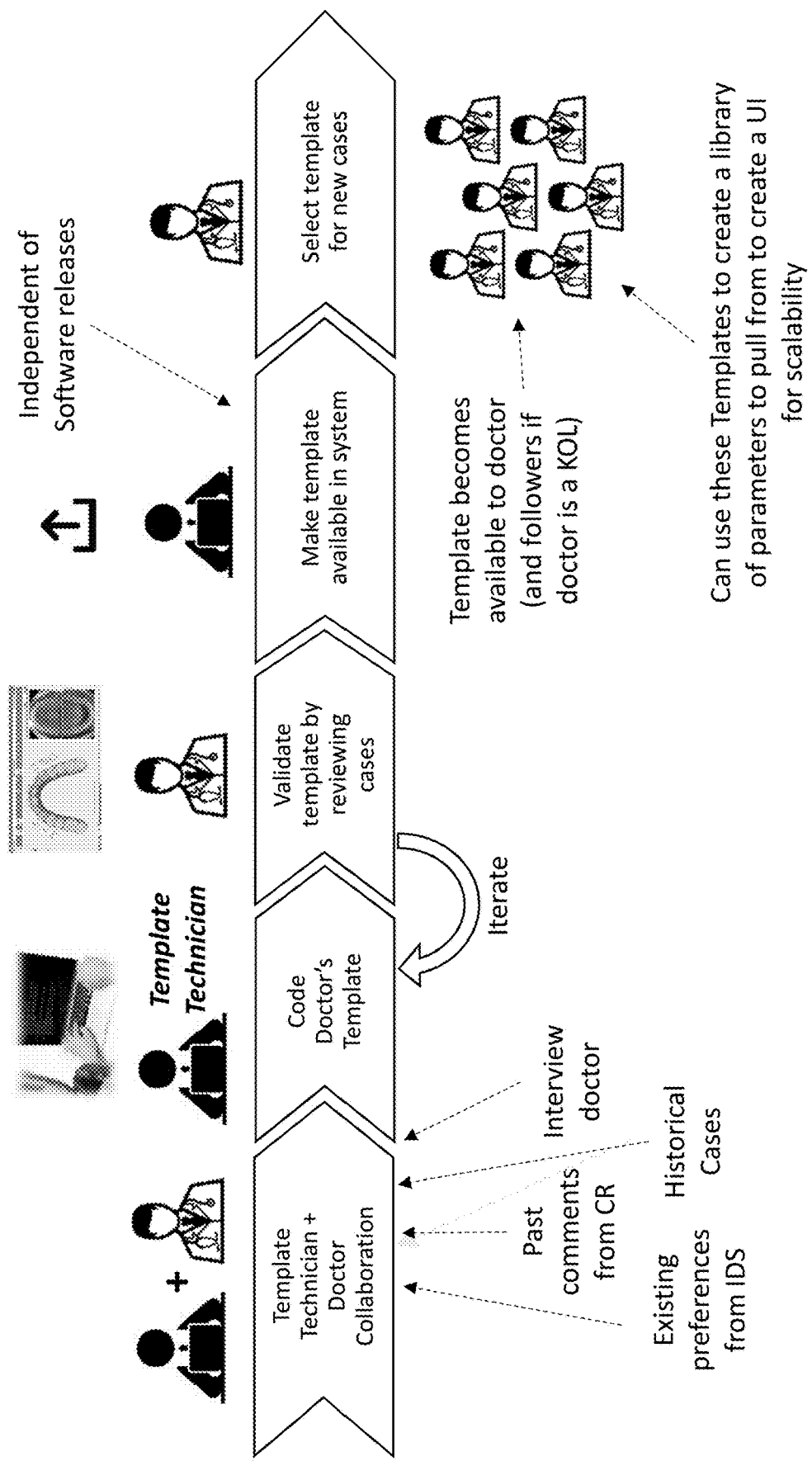
FIG. 2C is a diagram showing an example of a method of creating a treatment template for an orthodontic treatment.

FIG. 2C schematically illustrates another example of the creation of a treatment template for a particular use (e.g., dental professional, such as a doctor). In FIG. 2C, the dental professional may collaborate with a technician to code the treatment template in a domain-specific orthodontic treatment language. The template may be filled in with the user's preferences based on, e.g., existing preferences from other cases/templates, historical data from other cases for the same user, past comments from the user, and current interview information. The treatment template may be validated (tested) by reviewing test cases, and reviewed by the user and/or technician, and iteratively modified. The treatment template may then be saved or stored in the system (e.g., the orthodontic treatment planning system) and may be used as a template by that user or other users. For example, the treatment template may be marked with a user-identifying indicator (e.g., number, alphanumeric, etc.) or code that is affiliated with the user. The treatment template may also be marked as public (meaning other users may select and/or form a modified version of it) or marked private. The template may then be used immediately or later for generating an orthodontic treatment plan on one or more cases. Once the user template(s) are completed, the entire process of generating an orthodontic treatment plan and/or generating dental appliances that conform to the orthodontic treatment plan for a patient may be performed quickly, in a streamlined manner.

Figure 2D:
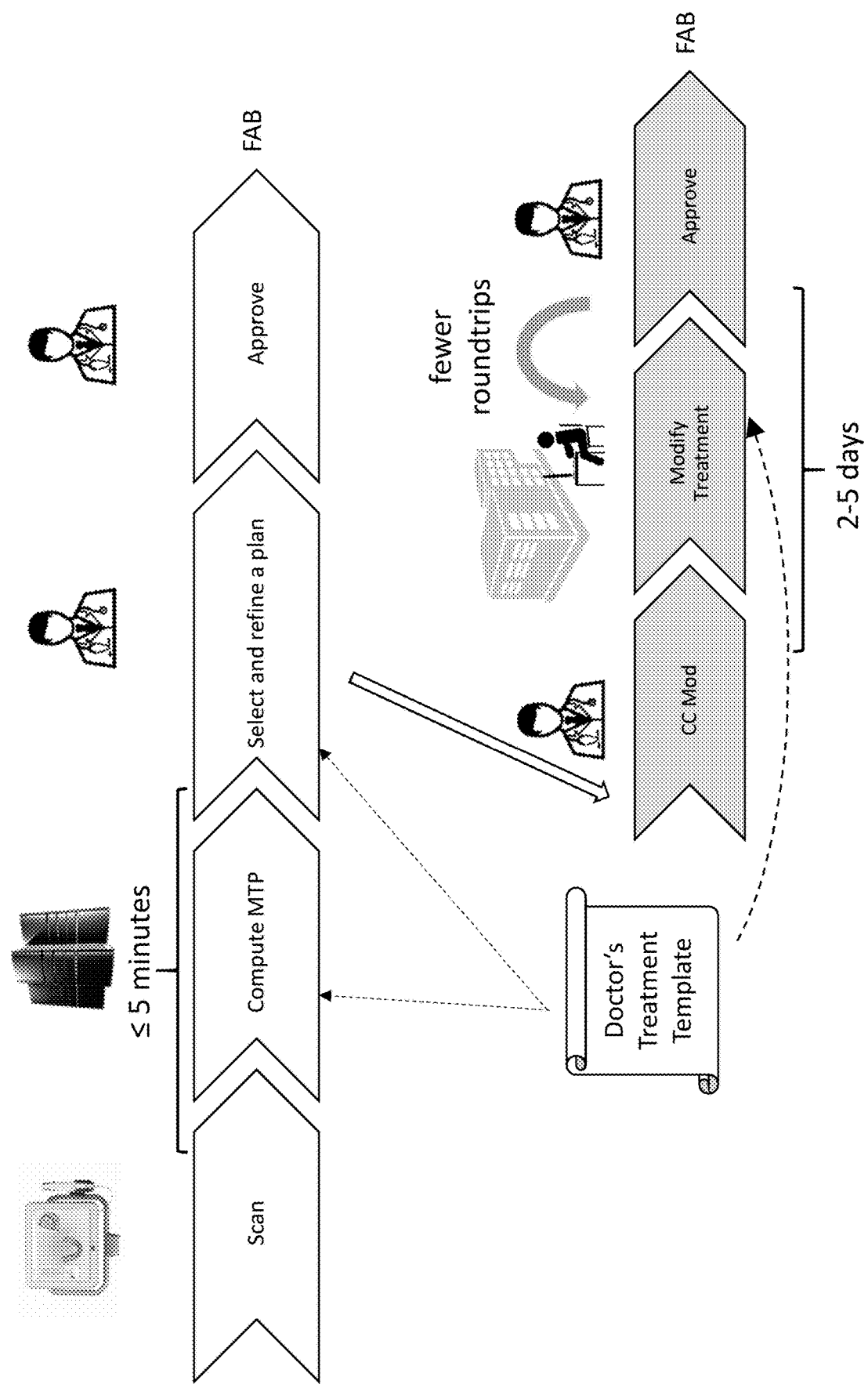
FIG. 2D is a diagram showing an example of a method for generating a sequence of orthodontic appliances for an orthodontic treatment.

For example, as shown in FIG. 2D, the user treatment template may be applied to any patient for that user (e.g., that dental professional). The patient's dental arch may be scanned, either directly or indirectly, and this patient dental information (e.g., digital model of the patient's teeth) may be stored and applied, along with the user-selected orthodontic treatment plan to an orthodontic treatment planning engine to generate one or more orthodontic treatment plan. This process may be done quickly, e.g., within a few minutes, since the treatment template may be pre-validated and stored by the system. The patient and/or user may then view the one or more orthodontic treatment plans, and select which orthodontic treatment plan to proceed with, and the dental appliances (e.g., aligners) corresponding to that orthodontic treatment plan may be fabricated. Alternatively, as shown in FIG. 2D, the orthodontic treatment plan may be modified by the user, who may modify the treatment template and the modified orthodontic treatment plan may be fed back to the orthodontic treatment planning engine again.

The treatment templates typically record user treatment preferences. The use of the domain-specific orthodontic treatment language that is both human and machine readable, and is tailored to orthodontic treatment provides a high level of flexibility and efficiency in orthodontic treatment planning and orthodontic device fabrications. For example, the domain-specific orthodontic treatment language enables automation of many different orthodontic treatment planning protocols, and facilitates the communication between users (e.g., doctors), technicians and R&D personnel. It adds more flexibility than simple parameter files, because it includes semantics for conditional statement, and because it exposes more configuration options. The domain-specific orthodontic treatment language may be used for editing and for visualizing the TPP, and may therefore be concise and easy to understand. The domain-specific orthodontic treatment language scripts may be automatically translated into executable code in an interpreted language.

The treatment template may be translated into all or a part (e.g., a fragment) of the orthodontic treatment planning instructions that are provided to the orthodontic treatment planning engine(s) for generating orthodontic treatment plans. Orthodontic treatment planning instructions are typically a complete specification of how a treatment should be planned. The domain-specific orthodontic treatment language is a language that may describe the configurable parts of an orthodontic treatment planning instructions. The domain-specific orthodontic treatment language may not be a complete set of orthodontic treatment planning instructions, because some parts of the orthodontic treatment planning instructions may be hard-coded.

Figure 3:
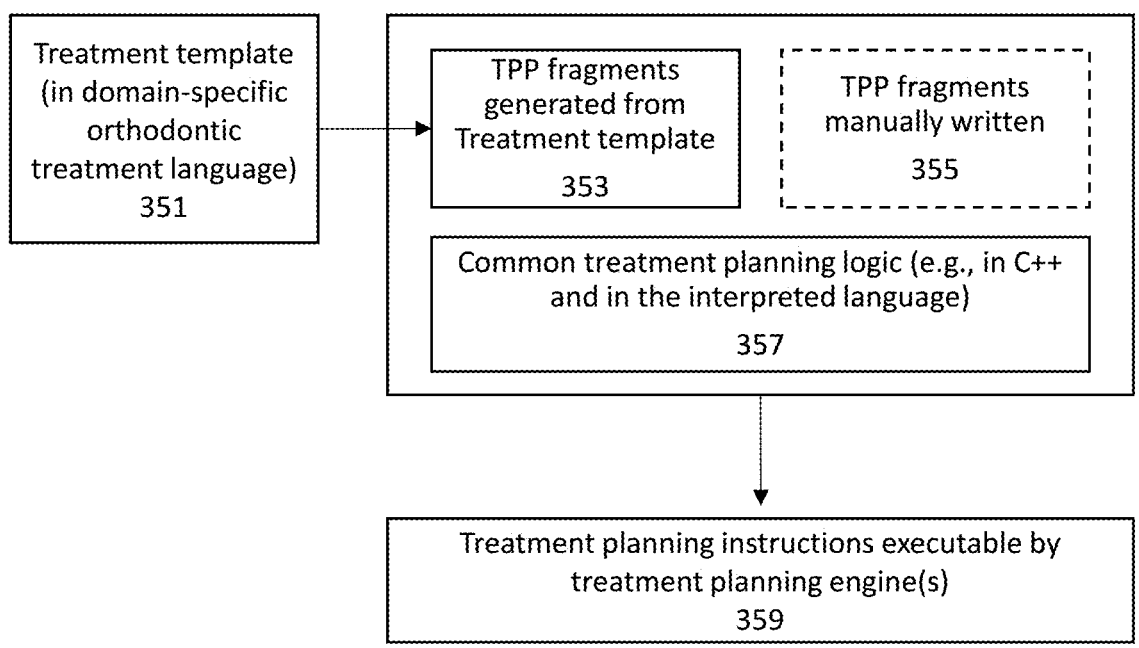
FIG. 3 is a diagram of an example of a method of generating orthodontic treatment planning instructions that are executable by an orthodontic treatment planning engine.

For example, FIG. 3 illustrates the generation of a complete set of orthodontic treatment planning instructions, showing the formation of orthodontic treatment planning instructions (e.g., an orthodontic treatment planning Protocol, or TPP) from component parts, including a treatment template as well as automatically and/or manually added parts. In FIG. 3, a treatment template 351 is parsed into orthodontic treatment planning instructions 353, and these instructions are combined with automatically generated additional orthodontic treatment planning instructions 357, which may be common orthodontic treatment planning instructions 357. Optionally, additional orthodontic treatment planning instructions 355 may be added. The final orthodontic treatment planning instructions 359 may be the combined set of orthodontic treatment planning instructions and may be executable directly by the orthodontic treatment planning engine. These orthodontic treatment planning instructions may be in a data-interchange format that may be processed directly by the orthodontic treatment planning engine(s).

For example, the source code for a complete set of orthodontic treatment planning instructions may be made of three parts, including parts that are common to all orthodontic treatment planning instruction sets (which may be written in, for example, a combination of computer languages, such as partially in C++ and partially in the domain-specific orthodontic treatment language), and parts that are specific to a particular orthodontic treatment planning engine. The parts that are specific to the particular orthodontic treatment planning engine may be written in the domain-specific orthodontic treatment language, and may be generated from the treatment template. In some variations, only the second part (e.g., the treatment template) is used, as it may include the 'common' instructions as defaults.

Domain-Specific Orthodontic Treatment Language

A domain-specific orthodontic treatment language may include syntax and grammar that is specific to orthodontic treatments. For example, a domain-specific orthodontic treatment language may include grammar specific to clinical settings, which may affect one or more of the orthodontic treatment planning phases. The domain-specific orthodontic treatment language may include a verb and a noun, and optional arguments. For example: "disable class_correction"; "restrict movements (teeth: molars)"; "limit ipr (teeth: anteriors, max_amount: 0.30 mm)"; "set filters (any_product, open_bite, overjet, ipr, attachments)"; "put hook(on: upper canines)".

The domain-specific orthodontic treatment language may also include conditional statements, including conditional "if" statements that refer to the initial position, final position, treatment goals or existence of teeth or other conditions in the dental arch and treatment of the dental arch. For example: "if (initially open_bite>0.5 mm) . . . "; "if (performing intrusion(upper anteriors)>0.5 mm) . . . "; "if (performing extrusion(lower molars)>0.5 mm and initially posterior_open_bite>0.3 mm) . . . ".

The domain-specific orthodontic treatment language may also include values that are given in units appropriate to the orthodontic treatment such as: millimeters, degrees or percentages, etc.: "50%"; "1.5 mm"; "−0.5 mm"; "30 degrees".

The domain-specific orthodontic treatment language may reference directly tooth types and number, and may use ranges of teeth and individual tooth names, such as: "canines"; "molars"; "canines and molars"; "upper left molars and lower left molars"; "upper 2nd premolar and lower 2nd premolar"; "primary second molars"; "upper primary centrals".

The domain-specific orthodontic treatment language may include loops, such as "for" loops, to repeat a set of instructions over a range of teeth, quadrants or for each jaw. For example:

```
for each tooth (of: canines) {
    if (performing rotation > 30 degrees) // Repeated for each single tooth
independently
        postpone movement(direction: rotation);
            put attachment teeth: mesial, type: optimized);
    }
```

And:

```
for each quadrant (of: [upper left, upper right]) { ... }
    for each jaw {
        if (performing intrusion(teeth: anteriors) > 0.5mm) {
            put attachment(on: canine, type: CRT, size: 3mm, direction: horizontal,
                min_distance_from_occlusal: 1mm);
            put attachment(on: 1st premolar, type: CRT, size: 3mm, direction:
horizontal,           min_distance_from_occlusal: 1mm);
        }
    }
```

The domain-specific orthodontic treatment language may include lists (e.g., sequences of entities where the order matters), such as: "apply movement_separation(teeth: anteriors, order: [lingual_root_torque, intrusion])"; "apply sequential_movement(movement: mesialization, overlap: 0%, order: [incisors, canines])".

The domain-specific orthodontic treatment language may also include nested code blocks, such as:

```
if (performing extrusion(upper molars) > 0.5mm) {
    if (not performing distalization(upper molars)) {
        apply sequential_movement(direction: extrusion, teeth: [upper premolars, upper
molars]);
    } else {
        apply sequential_movement(direction: extrusion, teeth: [upper molars, upper
premolars]);
    }
}
```

The domain-specific orthodontic treatment language may also reuse different templates or parts of templates, and may call them by name. For example: "use template Dr. XYZ"; "use template XYZ".

The domain-specific orthodontic treatment language may include comments that are not parsed by the orthodontic treatment planning algorithms, and are only used for communication with the user or other stakeholders.

Figure 4:
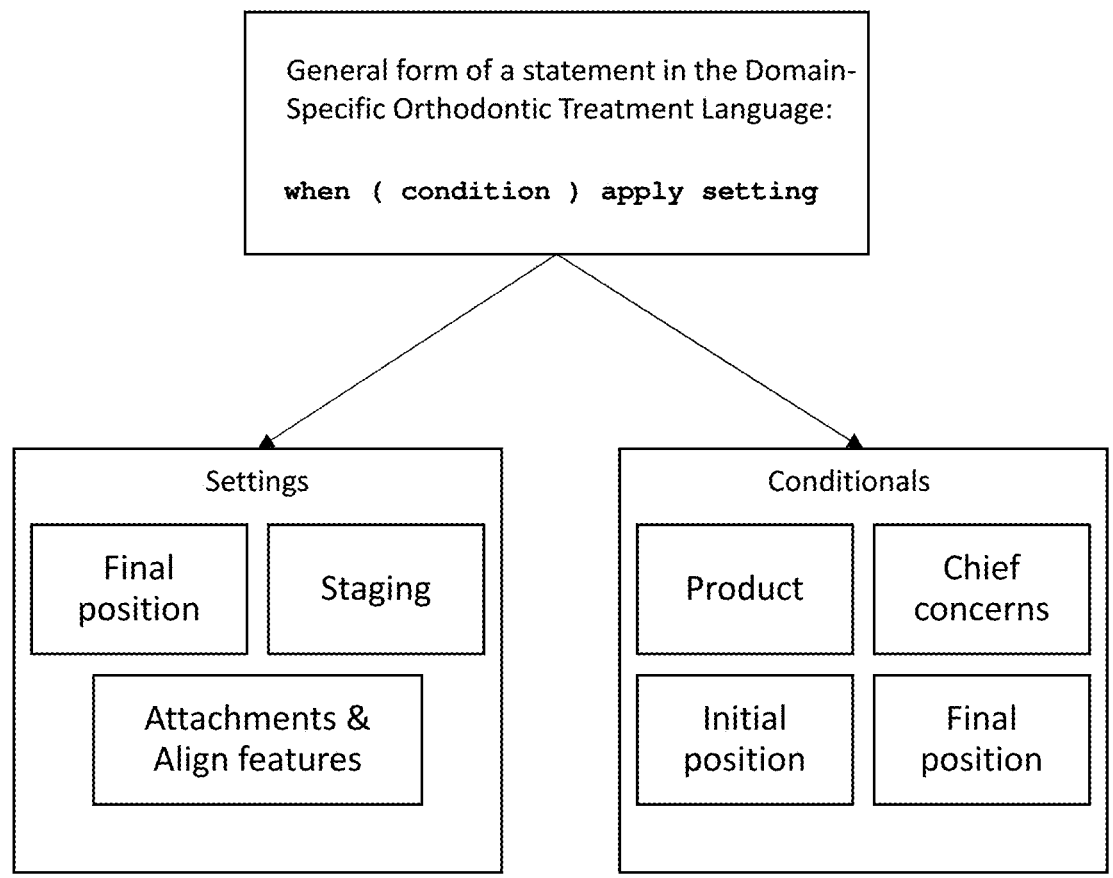
FIG. 4 is diagram showing an example of elements of a domain-specific orthodontic treatment language.

For example, FIG. 4 shows an example of overview of a general statement of a domain-specific orthodontic treatment language, showing various settings (e.g., positions) and conditionals. The domain-specific orthodontic treatment language is particularly well suited and specifically configured to include and encode user-specific preferences for orthodontic treatments. FIGS. 5A-5B, 6A-6B, 7A-7B, 8A-8B and 9A-9B illustrate example of a the kinds of parameters that may be considered user preferences and may be directly encoded and referenced in the domain-specific orthodontic treatment language.

For example, FIGS. 5A-5B show an example of a posterior cross-bite preference that may be set by the domain-specific orthodontic treatment language. FIG. 5A shows the default preference, in which the orthodontic treatment planning engine(s) will automatically try and improve the posterior cross-bite, as shown. Alternatively, the user may select to not improve the posterior cross-bite, as shown in FIG. 5B, but instead may maintain it.

In FIGS. 6A-6B the domain-specific orthodontic treatment language may allow the user to indicate a preference for include bite ramp attachments on the premolars or not. In FIG. 6A, the default is not to include premolar bite-ramp attachments; while in FIG. 6B premolar bite ramp attachments are included. In some variations, as in any of the preferences, the user may select one or more conditions under which the orthodontic feature (e.g., premolar bite ramps in this example) are included or not included. For example, the user may specify that premolar bite ramps are to be included in all cases except where there is an open bite and rotated laterals.

FIGS. 7A-7B illustrate the preference options for the domain-specific orthodontic treatment language regarding the position of attachments on the patient's teeth. In this example, the default preference may be to center the attachments (which may anchor or couple with sites on the dental appliance to help retain the appliance on the teeth), as shown in FIG. 7A. The user interface may show rotation (degrees x, y, z), crown translation (x, y, z mm), root translation (e.g., x, y, z mm), root apex movement (x, y, mm), FACC measurements (medial to distal width, buccal to lingual width, mm), and/or attachment (type, description, visibility), etc. In some variations the user may indicate in the domain-specific orthodontic treatment language that the attachments should be placed as close to the gingiva as possible, as shown in FIG. 7B.

FIGS. 8A-8B illustrate examples of preferences for target overbite correction in the domain-specific orthodontic treatment language. For example, in FIG. 8A, the default 806 parameter is that the target overbite may be between, e.g., 1.3 and 1.6 mm (in FIG. 8A, the final position is 1.45529 mm), e.g., about 1.5 mm. The user may select an alternative range. For example, the user may select in the domain-specific orthodontic treatment language a target overbite of a given value in mm (e.g., about 0.1 mm, 0.2 mm, 0.3 mm, 0.4 mm, 0.5 mm, 0.6 mm, 0.7 mm, 0.8 mm, etc.). The user interface may display sate (initial, auto-setup and final, in mm). In FIG. 8B, the target ideal overbite 808 $f$ a given value may be in mm (e.g., 0.1 mm, 0.2 mm, 0.3 mm, 0.4 mm, 0.5 mm, 0.6 mm, 0.7 mm, 0.8 mm, etc.)

FIGS. 9A-9B illustrate the selection of user preference of lingual bite ramp attachments in the domain-specific orthodontic treatment language. In FIG. 9A, the default preference is shown, without lingual bite ramps for lower anterior intrusion. In contrast, as shown in FIG. 9A, the user may indicate in the domain-specific orthodontic treatment language that the orthodontic treatment plan should include lingual bite ramps for lower anterior intrusion.

Multiple other preferences and conditions may be indicated by the domain-specific orthodontic treatment language. The table shown in FIGS. 10(*i*)-10(*vi*) illustrates examples of the grammar and syntax for a domain-specific orthodontic treatment language. This table illustrates conditional (e.g., "if") language using the orthodontic treatment specific context, as well as numerical ranges, teeth ranges, and list.

FIG. 11 is an example of a portion of a treatment template that is written in a domain-specific orthodontic treatment language. In this example, the treatment template is both human readable (describing a public protocol with user-specific preferences for points, passive aligners, arch expansion, leveling, trimming, etc.). This treatment template may then be parsed into a set of orthodontic treatment planning instructions.

Figure 12A:
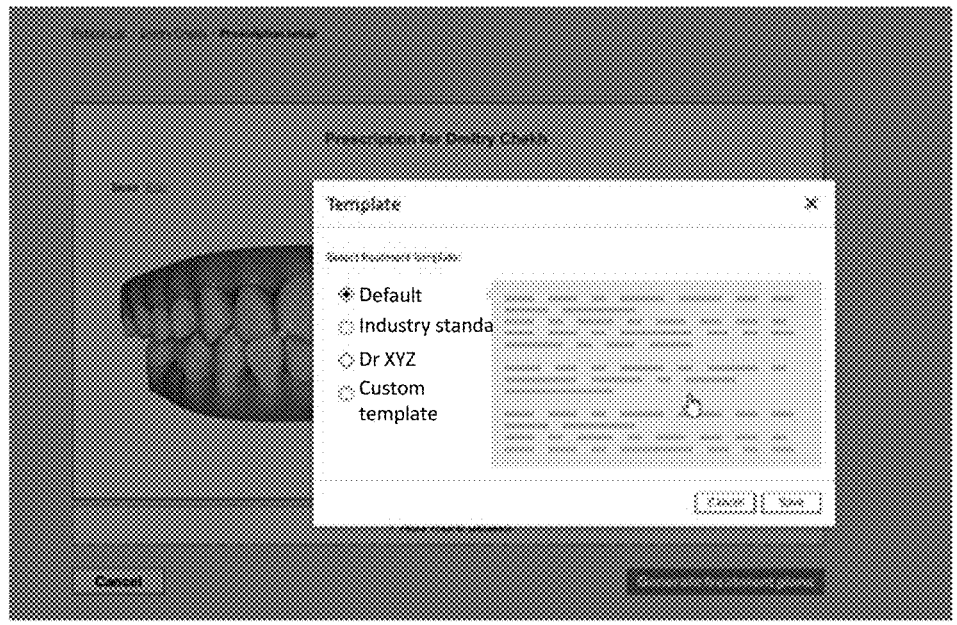
FIG. 12A is an example of a user interface for creating a treatment template.
Figure 12B:
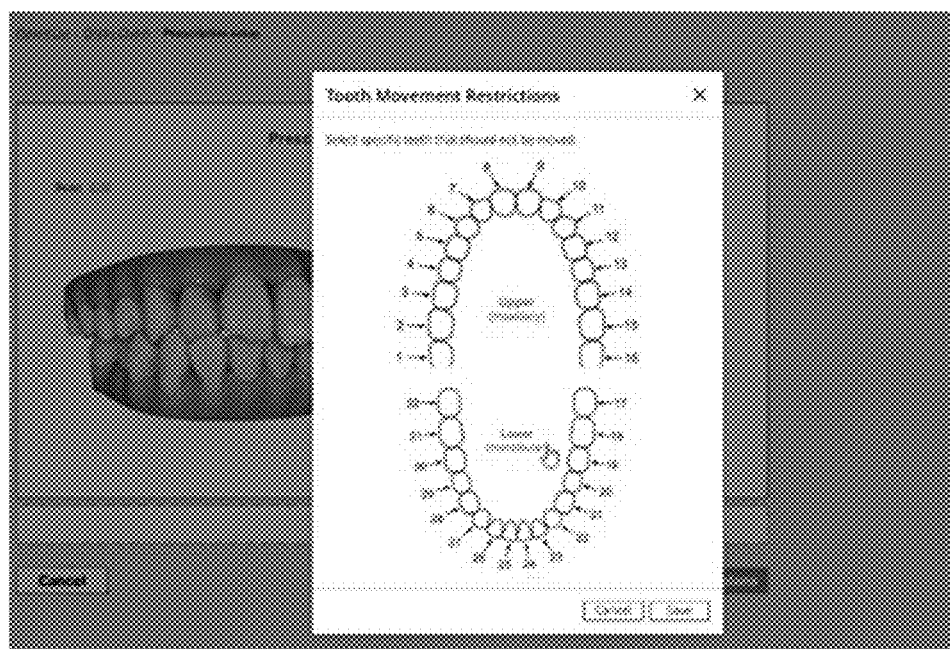
FIG. 12B is an example of a user interface for creating a treatment template.

The user and/or technician may set up the treatment template. For example, FIGS. 12A-12B illustrate examples of user interfaces for making or modifying a treatment template. In FIG. 12A, for example, the user may select to generate a new template as a default template (shown selected), as an industry standard template, as a specific "opinion leader" template, or as their own custom template. The user interface may allow them to input their choice, and the starting template may then be provided, so that they can modify it, and save is for future use (they may also use it as-is).

A system may include additional user interfaces that allow the user to select parameter preferences. For example, FIG. 12B shows a user interface that the user and/or technician may select tooth movement restrictions for the treatment. The user interface may automatically encode the selection to the treatment template in the domain-specific orthodontic treatment language.

In general, the domain-specific orthodontic treatment language may include special directives to support dynamic creation of graphical user interface (GUI). For example, template parameters may be declared in the treatment template script, and may enable doctors to customize a template from the library of available templates, and create a derivative of it. For instance, if a template includes the instruction "expose template_parameter (arch_form)", a UI control shall may be automatically generated, which allows the user to select a preferred arch form, when deriving a template.

Case parameters may be declared in the template script, and may enable users (e.g., doctors) to prescribe clinical parameters relevant to their template, for every case using the treatment template. For example, if the treatment template script includes the instruction "expose case_parameter (ap_correction)", a UI control may be generated, allowing the user to enable or disable AP correction for each new case.

Figure 13C:
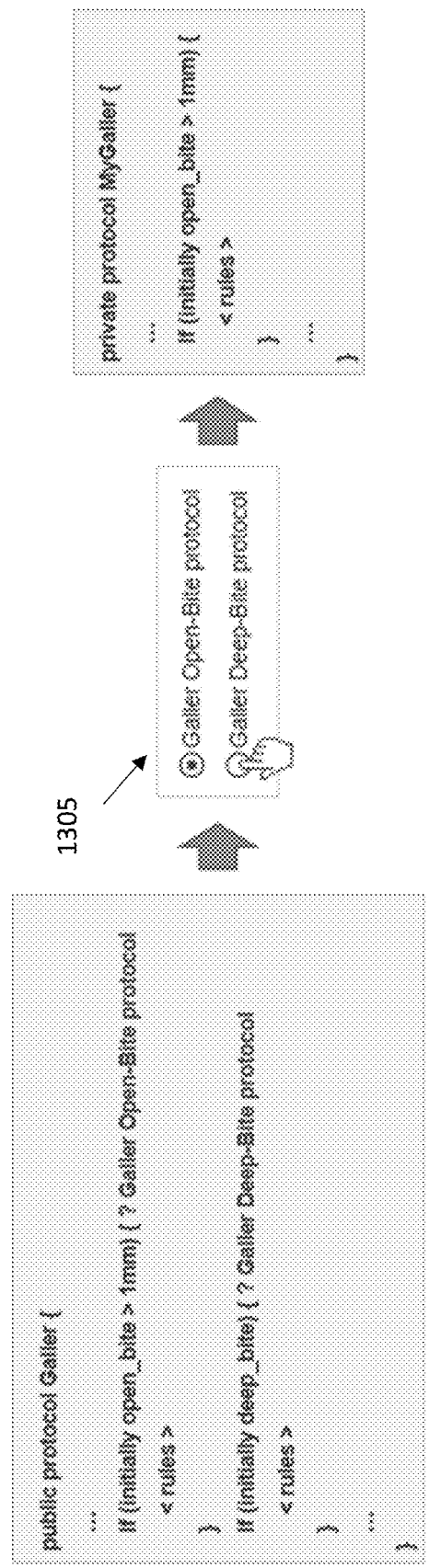

For example, FIGS. 13A-13D illustrate user interfaces for modifying existing treatment templates. In FIG. 13A, a treatment template in a domain-specific orthodontic treatment language may be customized by including in the domain-specific orthodontic treatment language a term (directive) that calls a graphical user interface (GUI 1305) for selecting parameters for the protocols. The treatment template shown on the left in the domain-specific orthodontic treatment language includes a term "?" that triggers a graphical user interface to prompt the user (or a technician working with the user) to enter a value, in this example, anterior IPR limits, from a list of possible values. The user may then select the value (e.g., "0.50 mm") and the value will be automatically replaced in the treatment template, as shown on the left. Thus, in some variations, the domain-specific orthodontic treatment language may include special terms or directives that indicate which parameters may be entered through a specific GUI and may call the GUI when the treatment template is reviewed by the user. The outcome of calling the GUI (the user selection) may be entered and the revised version of the original treatment template may be stored with the replacement term. This approach may enable control of which parameters are customizable. The GUI may be dynamically created from a collection of ready-made controls. The GUI control may consist of one or more traditional dropdowns and checkboxes, or specially designed graphical controls.

In some variations, the customization may be part of a standard configuration, rather than specifically called-on (e.g., invoking a GUI) based on the domain-specific orthodontic treatment language. For example, FIG. 13B illustrates a variation in which the protocol maybe modified by adding instructions on top of the existing protocol. Protocol customizations may be expressed as additional constraints on top of an existing template, using the semantics for overriding instructions. For example: If the base template has "enable passive_aligners" and the override contains "disable passive_aligners", the override wins. Similarly, any pair of conflicting instructions may have a predetermined winner. In FIG. 13B, for example, the original treatment template indicates that the interproximal reduction limit for anterior teeth should be at a maximum of 0.30 mm ("limit ipr (teeth: anteriors, max_amount: 0.30 mm)"); the user interface allows the user to enter a new amount (0.50 mm), and this new value overrides the original value.

In some variations the treatment template may include alternative variations of preferences that may be turned on or off by the user and/or technician. For example, the domain-specific orthodontic treatment language may include directives to enable/disable portions of the treatment template, which may be alternative preferences. For example, FIG. 13C illustrates an example of a treatment template that includes a directive ("?") that invokes a GUI 1305 that toggles between two (or more) alternatives; in this example, using an open-bite protocol or using a deep-bite protocol. The final version of the template may remove the disabled portion (and the directive), as shown on the right side of FIG. 13C.

Figure 13D:
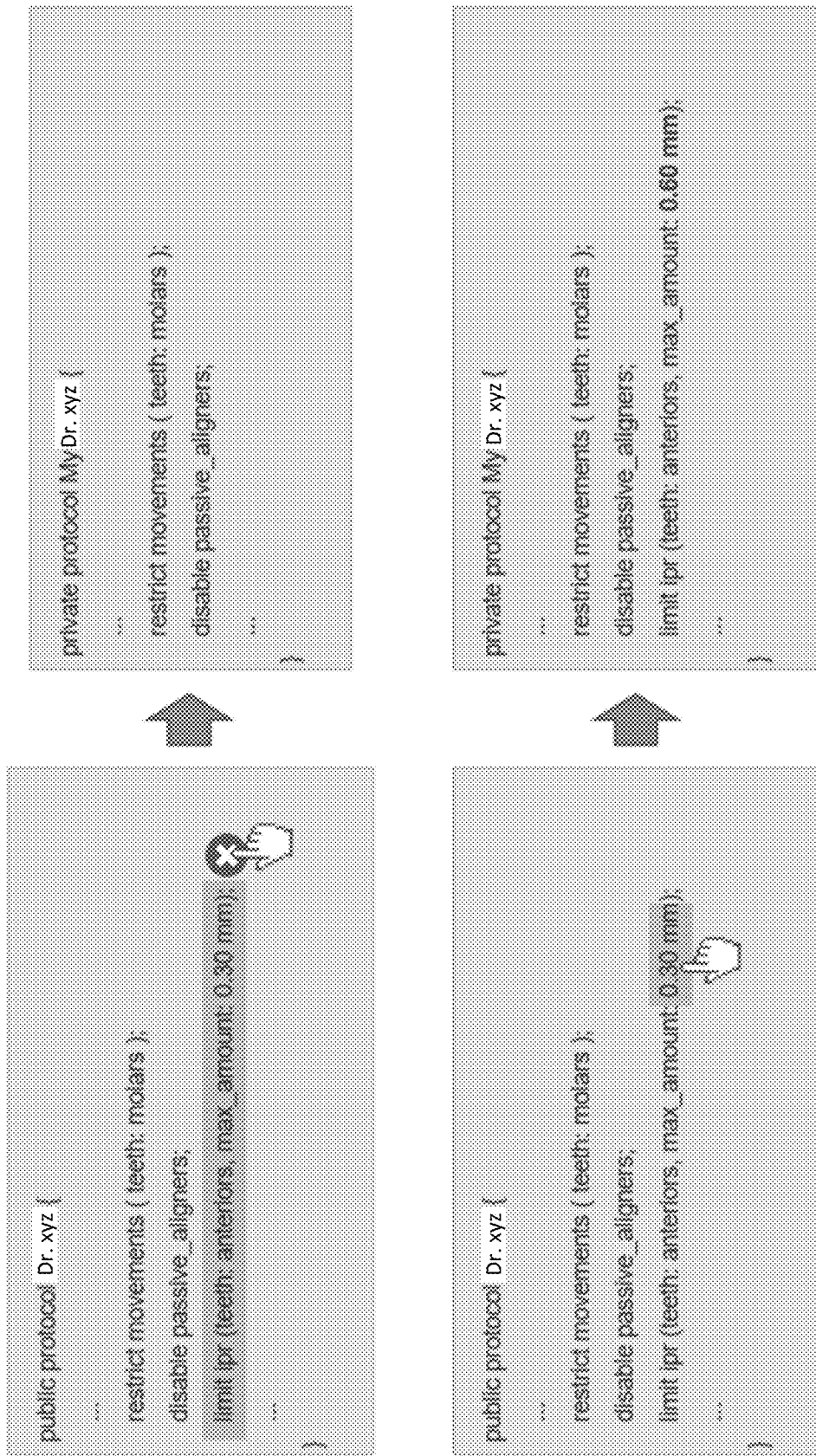

Another customization approach is shown in FIG. 13D. In this example, the user sees the treatment template code, and gets limited capabilities for manipulating it directly. Edits may include deletion and parameter modification. Thus, the user interface may show the human-readable domain-specific orthodontic treatment language of the template, and provide user controls for removing or modifying it. In FIG. 13D, the upper left shows the unmodified treatment template; and the cursor highlights the option for removing the parameter (shown by the selectable "X" and the highlighting); the upper left shows the resulting treatment template with this parameter removed. In FIG. 13D, on the lower left, the parameter value is shown highlightable when the cursor runs over it; the user may then directly indicate the new value, as shown in FIG. 13D on the right.

In these example, the outcome is expressed in the domain-specific orthodontic treatment language, and can be processed like manually-coded protocols. Alternatively or additionally, an intermediate data format may be used, e.g., for storing the editable parameter values, so that these can be modified later.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

In use, the user may select the orthodontic treatment plan to be applied to a particular patient. As a patient's cases is submitted for orthodontic treatment planning, the user may select a template to apply to the case. For example, the user may choose from one or more templates, some of which are public templates (available to a number of users), and some of which are private (which may be, e.g., authored by the same user). The template, in the domain-specific orthodontic treatment language, may then be parsed, and the orthodontic treatment planning engines (algorithms) may invoke the rules described in the language, during various steps of the computation (e.g., final positioning, staging, attachments and align features).

In general, each invocation of a template may include a log trace of the rules that were fired and the settings that were used, to enable troubleshooting in case the user is not satisfied with the outcome.

Parsing

The treatment template may be translated into a format that may be received and understood by the orthodontic treatment planning engine. Thus, the domain-specific orthodontic treatment language may be parsed into the orthodontic treatment planning instructions either before or after passing to the orthodontic treatment planning engine(s). In some variations a separate module (e.g., a domain-specific orthodontic treatment language parsing engine) may be used before passing to the orthodontic treatment planning engine. Alternatively, the orthodontic treatment planning engine may be configured to parse the domain-specific orthodontic treatment language.

Figure 14A:
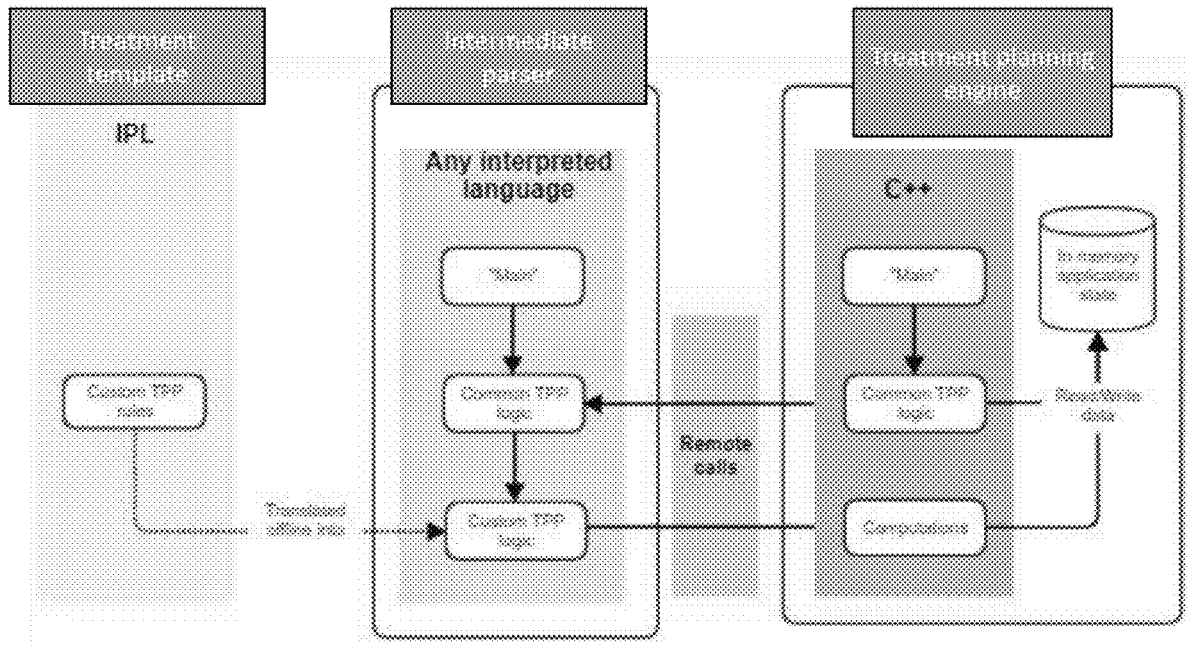
FIGS. 14A-14B illustrate examples of parsing of a treatment template written in a domain-specific orthodontic treatment language.

For example, FIG. 14A is an example of a system including a domain-specific orthodontic treatment language parsing engine ("intermediate parser") that external to the orthodontic treatment planning engine. In this variation, the intermediate parser is used to parse the domain-specific orthodontic treatment language ("IPL") of the treatment template. The orthodontic treatment planning engine does not need to parse the treatment template, as it is pre-parsed by the intermediate parser. Alternatively, the treatment template could be translated into an embeddable language (e.g., python/LUI).

Figure 14B:
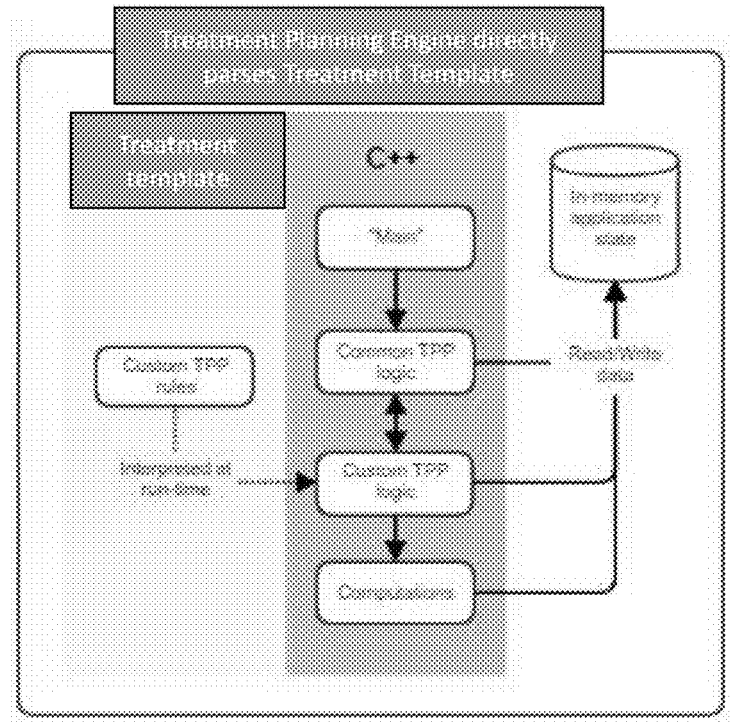

Alternatively, in FIG. 14B the orthodontic treatment planning engine includes a parser for parsing the domain-specific orthodontic treatment language of the treatment template. In this variation, the orthodontic treatment planning engine directly parses the treatment template (in the domain-specific orthodontic treatment language). For example, either the orthodontic treatment planning engine includes a parser that parses it into the logic (shown in FIG. 14B) or the treatment template is wrapped with a parsed version when it is generated (not shown).

Figure 15:
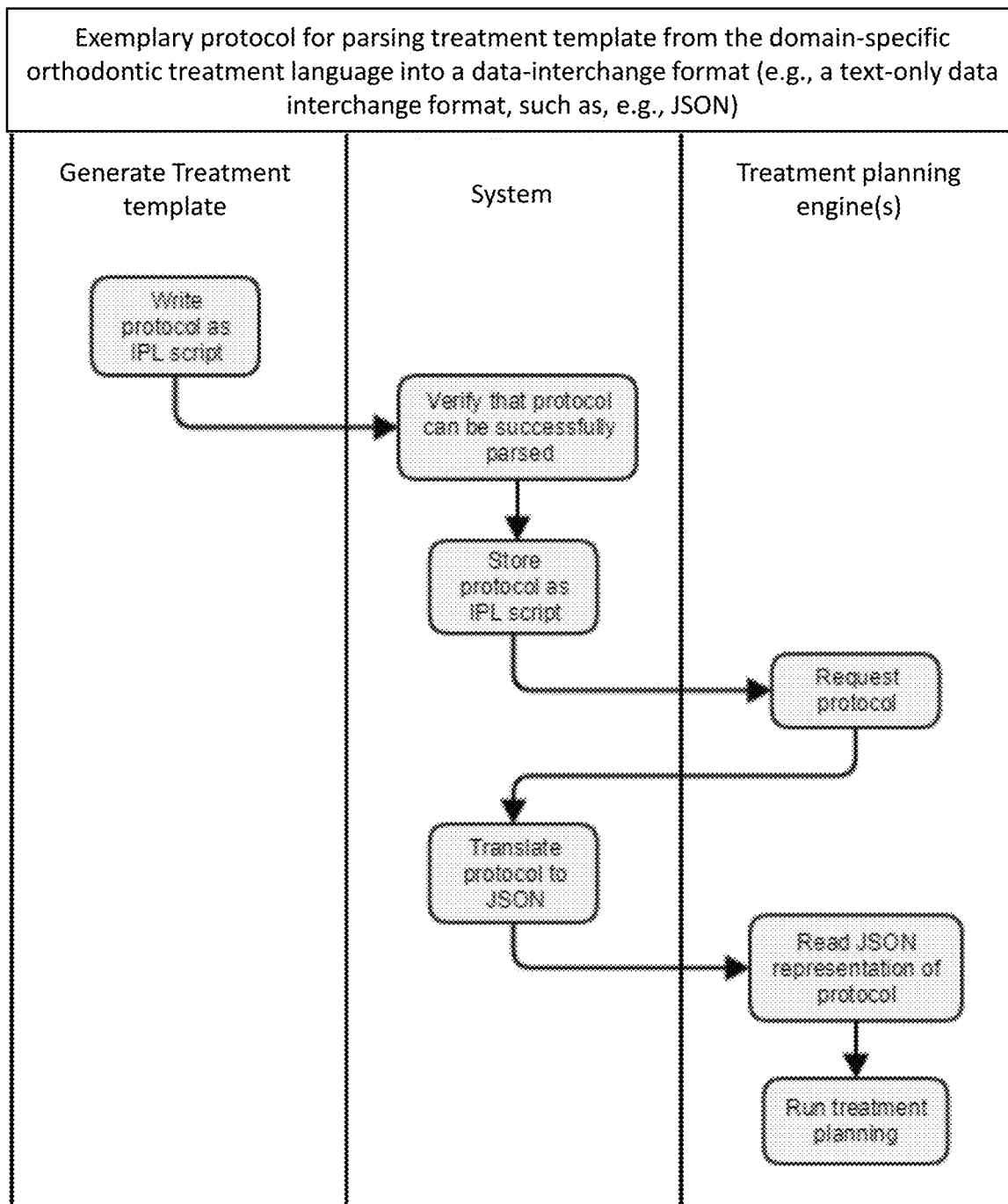
FIG. 15 is a diagram illustrating an example of using a treatment template in a domain-specific orthodontic treatment language to generate one or more orthodontic treatment plans.

While the domain-specific orthodontic treatment language is designed to be concise and easy to read, the orthodontic treatment planning engine may use an encoding into a data-interchange format, such as a text-only data-interchange format, e.g., JSON. Thus, any of the systems described herein may convert the domain-specific orthodontic treatment language into, e.g., a JSON format. The Treatment templates may be coded and scripted into the domain-specific orthodontic treatment language, and stored, as source code, in the domain-specific orthodontic treatment language. The system may translate this domain-specific orthodontic treatment language into JSON format that the consumption of the orthodontic treatment planning engine(s) (e.g., "Treat"). This is illustrated in FIG. 15. For example, in FIG. 15, the figure shows the flow of information from the treatment template (encoded in the domain-specific orthodontic treatment language) to the other portions of the system, and the orthodontic treatment planning engine(s).

Voice Control for Treatment Planning

Any of the methods and apparatuses (e.g., systems, including automated systems) described herein may include voice control. Thus, in general, the methods and apparatuses described herein may include voice control. The use of voice input, including voice recognition, may be particularly helpful for systems, including those described herein, in which the user may provide input into the system that may then interpret the input and covert it to a machine-actionable instruction (e.g., a domain-specific orthodontic treatment language).

For example, precise panning of teeth movements sometimes require movement and rotation of teeth up to 0.1 mm or 1 degree of rotation. This may be accomplished, for example, using 3D editing tools that may be part of a system such as those described herein, including direct doctor input. Such input may require training and may have a learning curve to start using them properly and there may be users who are not able to overcome this barrier. Voice commands may provide a more natural, and more automated, way of giving commands to a treatment planning system. In particular, the system may provide immediate feedback allowing the user to correct, adjust or accept a command. Further, the use of voice feedback may help normalize or standardize interaction with the systems described herein. Finally, the voice command systems described herein may not require precise manipulations, but may allow fine grained control of the movements. In particular, the use of voice commands may provide automatic, real-time assistance in treatment planning. For example a voice command by a user to "move by 1.2 mm" the apparatus may move a tooth exactly by 1.2 mm, without requiring the user to learn how to perform precise manipulations with mouse control and practice manual skills. Treatment planning using voice control may be used for formulating the goals and constraints of the treatment, in addition to allowing specific (e.g., movement) instructions.

In general, voice commands may be implemented at any portion, or all of, the treatment planning process. For example, information provided by the user during treatment planning may include one or more of: initial position of teeth (initial data), treatment goals (what to achieve), treatment constraints (what not to do, what to necessarily do), treatment schedule (when to do). A treatment planning engine may construct a treatment plan to present to a user based on this information, as described above. Voice control system (voice control sub-system) may be part of the treatment planning process, and may allow the user to enter information, and/or modify information such as the final position itself or one of the underlying characteristics (goals, constraints, schedule) of the treatment. After at least one of the characteristics is changed, a new treatment plan may be presented to a doctor.

Figure 31:
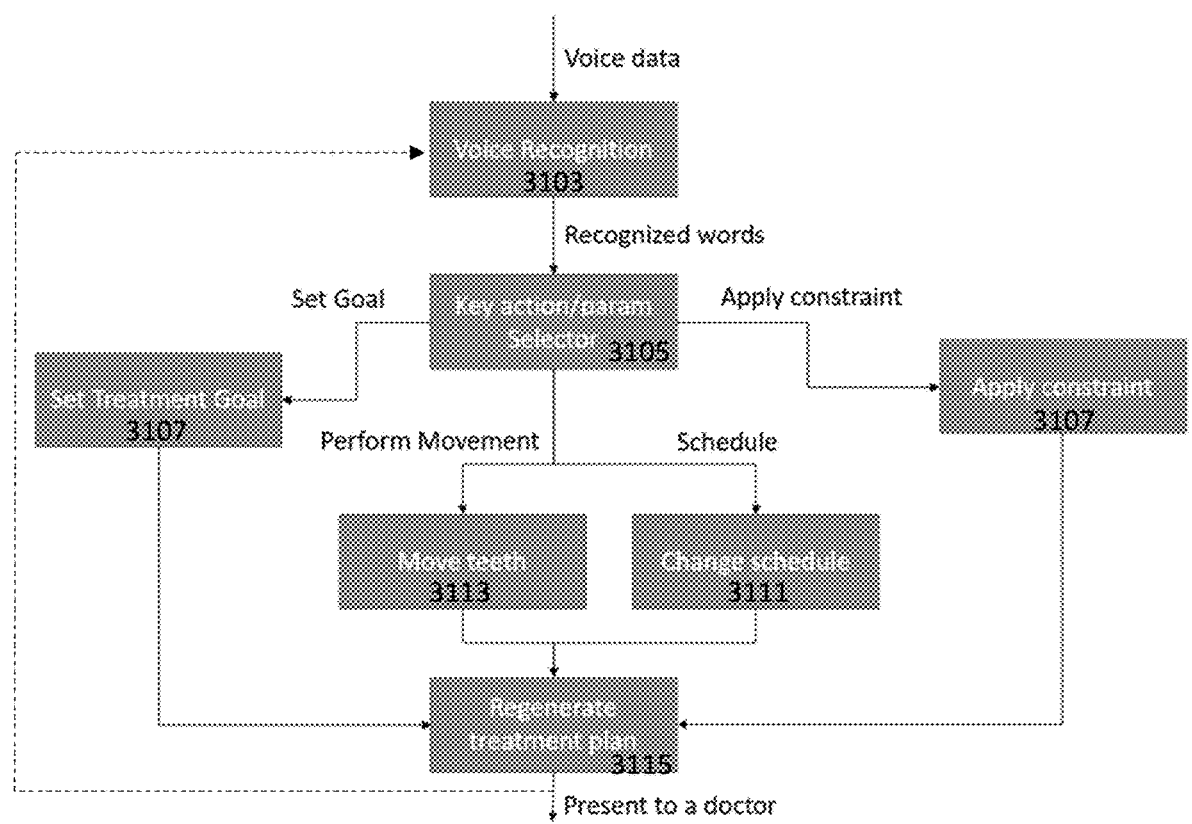
FIG. 31 is a chart illustrating the use of voice recognition to assist in treatment planning.

FIG. 31 illustrates one example of a process for applying or using voice recognition as part of a dental treatment plan, described herein. In this example, the method (or an apparatus configured to perform the method) receives an initial state (e.g., an initial treatment plan stat, such as an initial position of the teeth, treatment goals, treatment constraints and required schedule, etc.), as well as a voice command 3103 from a user (e.g., doctor, dentist, etc.). Words may be recognized and may be specific (e.g., trained on) the domain-specific orthodontic treatment language. The method or system may generally provide update based on the voice command (e.g., may update the treatment goals, schedule, and/or may provide a new treatment plan reflecting all of the point above, etc.).

In operation, the method or system may detect a main action of the received (input) statement and associated parameters. Examples of key actions and parameter selection may include performing specific movement 3113 for a given tooth (or teeth). Examples may include: "Move upper left $2^{nd}$ molar distally by 0.2 mm" (action: "Move"); "Upright upper right canines" (action: "Upright"); "Upright upper canines" (action: "Upright"); "Procline upper centrals by 10 degrees" (action: "Procline"). Another key action and parameter selection may include setting goals 3107 of the treatment to achieve. Examples may include: "Achieve overbite of 1 mm" (action: "Achieve"; "Achieve overjet in 1-2 mm range" (action: "Achieve"; "Set interincisal angle of 130-135 degrees" (action: "Set"). Another key action and parameter selection may include setting constraints 3109 for the treatment plan (which may be expressed via a negative). Examples may include: "Do not fix cross-bite" (action: "Do not fix"); "Maintain molar class on left side" (action: "Maintain"); "Do not move premolars" (action: "Do not move"); "Do not move lower incisors labially" (action: "Do not move"). Another key action and parameter selection may include scheduling activities 3111 in time (when to do certain things). Examples may include: "Perform extraction on the second stage" (action: "Perform"); "Perform IPR every 12 stages" (action: "Perform"); "Remove all features before overcorrection aligners" (action: "Perform").

Action and parameters identification may be performed by machine learning (ML) algorithms and/or by algorithmic syntax analysis of the statement where words are assigned with a certain weight to reflect their significance. "Voice Recognition" block may be implemented with any homemade or commercial software available in the market.

Based on the action and parameters, classified as movement, goal, constraint or schedule, as described above, the respective change may be made in a treatment plan description. After that, the treatment plan may be regenerated 3115 based on a new data input. This cycle may be performed arbitrary amount of times.

Examples

The methods and apparatuses described herein may be used for treatment planning that is customized for a particular user as well as a particular patient. As described above, the user may provide instructions that are in plain (e.g., natural) language and the techniques and apparatuses described herein may interpret these instructions for treatment planning. In addition, these methods and apparatuses may be used to automate or semi-automate treatment planning by using information, such as user preferences, when customizing treatment plans for a particular user as the user determines how best to treat individual patients.

The domain-specific treatment language (e.g., a domain-specific orthodontic treatment language) described above, may be implemented as part of an automated or semi-automated treatment planning system that may reduce or eliminate misinterpretation of doctor's instructions and may dramatically reduce the time necessary to create a treatment plan. For example, a treatment planning system may be used by both a user (e.g., doctor, dentist, orthodontist, etc.) and a technician and may provide tools for describing, creating and validating a doctor's treatment plan (e.g., protocol) using the domain-specific (e.g., orthodontic) treatment language.

A treatment protocol, which may be applied to generate a treatment plan in conjunction with a digital model of a patient's teeth, may be generated for a user when the user initially describes their preferences in a free text instruction. These free text instructions may be applied to generate a treatment plan. For example, a technician may interpret these instructions. As mentioned above, without the use of a domain-specific orthodontic treatment language and tools to apply the domain-specific orthodontic treatment language to generate and validate treatment protocols, this process may allow misinterpretation of the user's instructions. Described herein are tools for automating or semi-automating the generation of user-customized treatment protocols using the domain-specific orthodontic treatment language. The automated or semi-automated systems for generating a user-customized treatment plan(s) using the domain-specific orthodontic treatment language described herein may create formalized user protocols, and may address delays in generating treatment plans. The use of the domain-specific orthodontic treatment language in the context of an automated application or system may also make the process of finalizing user preferences more efficient and reliable.

The automated/semi-automated systems and methods for generating treatment plans described herein use a domain-specific orthodontic treatment language editors that supports the syntax of the domain-specific orthodontic treatment language. These systems and methods may include one or more user interfaces for reviewing and managing user-specific treatment protocols (e.g., generic treatment plans that may be applied to form a patient-specific treatment plan). These systems may also provide a treatment protocol/treatment plan editor (using the domain-specific orthodontic treatment language), and may manage user-specific protocols. These systems and methods may generally provide validation of user protocols and review of treatment plans corresponding to these protocols.

In general, there are many variables contributing to the variety of treatment plans that may be used to treat the same patient. User treatment plans may vary depending on the level of user's experience, the user's education, the user's personal style and beliefs in treating the patient. Thus, the same patient might get different treatment from different users.

In practice a user may provide her or his treatment preferences by filling out an RX form for each case, which may include a great number of treatment options; however, such forms cannot include all of the user's possible instructions, and thus additional instructions may be provided in plain text. The variety of instructions that users may provide when requesting treatment plans may require multiple iterations of review and validation by the user before finalizing a treatment protocol that may be used to generate a treatment plan. The methods and apparatus for generating treatment plans described herein may dramatically improve the speed and accuracy of this process.

The methods and apparatuses (e.g., systems) described herein may use a domain-specific treatment language (e.g., a domain-specific orthodontic treatment language) to describe and rapidly modify treatment protocols into programming scripts that may be fully automated by treatment planning software to generate a treatment plan when applied to a digital model of a patient's teeth. This script is called doctor's protocol.

Figure 16:
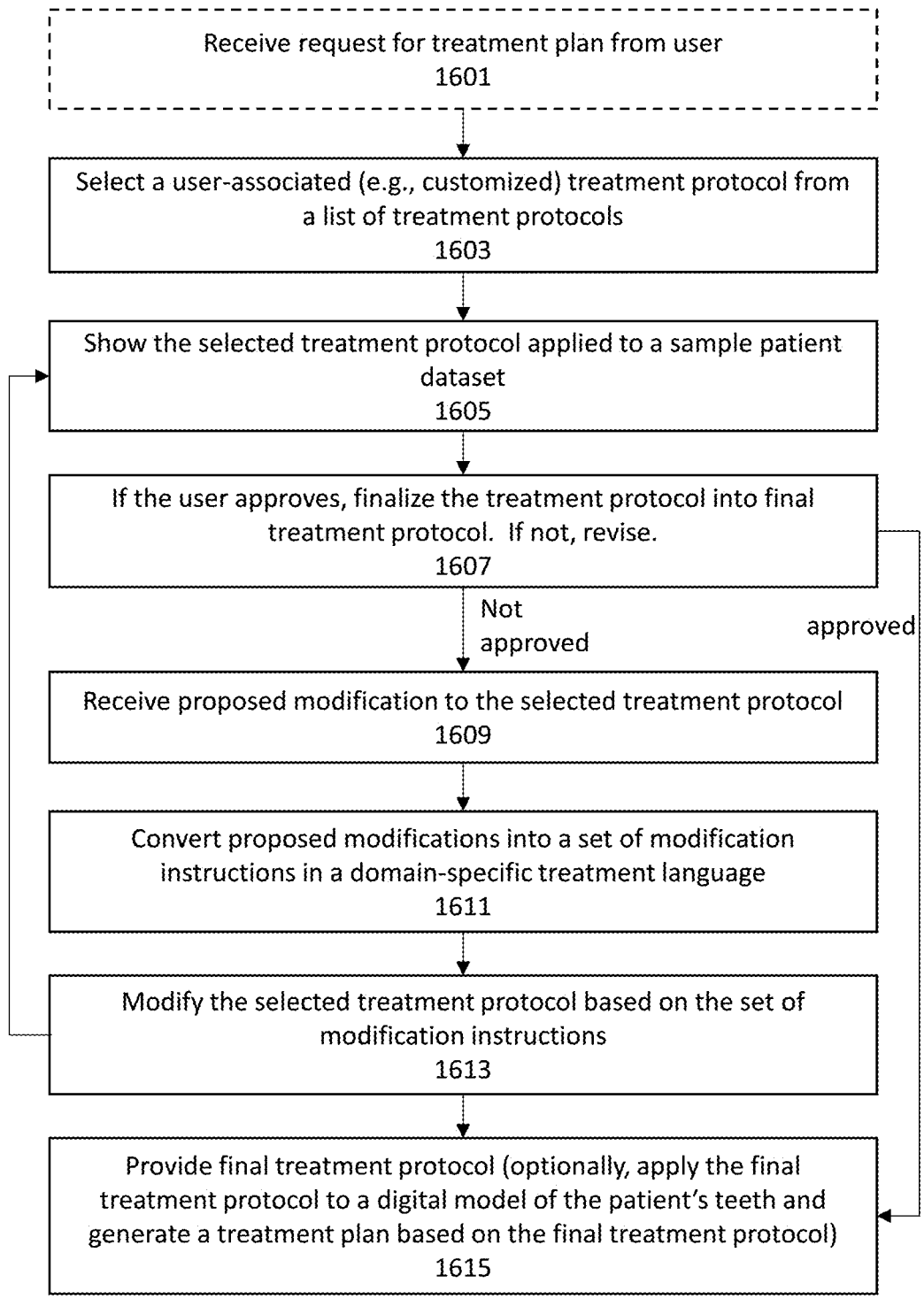
FIG. 16 illustrates one example of a method of planning a treatment for a patient using a domain-specific orthodontic treatment language system.

FIG. 16 illustrates one example of a method of planning a treatment for a patient in which a domain-specific orthodontic treatment language is used to rapidly and effectively generate a treatment protocol and therefore a treatment plan. As shown in FIG. 16, the method may begin when the user requests a treatment plan 1601 specific to a patient. This request may be provided to the system (e.g., a system for generating a treatment plan); in some variations the user request may include a digital model of the patient's teeth. Alternatively, the method may begin without a specific treatment request, but in anticipation of a user requesting a treatment plan for a patient, in order to add the user to the system for future treatment plan generation.

A user-associated (e.g., customized) treatment protocol may then be selected, either by the user, by a technician, or automatically (e.g., by the system), and this user-associated protocol may be received by the system. In some variations the user may select one from a list of user-associated treatment protocols that they have used in the past. The system may provide a list of user-associated protocols that the user may choose from 1603. The user-associated treatment protocols may therefore be specific to (e.g., customized to) the user based on previous user cases. Thus, the system may have a database (e.g., data store) of historical treatment protocols indexed by the user.

Alternatively, if no user-specific protocols are available, or none are selected, then a user-specific protocol may be generated. For example, a user-specific protocol may be generated based on the user's existing preferences, which the system typically has access to (or has already received). In some variations a user or technician (or the system itself) may choose a treatment protocol from another user as the user-associated treatment protocol; the treatment protocol from another user may be chosen based on similarities, such as preference similarities, with the current user, and/or based on a choice made by the current user.

Once a user-associated treatment protocol has been selected, it may be further customized. For example, the system (or a technician aided by the system) may modify the user-associated treatment protocol based on the user's preferences. User preferences may be provided at the time of the request and/or may be accessed and/or may update stored user preferences, e.g., from a database of user preferences (e.g., a data store of user preferences). User preferences may include any of the treatment preferences (such as use, type, and/or orientation of attachments, interproximal reduction use and/or stage of use, extraction(s), etc.). In particular, the user-associated treatment protocol may be modified to include any treatment instructions provided by either or both the prescription form and/or any free-form instructions transmitted with the case.

The user-associated treatment protocol may then be used to generate a mock or validation treatment plan using one or more sample patient datasets (e.g., digital model of a sample patient's teeth). Alternatively, in some variations the data set may be actual patient data (digital model of the patient's teeth). The resulting test/validation treatment plan may then be displayed and used to determine if the user-associated treatment protocol is correct, or if it should be modified. For example, the user and/or technician may be presented with a display of a treatment plan implementing the user-associated treatment protocol, showing the selected treatment protocol (the user-associated treatment protocol) as applied to the teeth of one or more sample patients from a library of sample patients' teeth 1605. The display may show the final stage or stages of the treatment plan, and/or multiple stages of the treatment plan, or may allow the user and/or technician to scan through the stages of the treatment plan to review the selected treatment protocol.

In general, the treatment protocol may be expressed in the domain-specific orthodontic treatment language. In some variations the system may also automatically determine if the treatment protocol is correct, e.g., by automatically reviewing the treatment protocol using the domain-specific orthodontic treatment language. Identified problems may be displayed or flagged or otherwise marked for correction, and/or in some variations automatically corrected.

The user and/or technician may indicate if the current selected treatment protocol, which resulted in the test treatment plan, is correct, or if it should be modified. If the user and/or technician indicates that the treatment protocol is sufficient, the selected treatment protocol may be finalized (approved). Alternatively, if the selected treatment protocol is not final, the user and/or technician may further modify it 1607. For example, the system may receive proposed modifications to the selected treatment protocol from the user and/or technician 1609. These proposed modifications may be converted into a set of modification instructions in the domain-specific orthodontic treatment language as described above 1611. The set of domain-specific modification instructions may then be used to modify the selected treatment protocol to form a putative final treatment protocol 1613. The putative final treatment protocol may then be used as the selected treatment protocol and again used to generate a test treatment plan using a sample patient dataset, as described above 1605, the results displayed and analyzed/approved as mentioned above, and further approval or modifications made. This entire process may be iterated until the treatment protocol is finally approved. In some variations, this final treatment protocol may then be stored (e.g., as a new user-associated treatment protocol) and used in the immediate case and/or in a future case to generate, in conjunction a digital model of a patient's teeth, a treatment plan 1615. For example, the system may generate a treatment plan using the final treatment protocol.

A system for performing these methods may be referred to as a domain-specific orthodontic treatment language workplace application ("application"). This application may be configured as an integrated development environment (IDE) that may assist (e.g., a technician) in transforming protocols written by users into working protocols expressed in the domain-specific orthodontic treatment language so that they may be quickly and accurately processed, including in real-time or near-real-time.

Figure 17:
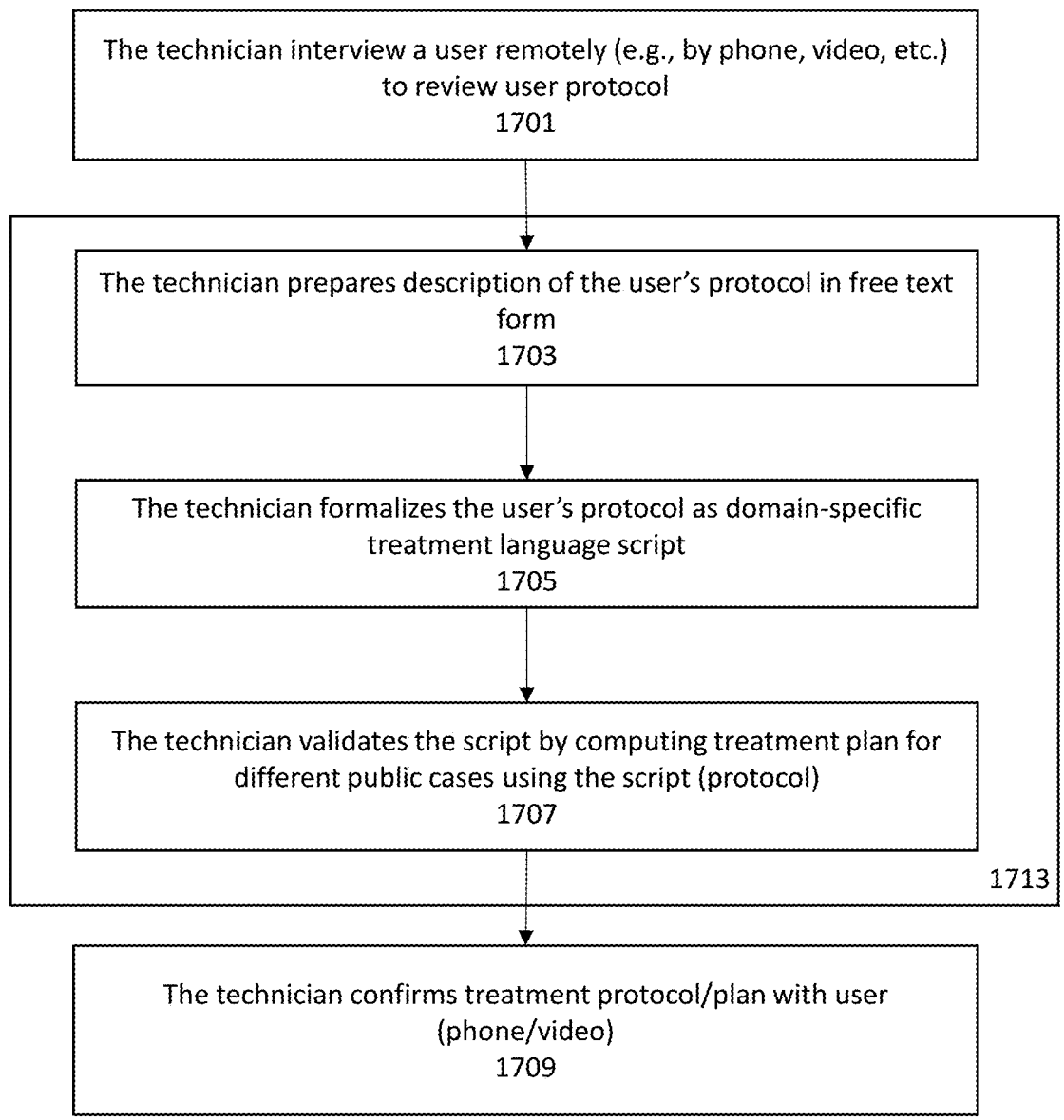
FIG. 17 illustrates another example of a method or process of creating a user-specific treatment protocol.

FIG. 17 illustrates another example of a method or process of creating a user-specific treatment protocol. In this example, the application may be constructed by first interviewing a user or perspective user to review a user protocol 1701. This may be done manually or semi-automatically, e.g., aided by the one or more systems described. Thus the user preferences may be expressed in the domain-specific orthodontic treatment language. The application 1713 may then be used to generate the user-associated (e.g., "selected") treatment protocol, including modifying or customizing it. For example, the application may assist the technician in forming a user-specific protocol from the free text or prescription form 1703 and expressing it in the domain-specific orthodontic treatment language. This may include modifying an existing user-associated treatment protocol, as described above. The technician may formalize/finalize the user-specific protocol 1705 using the domain-specific orthodontic treatment language (forming a "script" of the user-specific/selected protocol). The protocol ("script") may then be validated by comping one or more treatment plans using the protocol and one or more different public cases 1707, as described above. The technician may themselves review the resulting treatment plan and/or they may consult with the user to validate 1709. Further modification may be made after the validation step and the process repeated until it is finalized.

Once the protocol has been validated and finalized, it may be used to generate one or more treatment plans. Since the protocol ("final treatment protocol") is expressed in the domain-specific orthodontic treatment language, it may be used to quickly and automatically generate treatment plans using a digital model of the patient's teeth. For example, as shown in FIG. 18, after finalizing the treatment protocol for a particular user, a patient may request a treatment 1801, and the user may create a case specific to the patient, selecting one of the user-specific treatment protocols to apply 1803. The user may send the request for one or more treatment plans along with the prescription preferences and a digital model of the patient's teeth 1805. The user-specific treatment protocol may be selected and modified as described above to include the user's preferences, and a treatment plan generated. Once approved, the treatment plan may be executed and the patient may receive the designed treatment plan 1807.

FIG. 19 is another schematic illustration of a method of creating and/or modifying a treatment protocol, aided by an application (e.g., a domain-specific orthodontic treatment language workplace application) such as those discussed above. In FIG. 19, the user (e.g., doctor) may request creation/modification of a treatment protocol specific to the user 1901. The system (e.g., aiding a technician) may then request instructions from the user 1903, who may then provide the instructions 1905. These instructions may include preferences 1909, and/or prescription information/free-text instructions. In some cases this may result in a full treatment protocol (e.g., expressed in the domain-specific orthodontic treatment language), in which case the treatment protocol may be further edited until it is ready to be validated. Alternatively 1911, the treatment protocol ("script") may be edited 1913, including checking for syntax errors 1915 in the domain-specific orthodontic treatment language, and the treatment protocol may then be validated 1917, as described above. If the validation is successful 1919 (e.g., if a treatment plan may be generated using a mock dataset), the user may review the validation 1921 and either submit for further modification 1923 or move ahead to use this protocol for additional cases 1925.

In this example, the user and the technician may collaborate and formalize an appropriate user-specific protocol. The system may automatically review the text instruction for each case, and may rapidly validate the treatment protocol using the planning software that may automatically apply the treatment protocol to rapidly validate the protocol. Thus, the application may deliver an effective and reliable functionality for preparing a protocol description, formalization of the protocol as a script in the domain-specific orthodontic treatment language.

FIGS. 20-25 illustrate user interfaces that may be used with the systems described herein. For example, FIG. 20 illustrates one example of an editor (e.g., a domain-specific orthodontic treatment language editor) that may be used. The protocol shown is identified by the user ("user name") and includes preferences and formal preferences, as well as comments. The description editor may be a tool for structuring a user's preferences in a form of checkboxes with free text comments, and may make it more convenient to follow the process of automation of preferences and transforming them into a domain-specific orthodontic treatment language script.

FIG. 21 illustrates one example of a user interface for a domain-specific orthodontic treatment language editor. In FIG. 21, the user interface may provide a full-code editor that supports syntax of the domain-specific orthodontic treatment language (scripting language). It makes IPL protocol creation and modification possible with advanced functionality such as syntax highlighting, syntax checking, code auto-completing, code auto-indenting and bracket matching. The technician is able to verify syntax validity of the protocol and see particular areas which contain syntax errors. In FIG. 21 the protocol example shown is expressed as a complete user-specific protocol.

Figure 22:
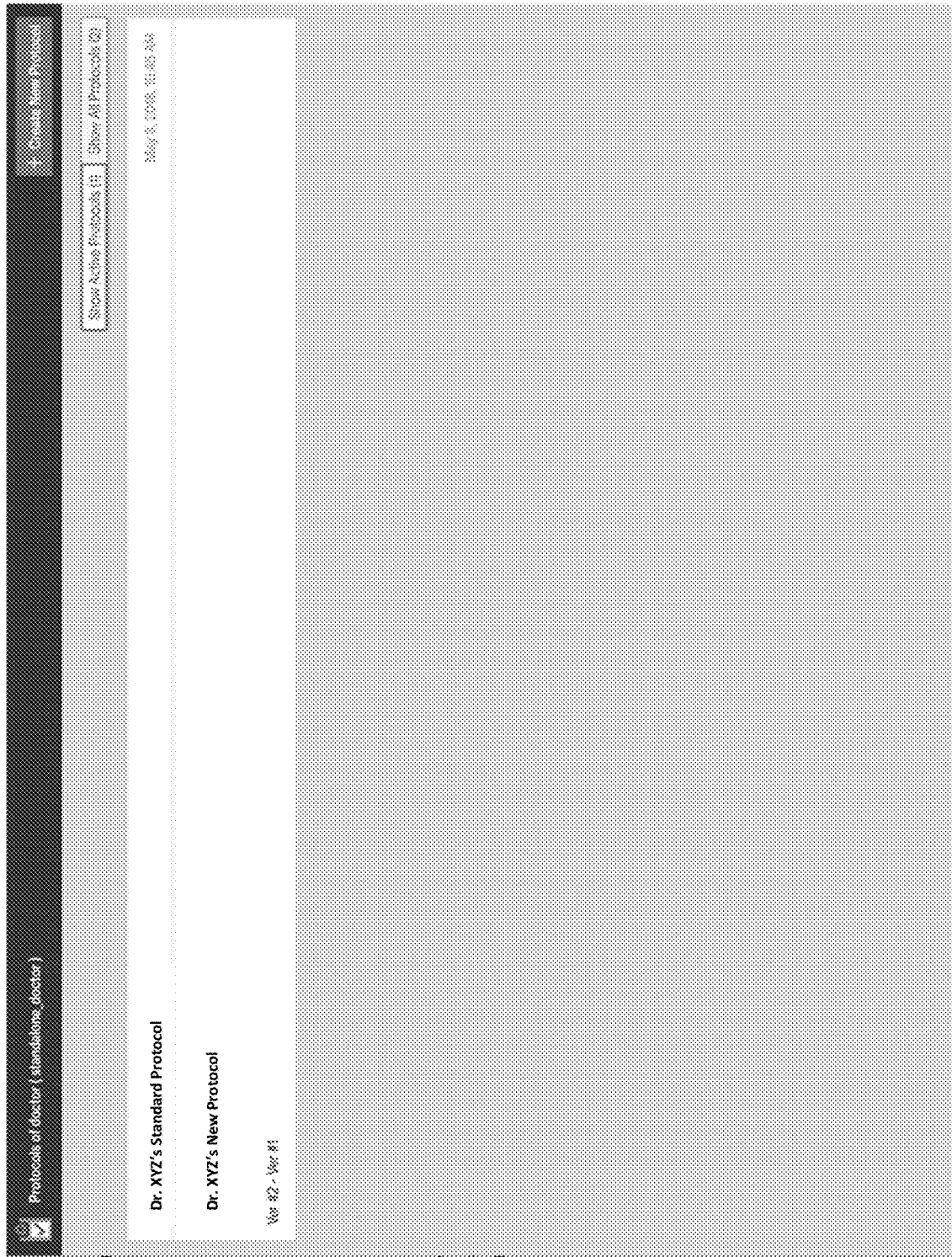
FIG. 22 shows an exemplary protocol management user interface.
Figure 23:
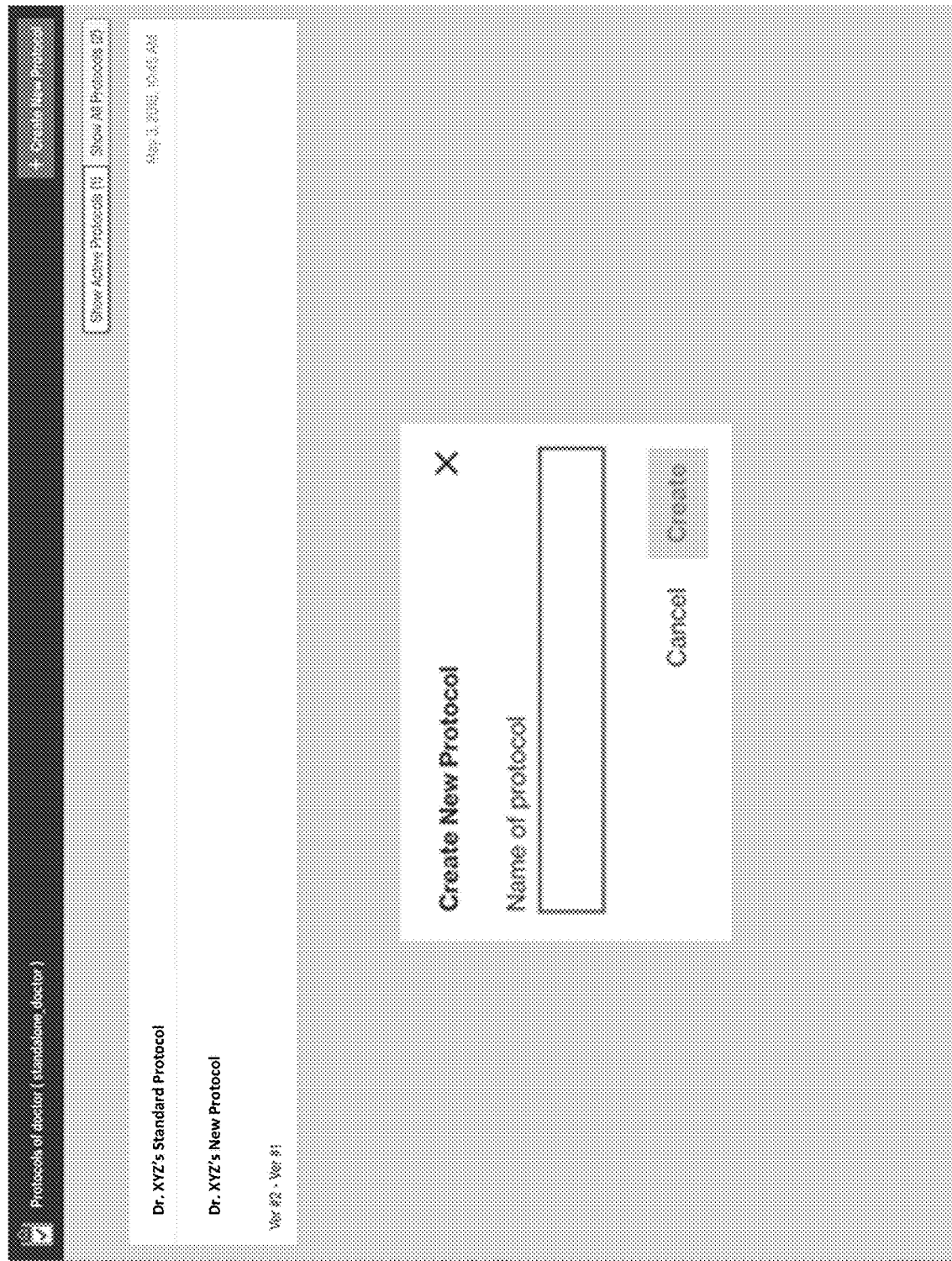
FIG. 23 illustrates one example of a user interface for creating a new protocol.
Figure 24:
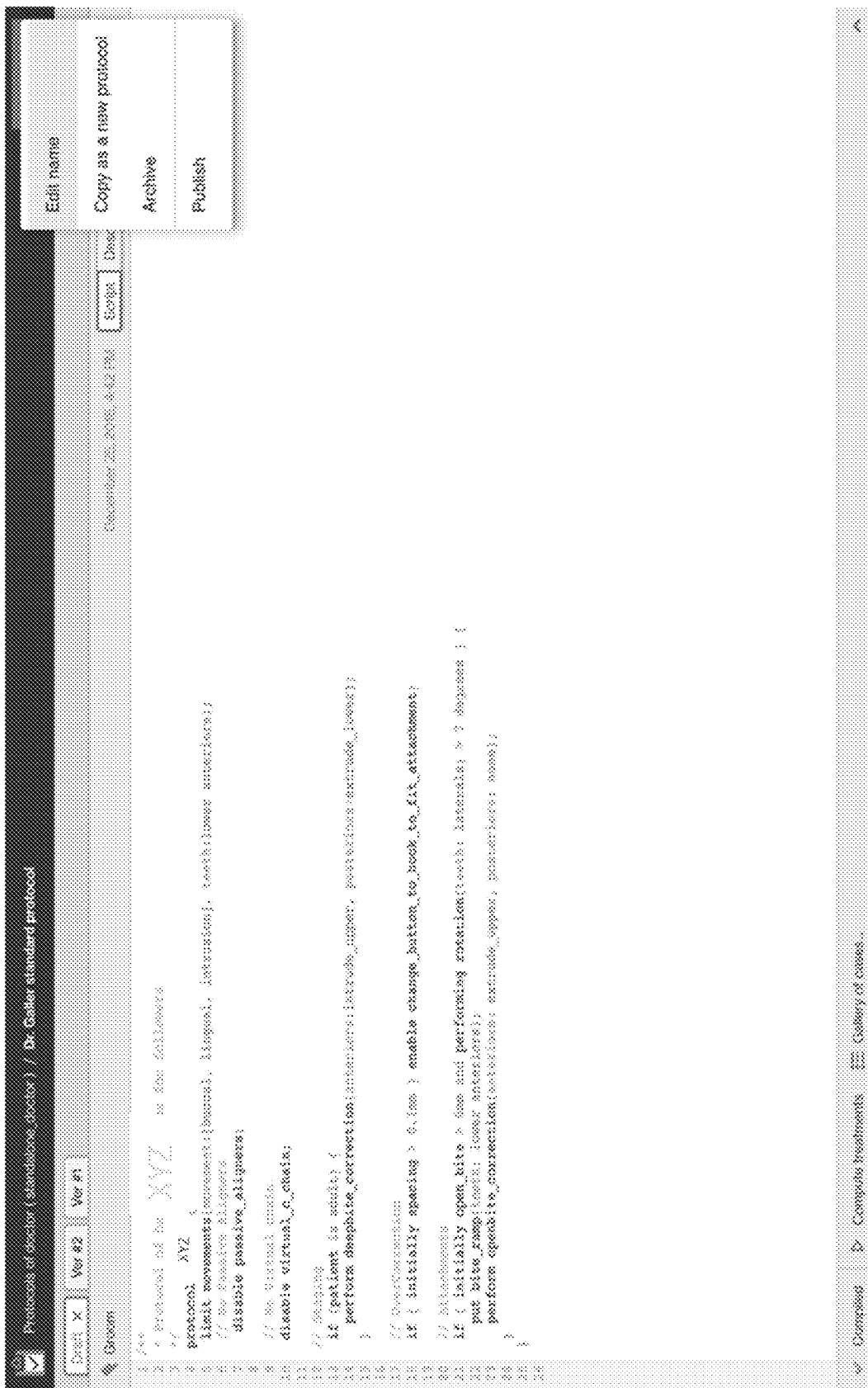
FIG. 24 shows on example of a user interface for archiving, deleting, publishing or modifying the name of the protocol.

An exemplary protocol management user interface is shown in FIG. 22. In this example, the protocol manager allows the system to display information about one or multiple user-specific treatment planning protocols, and may allow one or more of: creating a new protocol (FIG. 23), displaying a list of protocols (as shown in FIG. 22), and archive, delete, publish or modify the name of the protocol (FIG. 24) and/or work with different versions of protocols.

Figure 25:
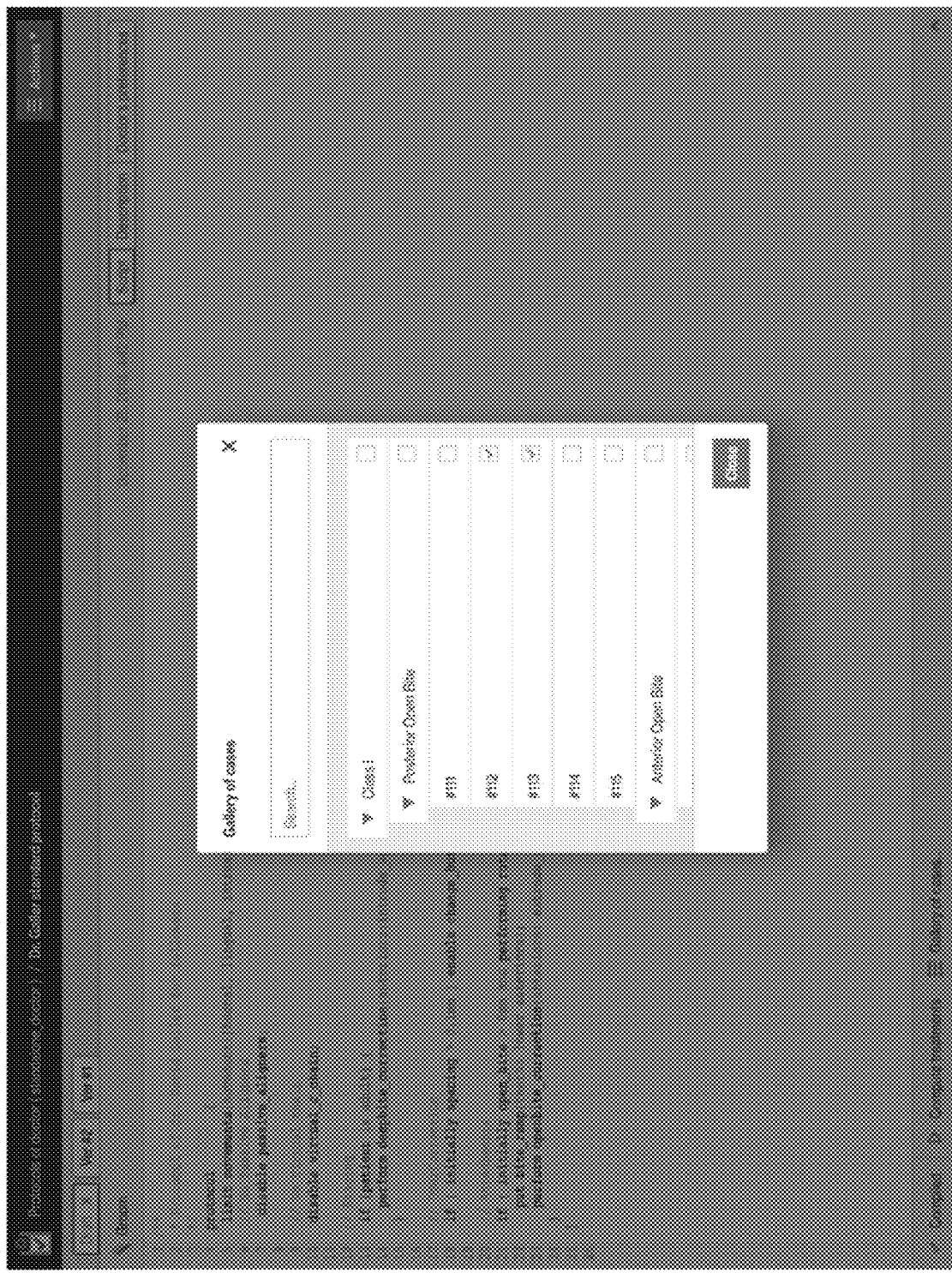
FIG. 25 is one example of a user interface showing a list of cases that the system may use for validation

In any of the methods and systems described herein, a putative final protocol may be validated by applying it to any available (historical) case, e.g., based on sample patients. FIG. 25 illustrates an example of a user interface showing a list of cases that the system may use for validation. A formalized protocol can be applied to examine whether the protocol valid or not using any of these historical cases, which may be referred to as gallery cases. Gallery cases may be categorized by clinical conditions and anonymized.

FIG. 26 shows one example of a user interface for treatment review and validation. In FIG. 26, the left side 2601 of the screen (which may be visible to either or both the technician and/or the user) shows the putative treatment protocol in the domain-specific orthodontic treatment language. The right side 2603 shows a treatment plan review view in which the appearance of the teeth are shown for each stage of the treatment plan (stages are shown on the bottom right 2605). Controls on the user interface may allow the user to select which stage to view (or loop through) and the orientation and/or size of the teeth may be adjusted using one or more of the tools 2609. Thus, the application may provide a 3D treatment plan review of a cases on which the putative protocol has been applied. To define a validity of protocol, a validation tool may display any of the following metrics: arch expansion per quadrant, overjet, overbite, interincisal angle, and may alert or trigger a flag if a treatment plan conforms to minimal root movements protocol.

FIG. 27 is an example user interface illustrating various user preferences. In some variations the user interface (e.g. for a system) may display a list of a user's preferences as the results of statistical analysis of actual user's clinical behavior. This data may be used to enhance formalization of preferences, and can give some extra insights that can be missed during verbal communication between the technician and the user. At least some user preferences may be provided, including but not limited to: list of frequently requested per-case text instructions, list of frequently requested text instructions. Some preferences may include a domain-specific orthodontic treatment language snippet that can be exported to a protocol script.

Figure 29:
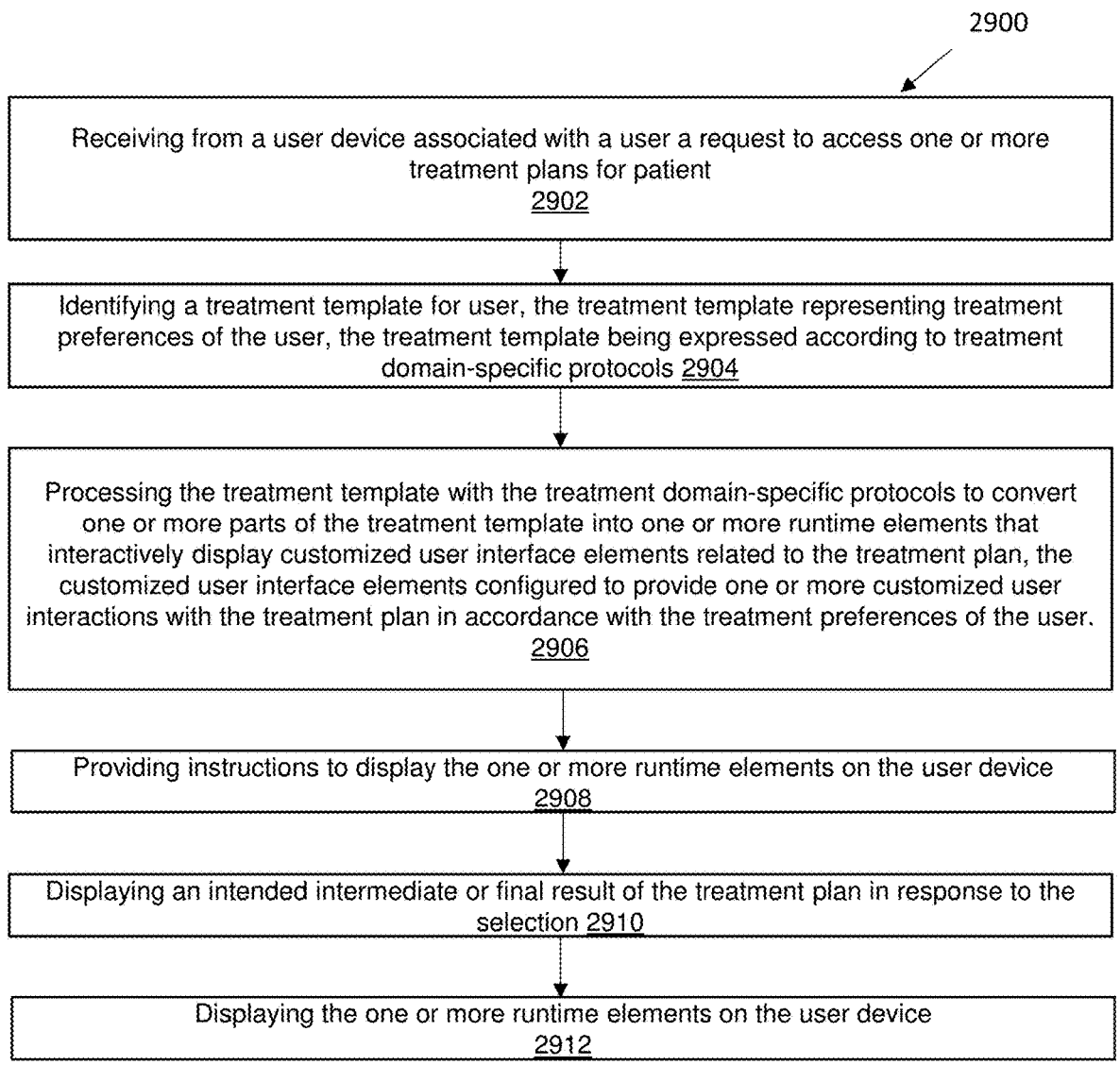
FIG. 29 is a diagram showing a flowchart of an example method of configuring runtime elements that display customized user interface elements related to a treatment plan on a user device.

FIG. 29 is a diagram showing a flowchart of an example method 2900 of configuring runtime elements that display customized user interface elements related to a treatment plan on a user device. The method 2900 may include a greater or fewer number of operations than those shown. The method 2900 may be executed by any of the systems, devices, and/or structures described herein, alone or in combination.

At an operation 2902, a request to access one or more treatment plans for patient is received from a user device. The user may be a dentist, orthodontist, or other medical professional. As noted herein, the one or more treatment plans may comprise one or more automatically generated treatment plans generated by an automated agent. The customized user interface elements may be displayed on an application, a webpage, or a mobile application on the user device.

At an operation 2904, a treatment template is identified for the user. The treatment template may represent treatment preferences of the user. The treatment template may be expressed according to various treatment domain-specific protocols. In some examples, the treatment template is identified after the request to access the one or more treatment plans is received, though other orders are expressly contemplated. As noted herein, the treatment domain-specific protocols may comprise dental domain-specific treatment protocols, orthodontic domain-specific treatment protocols, or some combination thereof. The one or more treatment plans may comprise one or more restorative treatment plans, one or more orthodontic treatment plans, or some combination thereof. In some examples, the one or more treatment plans comprise instructions to implement a series of aligners to resiliently reposition teeth of the patient from an initial position toward a final position.

At an operation 2906, the treatment template may be processed with the treatment domain-specific protocols to convert one or more parts of the treatment template into one or more runtime elements that interactively display customized user interface elements related to the treatment plan. In some implementations, the customized user interface elements are configured to provide one or more customized user interactions with the treatment plan in accordance with the treatment preferences of the user. In some implementations, a selection of at least one of the one or more treatment plans from the customized user interface elements may be received. As noted herein, the customized user interface elements may comprise an interactive display of the treatment preferences. As noted herein, the interactive display of treatment preferences may represent one or more interactive automated conditional treatment steps to implement the treatment plan in accordance with the treatment preferences. As an example, the one or more interactive automated conditional treatment steps may comprise an automated treatment option conditioned on the presence or absence of a physical condition indicated by patient data associated with the patient. As additionally noted herein, the one or more interactive automated conditional treatment steps may comprise an automated treatment option conditioned on the presence or absence of a physical condition indicated by patient data associated with the patient; the physical condition may be related to an initial tooth position, an intended final position of the treatment plan, the treatment goals of the treatment plan. The one or more interactive automated conditional treatment steps may be based on one or more conditional functions expressed according to treatment domain-specific protocols.

The interactive display of treatment preferences can represent historic treatment preferences of the user, historic preferences of other users (e.g., users who have treated a number of cases greater than a specified threshold indicating expertise in a specific area of treatment; users who have treated more cases that the cases the requesting user seeking a treatment plan has treated, etc.).

The interactive display of treatment preferences may represent one or more interactive automated iterative treatment steps to implement the treatment plan in accordance with the treatment preferences. The interactive display of treatment preferences may represent one or more interactive automated iterative treatment steps to implement the treatment plan in accordance with the treatment preferences. In some implementations, the one or more automated iterative treatment steps repeat a treatment option across a series of related portions of anatomy. Further, the one or more automated iterative treatment steps repeat a treatment option across a series of related portions of anatomy; the related portions of anatomy may comprise teeth in a specific region of the dentition. The one or more automated iterative treatment steps may repeat a treatment option across a series of related portions of anatomy; the one or more interactive automated iterative treatment steps may be based on an iterative function expressed according to treatment domain-specific protocols.

The interactive display of treatment preferences may represent one or more automated nested treatment steps to implement the treatment plan in accordance with the treatment preferences. The interactive display of treatment preferences may represent one or more automated listed treatment steps to implement the treatment plan in accordance with the treatment preferences. The treatment template may comprise a public or private treatment template.

At an operation 2908, instructions to display the one or more runtime elements on the user device are provided. At an operation 2910, an intended intermediate or final result of the treatment plan is displayed according to the selection. At an operation 2912, the one or more runtime elements are displayed on the user device.

Figure 30:
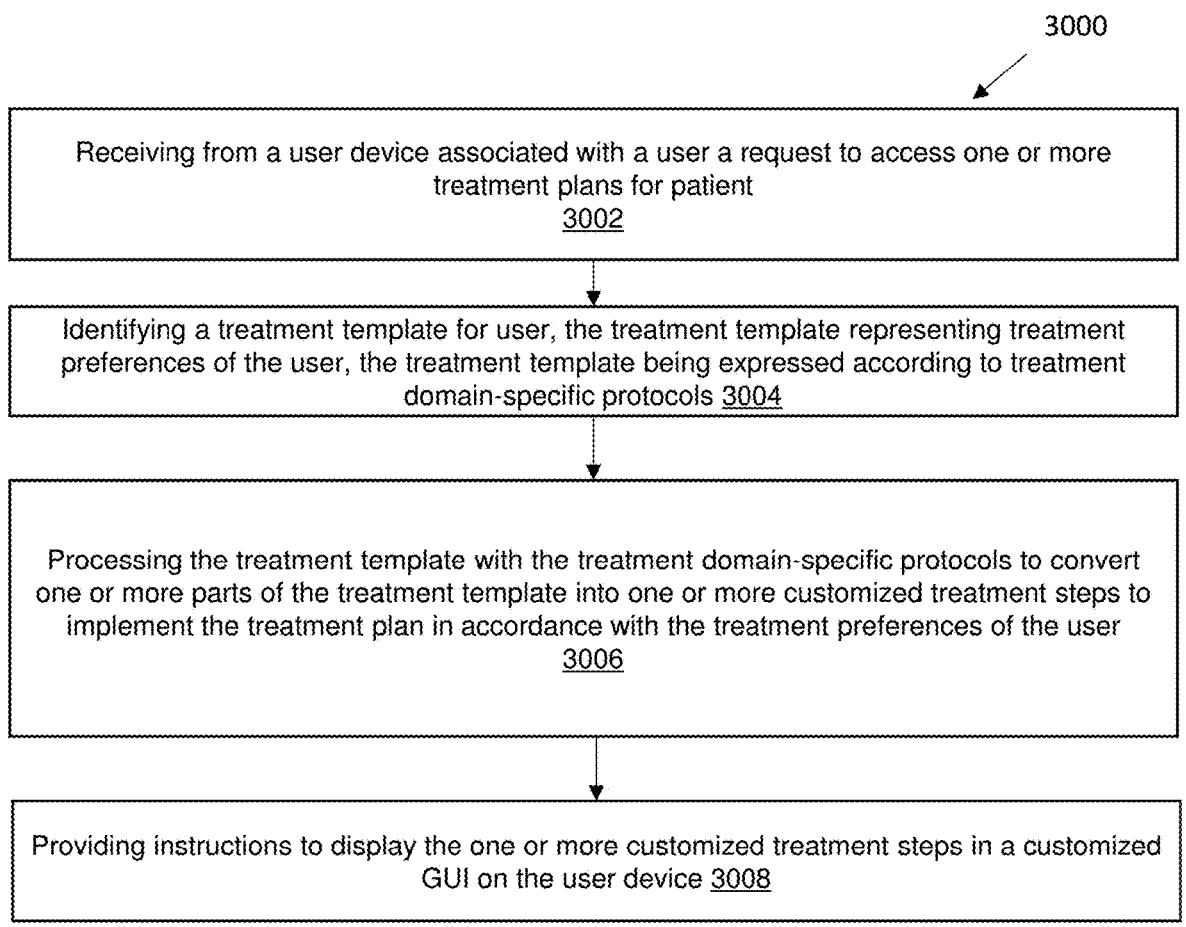
FIG. 30 is a diagram showing a flowchart of an example method of configuring a customized graphical user interface (GUI) that displays customized user interface elements related to a treatment plan on a user device.

FIG. 30 is a diagram showing a flowchart of an example method 3000 of configuring a customized graphical user interface (GUI) that displays customized user interface elements related to a treatment plan on a user device. The method 3000 may include a greater or fewer number of operations than those shown. The method 3000 may be executed by any of the systems, devices, and/or structures described herein, alone or in combination.

At an operation 3002, a request to access one or more treatment plans for patient is received from a user device.

At an operation 3004, a treatment template is identified for the user. The treatment template may represent treatment preferences of the user. The treatment template may be expressed according to various treatment domain-specific protocols.

At an operation 3006, the treatment template may be processed with the treatment domain-specific protocols to convert one or more parts of the treatment template into one or more customized treatment steps to implement the treatment plan in accordance with the treatment preferences of the user. The customized treatment steps may comprise one or more conditional treatment steps conditioning application of at least a portion of the treatment plan on the existence or the absence of a physical condition related to the patient. In some implementations, the physical condition is related to an initial physical condition or an intended physical outcome of the treatment plan. As noted herein, the customized treatment steps may comprise one or more conditional treatment steps conditioning application of at least a portion of the treatment plan on a feature associated with an appliance configured to implement the treatment plan on the patient.

Further, the feature may comprise, e.g., one or more of attachments, hooks, elastics, bite ramps, power ridges, or a physical geometry of a portion of an aligner. In some implementations, wherein the customized treatment steps comprise one or more conditional treatment steps conditioning application of at least a portion of the treatment plan on a procedure performed at a specific stage of the treatment plan. In some implementations, the customized treatment steps comprise one or more conditional treatment steps conditioning application of at least a portion of the treatment plan on a procedure performed at a specific stage of the treatment plan; the procedure may comprise, e.g., interproximal reduction performed in accordance with the treatment plan.

The customized treatment steps may comprise one or more iterative treatment steps repeating application of at least a portion of the treatment plan on the patient. As noted herein, the one or more automated iterative treatment steps may repeat a treatment option across a series of related portions of anatomy. Further, the one or more automated iterative treatment steps may repeat an orthodontic treatment option across a specific portion of dentition of the patient. In various implementations, the customized treatment steps may comprise one or more nested treatment steps that organize parts of the treatment plan according to a hierarchy of treatment rules. The treatment domain-specific protocols may comprise dental domain-specific treatment protocols, orthodontic domain-specific treatment protocols, or some combination thereof.

In some implementations, processing the treatment template comprises parsing the treatment template using the treatment domain-specific protocols. Parsing the treatment template may include executing an automated script on the treatment template.

In some implementations, at least a portion of the treatment plan is gathered using the customized treatment steps.

At an operation 3008, instructions to display the one or more customized treatment steps in a customized GUI are provided.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method comprising:
receiving from a user device associated with a user, a request to access one or more treatment plans for a patient;
receiving a selection of a treatment template from a library of treatment templates, the treatment template representing treatment preferences of the user, the treatment template being expressed according to treatment domain-specific protocols that include domain-specific orthodontic treatment language that is both manually and machine readable and capable of being parsed by a processor into a set of treatment planning instructions;

receiving instructions to modify the treatment template with one or more user-selected modifications to the treatment template;

presenting a customized user interface based on the modified treatment template, wherein the modified treatment template includes instructions to generate one or more runtime elements that interactively display customized user interface elements related to the one or more treatment plans, the customized user interface elements configured to provide one or more customized user interactions with the one or more treatment plans in accordance with the treatment preferences of the user, wherein the customized user interface elements provide one or more user-selectable conditions under which at least one of the treatment preferences is included, and wherein processing the treatment template includes translating the treatment domain-specific protocols into the set of treatment planning instructions to generate the one or more treatment plans;

receiving a selection of at least one of the one or more treatment plans from the customized user interface elements; and generating instructions to fabricate one or more dental treatment appliances based on the selected at least one of the one or more treatment plans.

2. The method of claim 1, further comprising displaying an intended intermediate or final result of the one of the one or more treatment plans in response to the selection.

3. The method of claim 1, further comprising displaying the one or more runtime elements on the user device.

4. The method of claim 1, wherein the customized user interface elements comprise an interactive display of the treatment preferences.

5. The method of claim 4, wherein the interactive display of customized user interface elements represents one or more interactive automated conditional treatment steps to implement the one or more treatment plans in accordance with the treatment preferences.

6. The method of claim 4, wherein:
the interactive display of customized user interface elements represents one or more interactive automated conditional treatment steps to implement the one or more treatment plans in accordance with the treatment preferences; and
the one or more interactive automated conditional treatment steps comprise an automated treatment option conditioned on a presence or absence of a physical condition indicated by patient data associated with the patient.

7. The method of claim 4, wherein:
the interactive display of customized user interface elements represents one or more interactive automated conditional treatment steps to implement the one or more treatment plans in accordance with the treatment preferences;
the one or more interactive automated conditional treatment steps comprises an automated treatment option conditioned on a presence or absence of a physical condition indicated by patient data associated with the patient; and
the physical condition is related to an initial tooth position, an intended final position of a treatment plan, and treatment goals of the treatment plan.

8. The method of claim 4, wherein:
the interactive display of customized user interface elements represents one or more interactive automated conditional treatment steps to implement the one or more treatment plans in accordance with the treatment preferences; and
the one or more interactive automated conditional treatment steps are based on one or more conditional functions expressed according to the treatment domain-specific protocols.

9. The method of claim 1, wherein the treatment template comprises a public treatment template or a private treatment template.

10. The method of claim 4, wherein the interactive display of customized user interface elements represents historic treatment preferences of the user.

11. The method of claim 4, wherein the interactive display of customized user interface elements represents historic treatment preferences of another user.

12. The method of claim 4, wherein the interactive display of customized user interface elements represents historic treatment preferences of another user; and the other user has treated a first number of cases greater than a specified threshold indicating expertise in a specific area of treatment.

13. The method of claim 12, wherein the interactive display of customized user interface elements represents historic treatment preferences of another user; and the specified threshold is greater than a second number of cases the user has treated.

14. The method of claim 4, wherein the interactive display of customized user interface elements represents one or more interactive automated iterative treatment steps to implement the one or more treatment plans in accordance with the treatment preferences.

15. The method of claim 4, wherein:
the interactive display of customized user interface elements represents one or more automated iterative treatment steps to implement the one or more treatment plans in accordance with the treatment preferences; and
the one or more automated iterative treatment steps repeat a treatment option across a series of related portions of anatomy.

16. The method of claim 4, wherein:
the interactive display of customized user interface elements represents one or more automated iterative treatment steps to implement the one or more treatment plans in accordance with the treatment preferences;
the one or more automated iterative treatment steps repeat a treatment option across a series of related portions of anatomy; and
the related portions of anatomy comprise teeth in a specific region of the patient's dentition.

17. The method of claim 4, wherein:
the interactive display of customized user interface elements represents one or more automated iterative treatment steps to implement the one or more treatment plans in accordance with the treatment preferences;
the one or more automated iterative treatment steps repeat a treatment option across a series of related portions of anatomy; and
the one or more interactive automated iterative treatment steps are based on an iterative function expressed according to the treatment domain-specific protocols.

18. The method of claim 4, wherein the interactive display of customized user interface elements represents one or more automated nested treatment steps to implement the one or more treatment plans in accordance with the treatment preferences.

19. The method of claim 4, wherein the interactive display of customized user interface elements represents one or more automated listed treatment steps to implement one or more treatment plans in accordance with the treatment preferences.

20. The method of claim 1, wherein the one or more treatment plans comprises one or more automatically generated treatment plans generated by an automated agent.

21. The method of claim 1, wherein the customized user interface elements are displayed on an application, a webpage, or a mobile application on the user device.

22. The method of claim 1, wherein the treatment domain-specific protocols comprise dental domain-specific treatment protocols, orthodontic domain-specific treatment protocols, or some combination thereof.

23. The method of claim 1, wherein the one or more treatment plans comprise one or more restorative treatment plans, one or more orthodontic treatment plans, or some combination thereof.

24. The method of claim 1, wherein the one or more treatment plans comprise instructions to implement a series of aligners to resiliently reposition teeth of the patient from an initial position toward a final position.

25. The method of claim 1, wherein the user comprises a dentist, orthodontist, or other medical professional.

26. The method of claim 1, wherein the treatment template is identified after the request to access the one or more treatment plans is received.

27. The method of claim 1, wherein generating the one or more treatment plans comprises including patient specific information about the patient.

28. The method of claim 27, wherein the patient specific information includes data from a scan of the patient's oral cavity.

29. The method of claim 1, wherein the treatment preferences of the user include one or more of: whether there are tooth movement restrictions, whether interproximal reduction (IPR) should be used, when during treatment to perform IPR, where to perform IPR, whether attachments should be used, where attachments should be placed, changes in spacing distance between teeth, whether there is a tooth extraction, and whether to implement leveling strategy.

30. The method of claim 1, wherein the one or more user-selectable conditions refers to one or more of a tooth position, a tooth type and a tooth ordering sequence.

31. The method of claim 1, further comprising receiving instructions to further modify the treatment template via the customized user interface based on selected treatment preferences of the user.

32. A system comprising:
one or more processors;
memory coupled to the one or more processors, the memory configured to store computer-program instructions that, when executed by the one or more processors cause the system to implement a method comprising:
receiving from a user device associated with a user a request to access one or more treatment plans for a patient;
receiving a selection of a treatment template from a library of treatment templates, the treatment template representing treatment preferences of the user, the treatment template being expressed according to treatment domain-specific protocols that include domain-specific orthodontic treatment language that is both manually and machine readable and capable of being parsed by a processor into a set of treatment planning instructions;
receiving instructions to modify the treatment template with one or more user-selected modifications to the treatment template;
presenting a customized user interface based on the modified treatment template, wherein the modified treatment template includes instructions to generate one or more runtime elements that interactively display customized user interface elements related to the one or more treatment plans, the customized user interface elements configured to provide one or more customized user interactions with the one or more treatment plans in accordance with the treatment preferences of the user, wherein the customized user interface elements provide one or more user-selectable conditions under which at least one of the treatment preferences is included, and wherein processing the treatment template includes translating the treatment domain-specific protocols into the set of treatment planning instructions to generate the one or more treatment plans;
receiving a selection of at least one of the one or more treatment plans from the customized user interface elements; and
generating instructions to fabricate one or more dental treatment appliances based on the selected at least one of the one or more treatment plans.

* * * * *